"""

US010718022B2

(12) United States Patent
Green et al.

(10) Patent No.: US 10,718,022 B2
(45) Date of Patent: Jul. 21, 2020

(54) COMPOSITIONS AND METHODS FOR Xi CHROMOSOME REACTIVATION

(71) Applicant: University of Massachusetts, Boston, MA (US)

(72) Inventors: Michael R. Green, Boylston, MA (US); Sanchita Bhatnagar, Free Union, VA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/566,533

(22) PCT Filed: Apr. 15, 2016

(86) PCT No.: PCT/US2016/027840
§ 371 (c)(1),
(2) Date: Oct. 13, 2017

(87) PCT Pub. No.: WO2016/168658
PCT Pub. Date: Oct. 20, 2016

(65) Prior Publication Data
US 2018/0087110 A1    Mar. 29, 2018

Related U.S. Application Data

(60) Provisional application No. 62/148,106, filed on Apr. 15, 2015.

(51) Int. Cl.
*C12Q 1/6883* (2018.01)
*G01N 33/50* (2006.01)

(52) U.S. Cl.
CPC ....... *C12Q 1/6883* (2013.01); *G01N 33/5023* (2013.01); *A01K 2227/10* (2013.01); *C12Q 2600/156* (2013.01); *C12Q 2600/158* (2013.01); *C12Q 2600/178* (2013.01)

(58) Field of Classification Search
CPC .......................... A01K 2207/05; C12N 15/113
See application file for complete search history.

(56) References Cited

U.S. PATENT DOCUMENTS

| | | | |
|---|---|---|---|
| 2001/0041337 A1 | 11/2001 | Szyf et al. | |
| 2011/0076678 A1* | 3/2011 | Jaenisch | C07K 14/4702 435/6.14 |
| 2011/0195966 A1 | 8/2011 | Garcia-Echeverria et al. | |
| 2012/0122790 A1 | 5/2012 | Drezner et al. | |
| 2013/0004985 A1* | 1/2013 | Marchetto | G01N 33/5058 435/29 |
| 2014/0142160 A1* | 5/2014 | Lee | C12N 15/113 514/44 A |
| 2016/0313304 A1* | 10/2016 | Guttman | A61K 38/17 |
| 2017/0327823 A1* | 11/2017 | Lee | C07H 21/00 |
| 2017/0335317 A1* | 11/2017 | Lee | C40B 20/08 |

FOREIGN PATENT DOCUMENTS

| | | | |
|---|---|---|---|
| WO | WO 2007/054720 A1 | 5/2007 | |
| WO | WO 2013/163455 A2 | 10/2013 | |
| WO | WO 2014/025887 A1 | 2/2014 | |
| WO | WO-2014052393 A2 * | 4/2014 | ......... G01N 33/6893 |
| WO | WO 2016/164463 A1 | 10/2016 | |

OTHER PUBLICATIONS

Bhatnagar et al. PNAS 111, 12591-12598, Sep. 2 (Year: 2014).*
Ohhata et al. Cell. Mol. Life Sci. 70: 2443-2461 (Year: 2013).*
Hysolli et al. Cell Cycle 11: 229-235 (Year: 2012).*
Cantone et al. Phil. Trans R. Soc. 372; p. 1-8 (Year: 2017).*
Cheung et al. Frontiers in psychiatry vol. 3, pp. 1-16 (Year: 2012).*
Weaving et al. Am. J. Hum. Genet. 75:1079-1093 (Year: 2004).*
NORD National Organization for Rare Disorders, CDKL5, retrieved on Dec. 3, 2019, pp. 1-10, https://rarediseases.org/rare-diseases/cdkl5/ (Year: 2015).*
Przanowski et al., Pharmacological reactivation of inactive X-linked Mecp2 in cerebral cortical neurons of living mice. Proc Natl Acad Sci USA. Jul. 31, 2018;115(31):7991-7996. doi: 10.1073/pnas. 1803792115. Epub Jul. 16, 2018.

* cited by examiner

*Primary Examiner* — Brian Whiteman

(74) *Attorney, Agent, or Firm* — Wolf, Greenfield & Sacks, P.C.

(57) ABSTRACT

In some aspects, the disclosure relates to the reactivation of inactive X chromosomes (Xi). In some embodiments, the disclosure provides compositions and methods for the reactivation of inactive X chromosomes. In some embodiments, the compositions and methods described by the disclosure may be useful for the treatment of dominant X-linked diseases.

11 Claims, 41 Drawing Sheets

Specification includes a Sequence Listing.

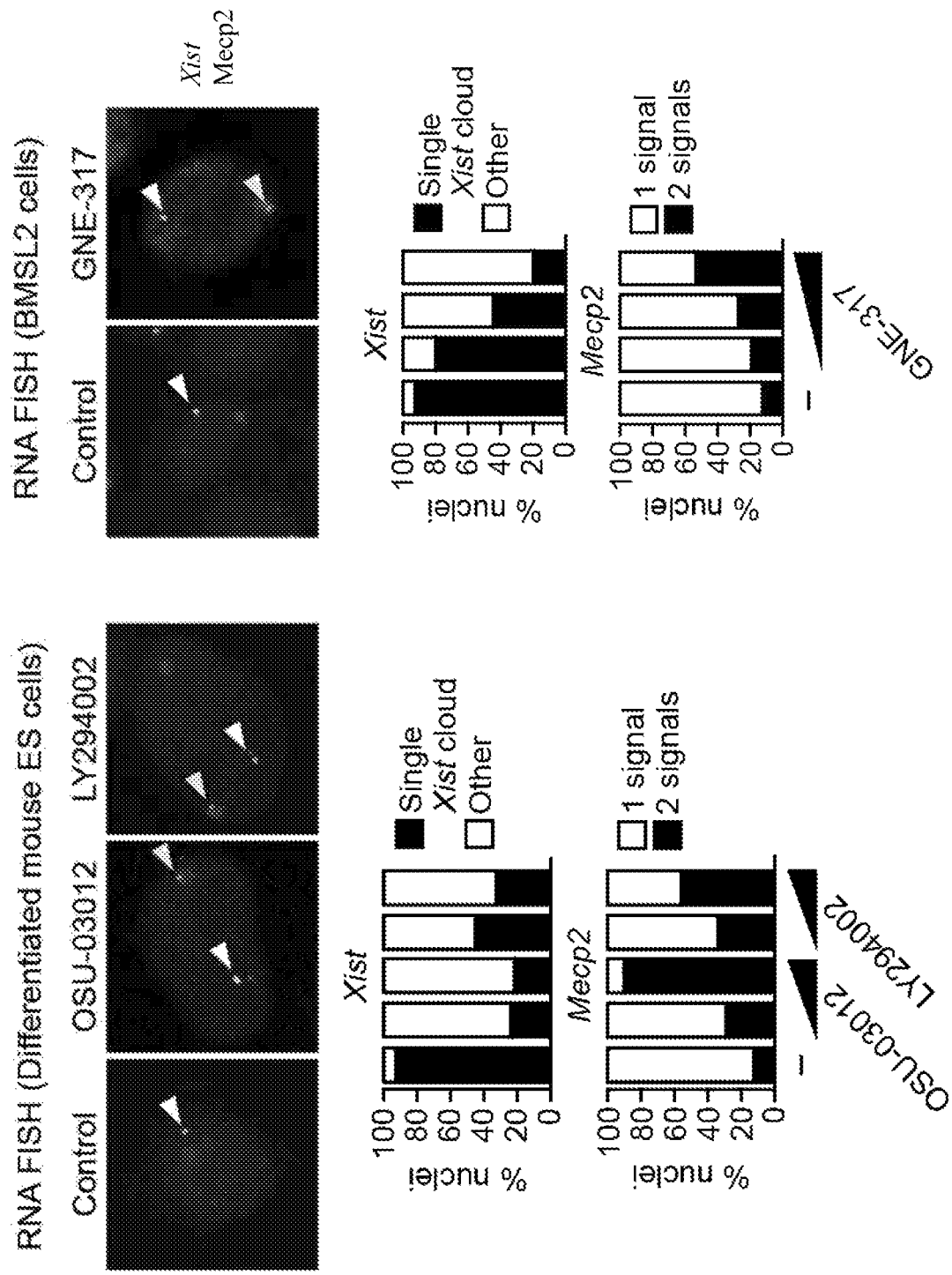

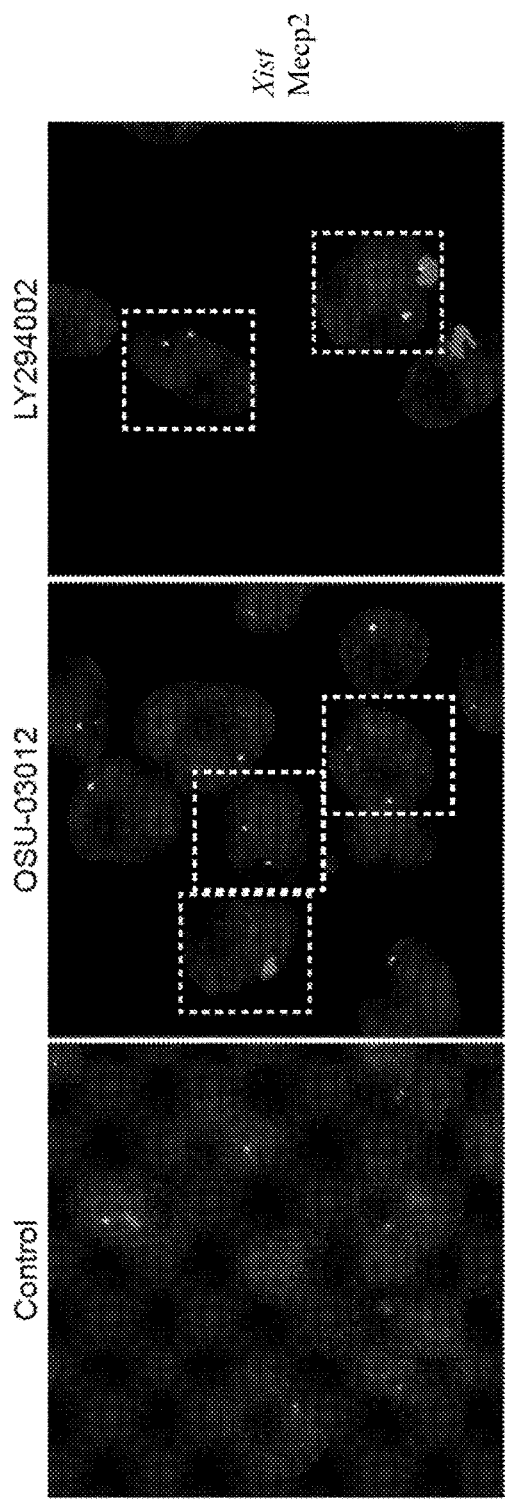
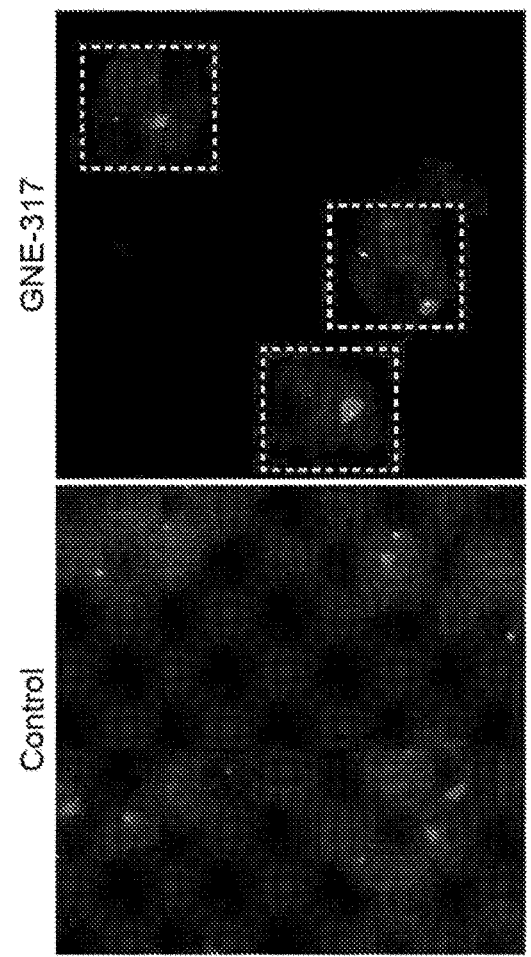
FIG. 11A
FIG. 11B

| Gene | Expressed allele | Restriction enzyme | Digested paternal (Cast) allele (bp) | Digested maternal (C57BL/6) allele (bp) |
|---|---|---|---|---|
| Kcnq1ot1 | Paternal | StuI | 213, 601 | 814 |
| Peg3 | Paternal | MnlI | 487 | 110, 377 |
| Ascl2 | Maternal | SfcI | 207, 266 | 474 |
| Zim1 | Maternal | FauI | 236, 254 | 490 |
FIG. 13C Cont.
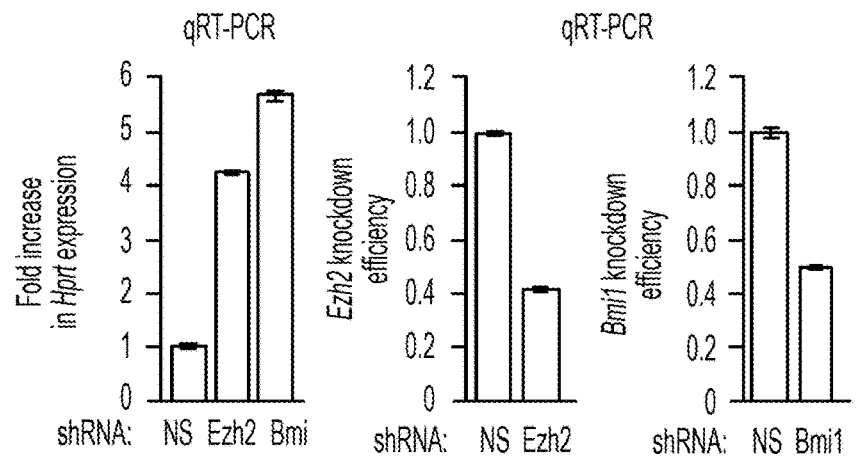
FIG. 13D
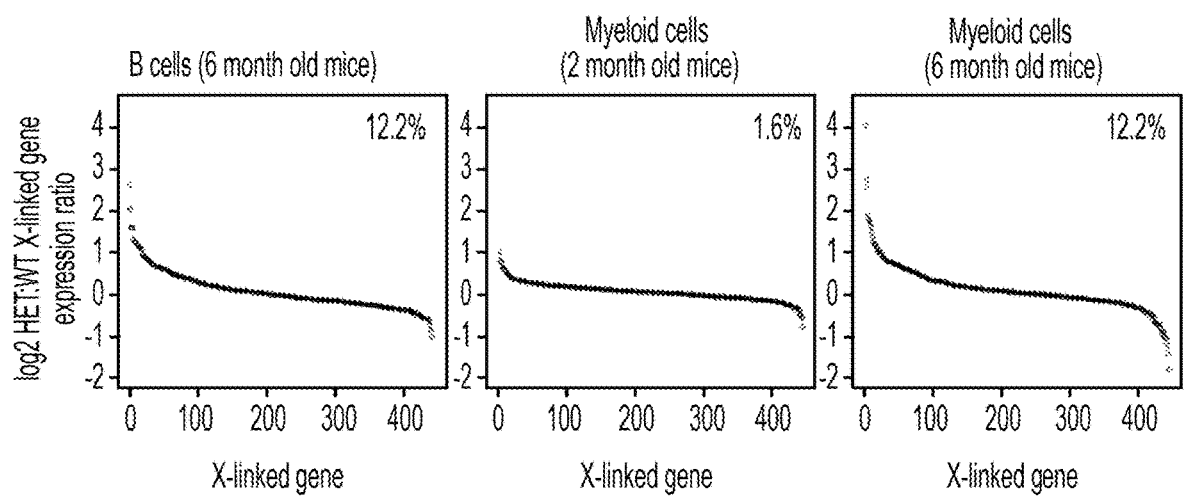
FIG. 13E

SEQUENCE LISTING

<160> NUMBER OF SEQ ID NOS: 119

<210> SEQ ID NO 1
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 1
ttgccgacag gatgcagaa                                            19

<210> SEQ ID NO 2
<211> LENGTH: 20
<212> TYPE: DNA
<213> ORGANISM: Mus musculus

<400> SEQUENCE: 2
ggccagcagt gttttcttc                                            20

<210> SEQ ID NO 3
<211> LENGTH: 20
<212> TYPE: DNA
<213> ORGANISM: Homo sapiens

<400> SEQUENCE: 3
tcaggaagtg gctctggtct                                           20

<210> SEQ ID NO 4
<211> LENGTH: 20
<212> TYPE: DNA
<213> ORGANISM: Mus musculus

<400> SEQUENCE: 4
taggatactg cttgttactt                                           20

```
<210> SEQ ID NO 5
<211> LENGTH: 20
<212> TYPE: DNA
<213> ORGANISM: Homo sapiens

<400> SEQUENCE: 5
tggaatatgc accacttgga                                                  20

<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6
aaatcagggg gttgaaaaat ct                                               22

<210> SEQ ID NO 7
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 7
gccaagtgaa aaccaggaca aaagac                                           26

<210> SEQ ID NO 8
<211> LENGTH: 25
<212> TYPE: DNA
<213> ORGANISM: Mus musculus

<400> SEQUENCE: 8
ggaaggctac ctggctaaag tcaag                                            25

<210> SEQ ID NO 9
<211> LENGTH: 20
<212> TYPE: DNA
<213> ORGANISM: Homo sapiens

<400> SEQUENCE: 9
gtgggggact gtgtctctgt                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
cctggtggtg ttttgttgtg                                                  20

<210> SEQ ID NO 11
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 11
ctaattggta cttactacga taacttt                                          27

<210> SEQ ID NO 12
```

```
<211> LENGTH: 20
<212> TYPE: DNA
<213> ORGANISM: Mus musculus

<400> SEQUENCE: 12
gctgagccat tttcttctcg                                              20

<210> SEQ ID NO 13
<211> LENGTH: 20
<212> TYPE: DNA
<213> ORGANISM: Homo sapiens

<400> SEQUENCE: 13
caagggttgt ggagagtggt                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
atggccttcc gtgttcctac                                              20

<210> SEQ ID NO 15
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 15
tcaaagcaca cgccctctt                                               19

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
aagcttgctg gtgaaaagga                                              20

<210> SEQ ID NO 17
<211> LENGTH: 20
<212> TYPE: DNA
<213> ORGANISM: Mus musculus

<400> SEQUENCE: 17
gcaaggagag tggatgggta                                              20

<210> SEQ ID NO 18
<211> LENGTH: 18
<212> TYPE: DNA
<213> ORGANISM: Homo sapiens

<400> SEQUENCE: 18
ctacaggccg tgctgctg                                                18

<210> SEQ ID NO 19
<211> LENGTH: 21
<212> TYPE: DNA
<213> ORGANISM: Artificial Sequence
```

```
<220> FEATURE:
<223> OTHER INFORMATION: Synthetic Polynucleotide

<400> SEQUENCE: 19
catggtagct gggatgttag g                                              21

<210> SEQ ID NO 20
<211> LENGTH: 20
<212> TYPE: DNA
<213> ORGANISM: Mus musculus

<400> SEQUENCE: 20
gtagccacag gtcccttgtc                                                20

<210> SEQ ID NO 21
<211> LENGTH: 20
<212> TYPE: DNA
<213> ORGANISM: Homo sapiens

<400> SEQUENCE: 21
aattctgcct ctggggtttt                                                20

<210> SEQ ID NO 22
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 22
ctcaccctgg gcgttctct                                                 19

<210> SEQ ID NO 23
<211> LENGTH: 20
<212> TYPE: DNA
<213> ORGANISM: Mus musculus

<400> SEQUENCE: 23
ggtccagtgg ataagcgaaa                                                20

<210> SEQ ID NO 24
<211> LENGTH: 20
<212> TYPE: DNA
<213> ORGANISM: Homo sapiens

<400> SEQUENCE: 24
gactcttccg tgcgttcttc                                                20

<210> SEQ ID NO 25
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 25
atgtcgcttt ccaacaagct g                                              21

<210> SEQ ID NO 26
<211> LENGTH: 20
<212> TYPE: DNA
<213> ORGANISM: Mus musculus

<400> SEQUENCE: 26
```
taatgtcagc ggaacaggac                                               20

<210> SEQ ID NO 27
<211> LENGTH: 20
<212> TYPE: DNA
<213> ORGANISM: Homo sapiens

<400> SEQUENCE: 27
atcctggctt tggaggctat                                               20

<210> SEQ ID NO 28
<211> LENGTH: 20
<212> TYPE: DNA
<213> ORGANISM: Mus musculus

<400> SEQUENCE: 28
atgcctccag ctacagccta                                               20

<210> SEQ ID NO 29
<211> LENGTH: 20
<212> TYPE: DNA
<213> ORGANISM: Homo sapiens

<400> SEQUENCE: 29
agggagagct ggaaaaggag                                               20

<210> SEQ ID NO 30
<211> LENGTH: 22
<212> TYPE: DNA
<213> ORGANISM: Mus musculus

<400> SEQUENCE: 30
gtggaagagg aggagagtga ga                                            22

<210> SEQ ID NO 31
<211> LENGTH: 20
<212> TYPE: DNA
<213> ORGANISM: Homo sapiens

<400> SEQUENCE: 31
agggactccc gagagcttag                                               20

<210> SEQ ID NO 32
<211> LENGTH: 22
<212> TYPE: DNA
<213> ORGANISM: Mus musculus

<400> SEQUENCE: 32
aagtcataca gcagcccaat ca                                            22

<210> SEQ ID NO 33
<211> LENGTH: 20
<212> TYPE: DNA
<213> ORGANISM: Homo sapiens

<400> SEQUENCE: 33
tgatcagtgc ttctgcaacc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
aaaacagctc ctccgattcc                                              20

<210> SEQ ID NO 35
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 35
caatctcgca agatccggtg a                                            21

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
ccctgctagt ttcccaatga                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 37
gatgccaacg acacgtctga                                              20

<210> SEQ ID NO 38
<211> LENGTH: 24
<212> TYPE: DNA
<213> ORGANISM: Homo sapiens

<400> SEQUENCE: 38
acgctgcatg tgtccttagt agtc                                         24

<210> SEQ ID NO 39
<211> LENGTH: 20
<212> TYPE: DNA
<213> ORGANISM: Mus musculus

<400> SEQUENCE: 39
atgacctttc gctcatggac                                              20

<210> SEQ ID NO 40
<211> LENGTH: 20
<212> TYPE: DNA
<213> ORGANISM: Homo sapiens

<400> SEQUENCE: 40
ctgaggtggg tggatcactt                                              20

<210> SEQ ID NO 41
<211> LENGTH: 19
<212> TYPE: DNA
<213> ORGANISM: Mus musculus

<400> SEQUENCE: 41
gctgatgtca actgtttcc                                              19

<210> SEQ ID NO 42
<211> LENGTH: 20
<212> TYPE: DNA
<213> ORGANISM: Homo sapiens

<400> SEQUENCE: 42
tcgggcaagg acaaagatac                                             20

<210> SEQ ID NO 43
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 43
gccgatccac acggagtact t                                           21

<210> SEQ ID NO 44
<211> LENGTH: 20
<212> TYPE: DNA
<213> ORGANISM: Mus musculus

<400> SEQUENCE: 44
ttcccctgct cataaacctg                                             20

<210> SEQ ID NO 45
<211> LENGTH: 20
<212> TYPE: DNA
<213> ORGANISM: Homo sapiens

<400> SEQUENCE: 45
cgtttccctg aaccatgact                                             20

<210> SEQ ID NO 46
<211> LENGTH: 18
<212> TYPE: DNA
<213> ORGANISM: Mus musculus

<400> SEQUENCE: 46
cctccaactg gagctgta                                               18

<210> SEQ ID NO 47
<211> LENGTH: 20
<212> TYPE: DNA
<213> ORGANISM: Homo sapiens

<400> SEQUENCE: 47
actgaccacc caaaatctgc                                             20

<210> SEQ ID NO 48
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 48
gctaaccacc aatcttcctt tg                                          22

<210> SEQ ID NO 49
<211> LENGTH: 23

```
<212> TYPE: DNA
<213> ORGANISM: Artificial Sequence
<220> FEATURE:
<223> OTHER INFORMATION: Synthetic Polynucleotide

<400> SEQUENCE: 49
gctgctgttg ctgctgctgc ttc                                            23

<210> SEQ ID NO 50
<211> LENGTH: 24
<212> TYPE: DNA
<213> ORGANISM: Mus musculus

<400> SEQUENCE: 50
actgaaaggg tgtcactgtc cgac                                           24

<210> SEQ ID NO 51
<211> LENGTH: 20
<212> TYPE: DNA
<213> ORGANISM: Homo sapiens

<400> SEQUENCE: 51
tgaaagctgc atgtcctcac                                                20

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 52
tttaatagca ccgggcactc                                                20

<210> SEQ ID NO 53
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 53
actctaaact catacacctg tctacat                                        27

<210> SEQ ID NO 54
<211> LENGTH: 20
<212> TYPE: DNA
<213> ORGANISM: Mus musculus

<400> SEQUENCE: 54
atgatggttt ctggccactc                                                20

<210> SEQ ID NO 55
<211> LENGTH: 20
<212> TYPE: DNA
<213> ORGANISM: Homo sapiens

<400> SEQUENCE: 55
atgtcaatgc ctccttggac                                                20

<210> SEQ ID NO 56
<211> LENGTH: 20
<212> TYPE: DNA
<213> ORGANISM: Artificial Sequence
<220> FEATURE:
```

```
<223> OTHER INFORMATION: Synthetic Polynucleotide

<400> SEQUENCE: 56
atagggcctc tcttgctcag                                          20

<210> SEQ ID NO 57
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 57
tagcgcacag ccagtttcc                                           19

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
ttgcgctcat cttaggcttt                                          20

<210> SEQ ID NO 59
<211> LENGTH: 20
<212> TYPE: DNA
<213> ORGANISM: Mus musculus

<400> SEQUENCE: 59
acttgtgatg ctgtgcttgc                                          20

<210> SEQ ID NO 60
<211> LENGTH: 20
<212> TYPE: DNA
<213> ORGANISM: Homo sapiens

<400> SEQUENCE: 60
ctgactagct ggcctccatc                                          20

<210> SEQ ID NO 61
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 61
gcaatcaatt ctactttaga gcg                                      23

<210> SEQ ID NO 62
<211> LENGTH: 25
<212> TYPE: DNA
<213> ORGANISM: Mus musculus

<400> SEQUENCE: 62
ctgagaacaa gtacacagag agtga                                    25

<210> SEQ ID NO 63
<211> LENGTH: 20
<212> TYPE: DNA
<213> ORGANISM: Homo sapiens

<400> SEQUENCE: 63
```

```
gctgtttcct tcaggagtcg                                              20

<210> SEQ ID NO 64
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 64
aggcctcgaa gcgacaga                                                18

<210> SEQ ID NO 65
<211> LENGTH: 20
<212> TYPE: DNA
<213> ORGANISM: Mus musculus

<400> SEQUENCE: 65
tttctgcacc acttgtgagc                                              20

<210> SEQ ID NO 66
<211> LENGTH: 20
<212> TYPE: DNA
<213> ORGANISM: Homo sapiens

<400> SEQUENCE: 66
gaggagaaag gtgacccaca                                              20

<210> SEQ ID NO 67
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 67
gctccattgt ccaagcagaa t                                            21

<210> SEQ ID NO 68
<211> LENGTH: 20
<212> TYPE: DNA
<213> ORGANISM: Mus musculus

<400> SEQUENCE: 68
ttatctgggc ttccgagttg                                              20

<210> SEQ ID NO 69
<211> LENGTH: 20
<212> TYPE: DNA
<213> ORGANISM: Homo sapiens

<400> SEQUENCE: 69
gtggcccaaa gttaaaagca                                              20

<210> SEQ ID NO 70
<211> LENGTH: 20
<212> TYPE: DNA
<213> ORGANISM: Mus musculus

<400> SEQUENCE: 70
gcccaatgct aactgagagc                                              20

<210> SEQ ID NO 71
```

```
<211> LENGTH: 20
<212> TYPE: DNA
<213> ORGANISM: Homo sapiens

<400> SEQUENCE: 71
agccctccct ggtttagtgt                                                   20

<210> SEQ ID NO 72
<211> LENGTH: 22
<212> TYPE: DNA
<213> ORGANISM: Mus musculus

<400> SEQUENCE: 72
aaattcctca gagtgaggct tg                                                22

<210> SEQ ID NO 73
<211> LENGTH: 20
<212> TYPE: DNA
<213> ORGANISM: Homo sapiens

<400> SEQUENCE: 73
ttgttcttgt tgctgcttgg                                                   20

<210> SEQ ID NO 74
<211> LENGTH: 21
<212> TYPE: DNA
<213> ORGANISM: Mus musculus

<400> SEQUENCE: 74
ccagaaggct tcggacaagt c                                                 21

<210> SEQ ID NO 75
<211> LENGTH: 20
<212> TYPE: DNA
<213> ORGANISM: Homo sapiens

<400> SEQUENCE: 75
tcacaggtgg agttttccag                                                   20

<210> SEQ ID NO 76
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 76
taaagagccc tccatcttgc                                                   20

<210> SEQ ID NO 77
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 77
tcaagatgcg tggatatctc gg                                                22

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 78
ggaattgaga aagggcacaa                                              20

<210> SEQ ID NO 79
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 79
aaggactcca aagtaacaat tca                                          23

<210> SEQ ID NO 80
<211> LENGTH: 25
<212> TYPE: DNA
<213> ORGANISM: Homo sapiens

<400> SEQUENCE: 80
atttggagcc tcttatagct gtttg                                        25

<210> SEQ ID NO 81
<211> LENGTH: 20
<212> TYPE: DNA
<213> ORGANISM: Mus musculus

<400> SEQUENCE: 81
ggcaagcttt gctttagtgc                                              20

<210> SEQ ID NO 82
<211> LENGTH: 20
<212> TYPE: DNA
<213> ORGANISM: Homo sapiens

<400> SEQUENCE: 82
ctctgcttcc tgggttcaag                                              20

<210> SEQ ID NO 83
<211> LENGTH: 18
<212> TYPE: DNA
<213> ORGANISM: Mus musculus

<400> SEQUENCE: 83
cgcagaatct tccaccct                                                18

<210> SEQ ID NO 84
<211> LENGTH: 20
<212> TYPE: DNA
<213> ORGANISM: Homo sapiens

<400> SEQUENCE: 84
cgatggctat gaagggaaaa                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 85
ccgatctgtg caggagaccg                                              20

```
<210> SEQ ID NO 86
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 86
gacccgggag acggtcagca                                                  20

<210> SEQ ID NO 87
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 87
tgagcatccc acccccta                                                    19

<210> SEQ ID NO 88
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 88
attgggaact tggggtggag gc                                               22

<210> SEQ ID NO 89
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 89
atgcccactc cgtcagcg                                                    18

<210> SEQ ID NO 90
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 90
cttcaagcag agcacaaagc                                                  20

<210> SEQ ID NO 91
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 91
tggggtcctc ggagctctcg ggct                                             24

<210> SEQ ID NO 92
<211> LENGTH: 23
<212> TYPE: DNA
<213> ORGANISM: Artificial Sequence
<220> FEATURE:
<223> OTHER INFORMATION: Synthetic Polynucleotide
```

<400> SEQUENCE: 92
agctctcggg ctcaggtgga ggt                                          23

<210> SEQ ID NO 93
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 93
ccaaacatca gcgtcagtat ag                                           22

<210> SEQ ID NO 94
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 94
ggcacacggt atgagaaaag attg                                         24

<210> SEQ ID NO 95
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 95
gctcatcctt gtgaactttg                                              20

<210> SEQ ID NO 96
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 96
gtggcacacg aaaggtttct c                                            21

<210> SEQ ID NO 97
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 97
agagcattac aattcaaggc tc                                           22

<210> SEQ ID NO 98
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 98
gatgccaacg acacgtctga                                              20

<210> SEQ ID NO 99

```
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 99
tgtgagggag atgctcagtg                                                    20

<210> SEQ ID NO 100
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 100
taaaggtcca ataagatgtc agaa                                               24

<210> SEQ ID NO 101
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 101
gtgctcctgc ctcaagaaga a                                                  21

<210> SEQ ID NO 102
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 102
ggagagaaac cacggaagaa                                                    20

<210> SEQ ID NO 103
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 103
gcactcttca ctcctctaaa tccag                                              25

<210> SEQ ID NO 104
<211> LENGTH: 23
<212> TYPE: DNA
<213> ORGANISM: Mus musculus

<400> SEQUENCE: 104
cttgggcctg gatcttgggg atc                                                23

<210> SEQ ID NO 105
<211> LENGTH: 20
<212> TYPE: DNA
<213> ORGANISM: Mus musculus

<400> SEQUENCE: 105
gggaacttcc tgactagggg                                                    20
```

```
<210> SEQ ID NO 106
<211> LENGTH: 20
<212> TYPE: DNA
<213> ORGANISM: Mus musculus

<400> SEQUENCE: 106
agcgcacgag gcggaacaaa                                                    20

<210> SEQ ID NO 107
<211> LENGTH: 20
<212> TYPE: DNA
<213> ORGANISM: Mus musculus

<400> SEQUENCE: 107
aaaagccaga ggtgcaagaa                                                    20

<210> SEQ ID NO 108
<211> LENGTH: 30
<212> TYPE: DNA
<213> ORGANISM: Mus musculus

<400> SEQUENCE: 108
ttgtctagag agcatggagg gccatgtcaa                                         30

<210> SEQ ID NO 109
<211> LENGTH: 20
<212> TYPE: DNA
<213> ORGANISM: Mus musculus

<400> SEQUENCE: 109
gggccagttg tgtgacttgg                                                    20

<210> SEQ ID NO 110
<211> LENGTH: 20
<212> TYPE: DNA
<213> ORGANISM: Mus musculus

<400> SEQUENCE: 110
gggccagttg tgtgacttgg                                                    20

<210> SEQ ID NO 111
<211> LENGTH: 20
<212> TYPE: DNA
<213> ORGANISM: Mus musculus

<400> SEQUENCE: 111
agagagccgc tgtgaggcgt                                                    20

<210> SEQ ID NO 112
<211> LENGTH: 20
<212> TYPE: DNA
<213> ORGANISM: Mus musculus

<400> SEQUENCE: 112
tatgatcgga attcctcgac                                                    20

<210> SEQ ID NO 113
<211> LENGTH: 30
<212> TYPE: DNA
<213> ORGANISM: Mus musculus
```

```
<400> SEQUENCE: 113
ccactcctct gtgacacttt agccctccga                                          30

<210> SEQ ID NO 114
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 114
tccgcctcct cctctgct                                                       18

<210> SEQ ID NO 115
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 115
gggaatttat tgatttgcat                                                     20

<210> SEQ ID NO 116
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 116
ccggccaaaa ttgatgcttt cc                                                  22

<210> SEQ ID NO 117
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 117
cagtcccaaa agcatcattg acat                                                24

<210> SEQ ID NO 118
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 118
cactgtccaa actagg                                                         16

<210> SEQ ID NO 119
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 119
cactgtccac actagg                                                         16
```

COMPOSITIONS AND METHODS FOR XI CHROMOSOME REACTIVATION

RELATED APPLICATIONS

This application is a National Stage Application of PCT/US2016/027840, filed Apr. 15, 2016, entitled "COMPOSITIONS AND METHODS FOR XI CHROMOSOME REACTIVATION", which claims the benefit under 35 U.S.C. § 119(e) of U.S. Provisional Application Ser. No. 62/148,106, entitled "COMPOSITIONS AND METHODS FOR XI CHROMOSOME REACTIVATION", filed Apr. 15, 2015, the entire contents of each application which are incorporated herein by reference.

FEDERALLY SPONSORED RESEARCH

This invention was made with government support under grant number GM033977 awarded by the National Institutes of Health. The government has certain rights in the invention.

FIELD OF THE DISCLOSURE

The invention relates to methods for reactivating mammalian inactive X chromosomes through genetic and pharmacological means.

BACKGROUND OF THE DISCLOSURE

X chromosome inactivation (XCI), the random transcriptional silencing of one X chromosome in somatic cells of female mammals, is a mechanism that ensures equal expression of X-linked genes in both sexes. XCI is initiated by Xist, a 17-kb non-coding RNA whose expression during early embryogenesis is both necessary and sufficient for silencing. Xist represses transcription in cis by coating only the X chromosome from which it is produced. Once Xist has been upregulated during early development or differentiation, it continues to be expressed from the inactive X (Xi) even in fully differentiated somatic cells. Prior to the initiation of XCI, Tsix, an antisense repressor of Xist, blocks Xist upregulation on the future active X chromosome (Xa).

An understanding of the factors and mechanisms involved in XCI is directly relevant to certain human diseases (e.g., dominant X-linked diseases). For example, loss-of-function mutations in the X-linked methyl-CpG binding protein 2 (MECP2) gene lead to the neurodevelopmental disorder Rett syndrome (RTT). Most RTT patients are females who are heterozygous for MECP2 deficiency due to random XCI. Therapeutic options for the treatment of dominant X-linked diseases, such as Rett syndrome, remain limited. Accordingly, there is a need for new compositions and methods of treatment for dominant X-linked diseases.

SUMMARY OF THE DISCLOSURE

The instant disclosure relates to methods and compositions for the reactivation of inactive X (Xi) chromosomes. In some aspects, the methods and compositions described herein may be useful for the treatment of dominant X-linked diseases, such as Rett syndrome. The disclosure is based, in part, on the discovery that inhibition of X chromosome inactivating factors (XCIFs) can mediate reactivation of inactive X chromosomes, re-expression of Xi-linked genes and/or reduce expression or activity of the Xist.

Accordingly, in some aspects, the disclosure provides a method of inducing expression of an X-linked gene in a cell having an inactive X chromosome, the method comprising delivering to the cell an X chromosome inactivation factor (XCIF) inhibitor in an amount effective for inducing expression of the X-linked gene.

In some aspects, the disclosure provides a method of treating a subject having a dominant X-linked disease, the method comprising administering to the subject an X chromosome inactivation factor (XCIF) inhibitor in an amount effective for inducing expression a target X-linked gene. In some embodiments, the dominant X-linked disease results from a mutated allele of the X-linked gene, and wherein the inhibitor is administered in an amount effective for inducing expression of a wild-type allele of the X-linked gene.

In some embodiments, the cell is of a subject having a dominant X-linked disease resulting from a mutated allele of the X-linked gene. In some embodiments, the X-linked gene is MECP2. In some embodiments, the X-linked gene is MECP2 and the X-linked disease is Rett Syndrome.

In some embodiments, the dominant X-linked disease is selected from the group consisting of: X-linked hypophosphatemia, incontinentia pigmenti type 2, Aicardi syndrome, CDK5L syndrome, focal dermal hypoplasia, CHILD syndrome, Lujan-Fryns syndrome, orofaciodigital syndrome 1, hereditary nephritis (Alport syndrome), Giuffre-Tsukahara syndrome, Goltz syndrome, Fragile X syndrome, Bazex-Dupre-Christol syndrome, Charcot-Marie-Tooth disease, chondrodysplasia punctate, erythropoietic protoporphyria, scapuloperoneal myopathy, and craniofrontonasal dysplasia.

In some embodiments, the XCIF inhibitor selectively inhibits activity of an X chromosome inactivation factor selected from the group consisting of: ACVR1, AURKA, DNMT1, FBXO8, LAYN, NF1, PDPK1, PYGO1, RNF165, SGK1/2, SOX5, STC1, ZNF426 and C17orf98. In some embodiments, the X chromosome inactivation factor is PI3K and the XCIF inhibitor is GNE-317 or LY29400. In some embodiments, the X chromosome inactivation factor is PDPK1 and the XCIF inhibitor is OSU-03012 or BX912. In some embodiments, the X chromosome inactivation factor is AURKA and the XCIF inhibitor is VX680, CD532, or MLN8237. In some embodiments, the X chromosome inactivation factor is SGK1/2 and the XCIF inhibitor is GSK650394. In some embodiments, the X chromosome inactivation factor is ACVR1 and the XCIF inhibitor is dorsomorphin, K02288 or LDN193189.

In some embodiments, the XCIF inhibitor selectively inhibits activity of mammalian target of rapamycin (mTOR). In some embodiments, the XCIF inhibitor is rapamycin, KU-0063794, or everolimus.

In some embodiments, the XCIF inhibitor is an inhibitory oligonucleotide having a region of complementarity that is complementary with at least 8 nucleotides of an mRNA encoded by an XCIF gene. In some embodiments, the inhibitory oligonucleotide is selected from the group consisting of: antisense oligonucleotide, siRNA, shRNA and miRNA. In some embodiments, the inhibitory oligonucleotide is a modified inhibitory oligonucleotide. In some embodiments, the modified inhibitory oligonucleotide comprises a bridged nucleotide (e.g., a locked nucleic acid (LNA)), phosphorothioate backbone, and/or a 2'-OMe modification.

In some embodiments, the method further comprises determining that cell has a mutant allele of the X-linked gene. In some embodiments, the method further comprises determining that delivery of the XCIF inhibitor to the cell results in induced expression of the X-linked gene. In some embodiments, the method further comprises determining that delivery of the inhibitor to the cell results in induced expression of a wild-type allele of the X-linked gene. In some embodiments, the method further comprises determining that delivery of the XCIF inhibitor to the cell results in reactivation of an X chromosome. In some embodiments, the method further comprises determining that delivery of the XCIF inhibitor to the cell results in decreased expression or activity of XIST. In some embodiments, the cell is in vitro. In some embodiments, the cell is in a subject.

BRIEF DESCRIPTION OF THE DRAWINGS

FIG. 1A shows a schematic summary of the shRNA screen. The Xi is designated as such due to deletion of Xist on the Xa. FIG. 1B shows H4SV cells expressing an shRNA against one of the 13 candidates or, as a control, a non-silencing (NS) shRNA were FACS sorted and GFP-positive cells isolated. For each KD cell line, the percent GFP-positive cells was expressed as the fold increase relative to that obtained with the NS shRNA, which was set to 1. FIG. 1C shows two-color RNA FISH monitoring expression of G6pdx and Lamp2 (left) and Pgk1 and Mecp2 (right) in each of the 13 XCIF KD BMSL2 cell lines. DAPI staining is shown in blue. The experiment was performed at least twice, and representative images are shown (top) and the results quantified (bottom) from one experiment.

FIG. 2A shows two-color RNA FISH monitoring expression of G6pdx and Lamp2 (left) and Pgk1 and Mecp2 (right) in the 13 XCIF KD ES cell lines following differentiation. DAPI staining is also shown. Representative images are shown (top) and the results quantified (bottom). FIG. 2B shows percentage of alkaline phosphatase-negative single cells in the 13 XCIF KD ES cell lines before (top, undifferentiated) and after (bottom, differentiated) treatment with RA. FIG. 2C shows qRT-PCR analysis monitoring expression of Oct4 in the 13 XCIF KD ES cell lines following treatment with RA. As a control, expression of Oct4 in undifferentiated ES cells is shown and was set to 1. Error bars indicate SD. FIG. 2D shows qRT-PCR analysis of XCIFs in undifferentiated and differentiated mouse ES cells. Expression in differentiated ES cells was normalized to that observed in undifferentiated cells, which was set to 1. Error bars indicate SD.

FIG. 3A shows qRT-PCR analysis monitoring Xist expression in the 13 XCIF KD ES cell lines following differentiation. Expression in differentiated ES cells was normalized to that obtained with the NS shRNA, which was set to 1. Error bars indicate SE. FIG. 3B shows RNA FISH monitoring localization of Xist in the 13 XCIF KD ES cell lines following differentiation. Cells were categorized as having either a typical Xist cloud or "other" pattern, which includes either the lack of a detectable Xist signal or presence of two small Xist signals, as in undifferentiated ES cells. FIG. 3C shows RNA FISH monitoring expression of Xist (top) and Mecp2 (bottom) in BMSL2 cells treated with an Xist locked nucleic acid antisense oligonucleotide (LNA ASO) or a control LNA ASO. FIG. 3D shows ChIP analysis monitoring binding of DNMT1 and POL2 to the Xist promoter and exon 2 in BMSL2 cells expressing a NS or Dnmt1 shRNA. Error bars indicate SD. FIG. 3E shows nuclear run-on assay monitoring transcription of Xist, Hprt and Tbp in BMSL2 cells expressing a NS or DNMT1 shRNA. FIG. 3F shows qRT-PCR analysis monitoring Xist levels in BMSL2 cells expressing a NS or Dnmt1 shRNA following treatment with actinomycin D. Actin mRNA was used as a normalization control. Error bars indicate SD. FIG. 3G shows qRT-PCR analysis monitoring Xist expression in MEFs isolated from female Dnmt1+/+ and Dnmt1−/− embryos. Four different litters were analyzed (n=4 mice total per genotype), and the results were averaged. Expression was normalized to that observed in Dnmt1+/+ MEFs, which was set to 1. Error bars indicate SD.*P<0.001 (Student's t-test). FIG. 3H shows qRT-PCR monitoring levels of Xist and Tsix in H4SV cells expressing a NS or DNMT1 shRNA. Expression was normalized to that obtained with the NS shRNA, which was set to 1. Error bars indicate SD. FIG. 3I shows qRT-PCR analysis monitoring Hprt and Xist expression in BMSL2 cells treated in the absence or presence of 5-AZA. Expression was normalized to that observed in the absence of 5-AZA, which was set to 1. Error bars indicate SD.

FIGS. 4A-4I show reactivation of the Xi-linked Mecp2 gene by small molecule XCIF inhibitors. FIGS. 4A-4B show two-color RNA FISH monitoring expression of Xist and Mecp2 in differentiated mouse ES cells treated with DMSO (control or -), OSU-03012 or LY294002 (FIG. 4A), and in BMSL2 cells treated with DMSO or GNE-317 (FIG. 4B). Representative images are shown (top) using the higher concentrations of the inhibitors, and the results quantified (bottom). Yellow arrowheads indicate co-localizing Xist and Mecp2 signals; white arrowheads indicate Mecp2 signals not co-localizing with Xist. FIG. 4C shows two-color RNA FISH monitoring Xist and Mecp2 expression in mouse cortical neurons treated with DMSO (control or -), OSU-03012, BX912 or LY294002. Representative images are shown (top) and the results quantified (bottom). Arrowheads indicate Mecp2 signals. FIG. 4D shows two-color RNA FISH monitoring expression of Xist and Mecp2 in mouse BMSL2 fibroblasts treated with DMSO (control or -) or GSK650394. Representative images are shown (top) and the results quantified (bottom). Arrowheads indicate Mecp2 signals. FIG. 4E shows qRT-PCR monitoring expression of Xist (left) and Mecp2 (right) in BMSL2 cells treated with DMSO or increasing concentrations of GSK650394 (2.5, 5 or 10 µM). FIG. 4F shows two-color RNA FISH monitoring expression of Xist and Mecp2 in BMSL2 cells treated with DMSO or K02288. Representative images are shown (top) and the results quantified (bottom). Arrowheads indicate Mecp2 signals. FIG. 4G shows qRT-PCR monitoring expression of Xist (left) and Mecp2 (right) in BMSL2 cells treated with DMSO, K02288 (0.5 µM) or LDN193189 (0.5 µM). FIG. 4H shows Two-color RNA FISH monitoring Xist and Mecp2 expression in BMSL2 cells treated with DMSO (control or -), LY294002 or OSU-03012, and at least 6 days following removal of the inhibitor. Representative images are shown (top) and the results quantified (bottom). Arrowheads indicate Mecp2 signals. FIG. 4I shows qRT-PCR monitoring Xi-linked wild-type MECP2 expression in human RTT fibroblasts treated with DMSO (−), 5-azacytidine (5-AZA), BX912, OSU-03012 or VX680. As a control, Xa-linked wild-type MECP2 expression was monitored in another clonal fibroblast cell line derived from the same RTT patient (lane 1). The arrowhead indicates the wild-type MECP2 qRT-PCR product. GAPDH was monitored as a loading control. Bottom, schematic of the MECP2 wild-type (wt) and mutant (mut) alleles.

FIG. 5A shows two-color RNA FISH monitoring expression of G6pdx and Lamp2 (top) and Pgk1 and Mecp2 (bottom) in female Stc1+/+ and Stc1−/− MEFs, and as a control male Stc1−/− MEFs. Representative images are shown (top) and the results quantified (bottom). FIG. 5B shows qRT-PCR analysis monitoring Xist expression in MEFs isolated from female Stc1+/+ and Stc1−/− embryos. Four different litters were analyzed (n=4 mice total per genotype), and the results were averaged. Expression was normalized to that of the ribosomal gene RPM, and Xist expression in Stc1+/+ MEFs was set to 1. Error bars indicate SD. *P<0.001 (Student's t-test).

FIG. 6A shows a schematic of the RNA-Seq analysis pipeline. FIG. 6B shows 6istribution of log 2 transformed ratio of X-linked gene expression in MEFs from female Stc1−/− (KO) and Stc1+/+(WT) embryos (n=3 per genotype). FIG. 6C shows a box plot of X-linked gene expression (log 2 transformed FPKM) in MEFs from female Stc1−/− and Stc1+/+ embryos (n=3 per genotype). Boxed areas span the first to the third quartile. Whiskers represent $15^{th}$ and $85^{th}$ percentiles. FIG. 6D shows qRT-PCR analysis monitoring expression of Mecp2 and Hprt in MEFs from 2 different litters of female Stc1−/− and Stc1+/+ embryos (n=2 mice total per genotype). The results were normalized to those obtained in Stc1+/+ MEFs, which was set to 1. Error bars indicate SE. FIG. 6E shows an immunoblot showing MECP2 and STC1 levels in female Stc1+/+ and Stc1−/− MEFs (left) or brain tissue female Stc1+/+ and Stc1−/− P1 mice (right) (n=3 per genotype). α-tubulin (TUBA) was monitored as a loading control. FIG. 6F shows qRT-PCR analysis of Stc1, Xist, Mecp2 and Hprt expression in BMSL2 cells expressing a NS or STC1 shRNA. The results were normalized to those obtained with the NS shRNA, which was set to 1. Error bars indicate SE. FIG. 6G shows an immunoblot showing MECP2 and STC1 levels in BMSL2 cells expressing a NS or Stc1 shRNA.

FIG. 7A shows bright field images showing growth of the 13 XCIF KD H4SV cell lines following selection in HAT medium. FIG. 7B shows qRT-PCR analysis monitoring target gene expression in the 13 XCIF KD H4SV cell lines expressing the shRNA identified in the primary screen. For each gene, knockdown efficiency was determined relative to the level of target gene expression in the control cell line expressing a non-silencing (NS) shRNA, which was set to 1. Error bars indicate SD. FIG. 7C shows bright field images showing growth of the 13 XCIF KD H4SV cell lines, expressing a second, unrelated shRNA to that shown in FIG. 7A, following selection in HAT medium. FIG. 7D shows qRT-PCR analysis monitoring target gene expression in the 13 XCIF KD H4SV cell lines expressing a second, unrelated shRNA to that shown in FIG. 7B. Error bars indicate SD.

FIG. 8A shows representative two-color RNA FISH images showing expression of G6pdx and Lamp2 (top) and Pgk1 and Mecp2 (bottom) in each of the 13 XCIF KD BMSL2 cell lines. DAPI staining is also shown. FIG. 8B shows that in BMSL2 cells the Xi and Xa encode two distinguishable Pgk1 alleles, Pgk1a and Pgk1b, respectively, which differ by a single nucleotide polymorphism within the mRNA. Allele-specific expression of the Xi- and Xa-linked Pgk1 genes in each of the 13 XCIF KD BMSL2 cell lines was analyzed using a single nucleotide primer-extension (SNuPE) assay. The ratio of Pgk1a:Pgk1b expression was calculated and normalized to that obtained with the NS shRNA, which was set to 1. The results show that in each of the 13 XCIF KD BMSL2 cell lines the ratio of Pgk1a to Pgk1b was increased, indicating that knockdown of each of the 13 XCIFs reactivated the Xi-linked Pgk-1a gene. FIG. 8C shows that in BMSL2 cells the Xi and Xa encode two distinguishable Pgk1 alleles, Pgk1a and Pgk1b, respectively, which differ by a single nucleotide polymorphism within the mRNA. Allele-specific expression of the Xi- and Xa-linked Pgk1 genes in six representative XCIF KD BMSL2 cell lines was analyzed using a single nucleotide primer extension (SNuPE) assay. The data are plotted as the function of ΔRn for each sample, which represents the reporter fluorescence for each allele (VIC/FAM) normalized to the passive dye. The results show that in each of the six XCIF KD BMSL2 cell lines the Xi-linked Pgk1a gene was reactivated. FIG. 7D shows X chromosome painting experiments in the 13 XCIF KD BMSL2 cell lines. The results show that the X chromosome content of the XCIF KD BMSL2 cell lines was similar to that of the control BMSL2 cell line expressing a NS shRNA. Thus, the substantially increased bi-allelic expression of X-linked genes observed by RNA FISH in the XCIF KD cell lines cannot be explained by differences in X chromosome number.

FIG. 9A shoes representative two-color RNA FISH images monitoring expression of G6pdx and Lamp2 (top) and Pgk1 and Mecp2 (bottom) in the 13 XCIF KD ES cell lines following differentiation. DAPI staining is also shown. FIG. 9B shows X chromosome painting experiments in the 13 XCIF KD ES cell lines following differentiation. FIG. 9C shows qRT-PCR analysis monitoring expression of Eomes, Tcf7l2 and Cdx2 in the 13 XCIF KD ES cell lines following treatment with RA. As a control, expression of each gene in undifferentiated ES cells is shown and was set to 1. Error bars indicate SD.

FIG. 10A shows RNA FISH images. In each of the 13 XCIF KD ES cell lines following differentiation, the majority of cells that lost the typical Xist localization pattern lacked a detectable Xist signal (see FIG. 3B). However, some cells that had lost the typical Xist localization pattern contained two small Xist signals, reminiscent of undifferentiated ES cells. Examples of this latter localization pattern are shown here. Nuclear signals are indicated in red and denoted by arrowheads; DAPI staining is also shown. FIG. 10B shows qRT-PCR analysis monitoring expression of Xist (left), Tsix (middle) and Dnmt1 (right) in H4SV cells expressing a NS or one of two Dnmt1 shRNAs (Dnmt1-1 or Dnmt1-2). For Xist and Tsix expression, a second, unrelated Dnmt1 shRNA to that used in FIG. 3H. Expression was normalized to that obtained with the control NS shRNA, which was set to 1. Error bars indicate SD. FIG. 10C shows qRT-PCR analysis monitoring expression of Xist (left), Tsix (middle) and Dnmt1 (right) in differentiated ES cells expressing a NS shRNA or one of two Dnmt1 shRNAs (Dnmt1-1 or Dnmt1-2). Expression was normalized to that obtained with the control NS shRNA, which was set to 1. Error bars indicate SD.

FIGS. 11A-11C show additional RNA FISH images related to FIGS. 4A-4E. FIG. 11A and FIG. 11B show two-color RNA FISH monitoring expression of Xist and Mecp2 in differentiated ES cells treated with DMSO (control), OSU-03012 (4 μM) or LY294002 (10 μM) (FIG. 11A), and in BMSL2 cells treated with DMSO or GNE-317 (5 μM) (FIG. 11B). Yellow boxes indicate cells with co-localizing Xist and Mecp2 signals; white boxes indicate cells with biallelic expression of Mecp2 and complete loss of the Xist signal. FIG. 11C shows two-color RNA FISH monitoring Xist and Mecp2 expression in BMSL2 cells treated with DMSO (control), OSU-03012 (2.5 µM) or LY294002 (8 µM), and at least 6 days following removal of the inhibitor. White boxes indicate cells with biallelic expression of Mecp2.

FIG. 12A shows X chromosome painting experiments in female Stc1+/+ and Stc1-/- MEFs. The results show that the X chromosome content of Stc1-/- MEFs was similar to that of Stc1+/+ MEFs. Thus, the substantially increased bi-allelic expression of X-linked genes observed by RNA FISH in the Stc1-/- MEFs cannot be explained by differences in X chromosome number. FIG. 12B shows defective XCI in cortical neurons from brain sections of female Stc1-/- mice. Two-color RNA FISH monitoring expression of Xist and Mecp2 or G6pdx in cortical neurons from adjacent 5-µm brain sections of female Stc1-/- and Stc1+/+ mice (n=3 per genotype, stage P1). Boxed regions denote cells with two Mecp2 or G6pdx signals; yellow boxes indicate cells with co-localizing Xist and Mecp2/G6pdx signals. All cells in the regions shown represent neurons that, based on anatomical landmarks, are present in post-hybridized sections.

FIGS. 13A-13E show additional experiments and data analyses related to FIGS. 6A-6G. FIG. 13A shows a volcano plot showing distribution of log 2 transformed ratio of X-linked gene expression in MEFs isolated from Stc1-/- (KO) and Stc1+/+(WT) embryos (n=3 per genotype). The genes are plotted against negative transformed log of P value. Red circles represent genes with a >2-fold change in expression and P<0.01. The results show that the similarity of X-linked gene expression between female Stc1+/+ and Stc1-/- MEFs was statistically significant. FIG. 13B shows box plots displaying changes in autosomal gene expression (log 2 transformed FPKM) in Stc1-/- and Stc1+/+ MEFs. Boxed areas span the first to the third quartile. Whiskers represent $15^{th}$ and $85^{th}$ percentiles; samples falling outside these percentiles are shown as circles. FIG. 13C shows XCIFs are not generally required for repression of imprinted genes. Primary female mouse embryonic fibroblasts from the strain C57BL/6 (CAST7), which contains chromosome 7 from *Mus castaneus* (Cast), were transduced with shRNAs against each of the XCIFs and analyzed for allele-specific expression of four genes located on chromosome 7 that are either paternally expressed, (Kcnq1ot1 and Peg3) or maternally expressed (Ascl2 and Zim1). Expression of the two alleles can be distinguished by allele-specific restriction enzyme digestion following gene-specific RT-PCR. The sizes of the undigested and digested bands are indicated, and the sizes of the predicted digested fragments are shown in the table (bottom). If knockdown of an XCIF results in reactivation of the normally silenced allele, a mixture of the maternal and paternal allele-specific digestion patterns would be observed. The results show that in all 13 XCIF KD cell lines, all four genes displayed only the expected allele-specific expression pattern, indicating that the XCIFs are not generally required for repression of the imprinted genes. FIG. 13D shows involvement of Polycomb subunits EZH2 and BMI1 for repression of the X-linked Hprt gene. (Left) qRT-PCR analysis monitoring Hprt expression in BMSL2 cells expressing an Ezh2 or Bmi1 shRNA or, as a control, a NS shRNA. (Right) qRT-PCR analysis confirming target gene knockdown in mouse ES cells expressing an Ezh2 (left) or Bmi1 (right) shRNA. Error bars indicate SD. FIG. 13E shows analysis of available datasets from Yildirim et al. 2013 showing the distribution of log 2 transformed ratio of X-linked gene expression in hematopoietic cells from female heterozygous (HET) Xist mutant mice and wild-type (WT) mice. The data were downloaded from Gene Expression Omnibus (GSE43961), normalized by RMA and filtered by detection above background (DABG) (cutoff P-value <0.0001) using Bioconductor package xps. The percentage of X-linked genes upregulated >1.5-fold is shown.

DETAILED DESCRIPTION

Figures 1A, 1B:
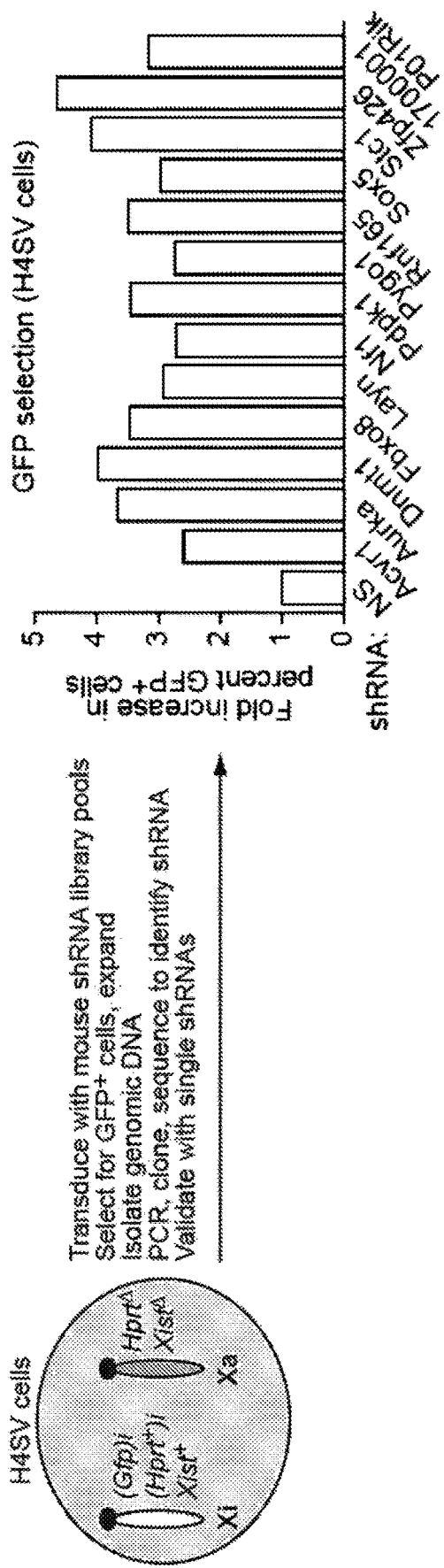
FIGS. 1A-1C show identification of factors involved in mammalian XCI.

Aspects of the disclosure relate to the biological and pharmacological inhibition or reversal of X chromosome inactivation. The disclosure is based, in part, on the discovery that inhibition of X chromosome inactivating factors (XCIFs) can mediate reactivation of inactive X chromosomes, re-expression of X-linked genes and/or reduce expression or activity of Xist.

In some aspects, the disclosure relates to a method of inducing expression of an X-linked gene in a cell having an inactive X chromosome, the method comprising delivering to the cell an X chromosome inactivation factor (XCIF) inhibitor in an amount effective for inducing expression of the X-linked gene. As used herein, the term "X chromosome inactivation factor" refers to a gene or gene product (e.g., a protein) that are required for or involved in maintenance or establishment of X chromosome inactivation. In some embodiments, inhibition of XCIF expression and/or activity leads to reactivation of an inactivated X chromosome or one or more genes residing thereon (Xi-linked genes). Thirteen X chromosome inactivation factors (XCIFs) have been identified herein (Table 1), and are indicated as being involved in diverse processes including cell signaling (ACVR1, AURKA, NF1, LAYN and PDPK1), cell metabolism (STC1), ubiquitin-dependent regulation (FBXO8 and RNF165) and transcription (PYGO1, SOX5 and ZNF426), for example, as disclosed in Bhatnagar et al., 2014, Proc Natl Acad Sci USA 111:12591-12598.

XCIF Inhibitors

The disclosure relates in part to a discovery of inhibitors of XCIFs that can reactivate expression of the Xi-linked genes. Inhibitors of XCIFs can be peptides, proteins, antibodies, small molecules, or nucleic acids. In some embodiments, an XCIF inhibitor selectively inhibits activity of an X chromosome inactivation factor selected from the group consisting of: ACVR1, AURKA, DNMT1, FBXO8, LAYN, NF1, PIK3, PDPK1, PYGO1, RNF165, SOX5, STC1, ZNF426 and C17orf98.

Aspects of the disclosure relate to inhibition of Activin Receptor Type 1 (ACVR1), an XCIF that encodes a receptor serine-threonine kinase (also known as ALK2) that mediates signaling by bone morphogenic proteins (BMPs). Gain-of-function mutations in ACVR1 result in the autosomal dominant disease fibrodysplasia ossificans progressiva (FOP) and have been found in the childhood malignancy diffuse intrinsic pontine glioma (DIPG). Several small molecule ACVR1 inhibitors are available, including K02288 and LDN193189. K02288 is a potent and selective inhibitor of BMP type 1 receptor signaling; strongly inhibiting ACVR1/ALK2, ALK1, and ALK6, and weakly inhibiting the other ALKs and ActRIIA. LDN 193189 is a selective BMP signally inhibitor that inhibits the transcriptional activity of the BMP type I receptors ACVR1/ALK2 and ALK3; it also exhibits 200-fold selectivity for BMP versus TGF-β. Further examples of ACVR1 inhibitors include LDN19318, DMH-1, ML-347, BML-275, dorsomorphin, and LDN-212854.

Aspects of the disclosure relate to inhibition of Aurora Kinase A (AURKA). In some embodiments, AURKA inhibitors are small molecules. Examples of AURKA inhibitors include but are not limited to VX-680, MLN8237, TAS-119, MLN8054, PF-03814735, SNS-314, BI 811283, AMG 900, AZD1152, AS703569, R763, PHA-739358, CD532, and MK-0457. In some embodiments, the X chromosome inactivation factor is AURKA and the XCIF inhibitor is VX680. In some embodiments, the X chromosome inactivation factor is AURKA and the XCIF inhibitor is CD532 or MLN8237.

Aspects of the disclosure relate to inhibition of DNA (cytosine-5)-methyltransferase 1 (DNMT1). In some embodiments, DNMT1 inhibitors are small molecules. Examples of DNMT1 inhibitors include but are not limited to azacitadine, fazarabine, decitabine, sinefungin, psammaplin A, disulfiram, zebularine, and SGI-1027.

Aspects of the disclosure relate to the inhibition of PI3K/Akt signaling to reactivate Xi-linked genes. In some embodiments, PI3K inhibitors are small molecules. Examples of PI3K inhibitors include but are not limited to GNE317, LY294002, Wortmannin, demethoxyviridin, BEZ235, BGT226, BKM120, BYL719, XL765, XL147, GDC-0941, SF1126, GSK1059615, PX-866, CAL-101, BAY80-6946, GDC-0032, IPI-145, VS-5584, ZSTK474, SAR245409, and RP6530. In some embodiments, the XCIF is PI3K and the XCIF inhibitor is GNE-317 or LY29400.

Aspects of the disclosure relate to inhibition of 3-phosphoinositide-dependent protein kinase 1 (PDPK1). In some embodiments, PDPK1 inhibitors are small molecules. Examples of PDPK1 inhibitors include but are not limited to OSU-03012, BAG-956, BX-795, GSK-2334470, BX-912, and PHT-427. In some embodiments, the XCIF is PDPK1 and the XCIF inhibitor is OSU-03012 or BX912.

The serum and glucocorticoid kinase (SGK) family of serine/threonine kinases includes three distinct but highly homologous isoforms (SGK1, SGK2, and SGK3) that share a similar domain structure. All three are activated by PDPK1 and have been implicated in a wide variety of cellular processes and small molecule inhibitors with selectivity for SGKs over AKTs have been developed. Examples of SGK1/2 inhibitors include GSK-650394 and EMD638683.

In some embodiments, an XCIF inhibitor targets a downstream substrate of PDPK1. Examples of downstream substrates to PDPK1 include but are not limited to AKT (also known as protein kinase B), ribosomal protein S6 kinase beta-1 (S6K1), protein kinase C (PKC), ribosomal s6 kinase (e.g., $p70^{rsk}$, S6 Kinase), rho-associated, coiled-coil-containing protein kinase 1 (ROCK1), and mammalian target of rapamycin (mTOR). In some embodiments, an XCIF inhibitor targets mTOR. In some embodiments, an mTOR inhibitor is a small molecule. Examples of mTOR inhibitors include but are not limited to rapamycin, everolimus, sirolimus, temsirolimus, deforolimus, and KU-0063794.

In some embodiments, the term "small molecule" refers to a synthetic or naturally occurring chemical compound, for instance a peptide or oligonucleotide that may optionally be derivatized, natural product or any other low molecular weight (often less than about 5 kDalton) organic, bioinorganic or inorganic compound, of either natural or synthetic origin. Such small molecules may be a therapeutically deliverable substance or may be further derivatized to facilitate delivery.

As used herein the term "inhibitor" or "repressor" refers to any agent that inhibits, suppresses, represses, or decreases a specific activity, such as the activity of an X chromosome inactivation factors.

In some embodiments, an XCIF inhibitor when delivered to a cell reactivates an inactive X chromosome or one or more genes residing thereon. In some embodiments, delivery of an XCIF inhibitor to a cell results in an increase in the level of expression of an Xi-linked gene (a gene residing on the inactive X-chromosome) of at least 10%, 20%, 30%, 40%, 50%, 60%, 70%, 80%, 90%, 100%, 200% or 500% compared with the level of expression of the gene in a control cell that has not been delivered an XCIF inhibitor. In some embodiments, delivery of an XCIF inhibitor to a cell results in an increase in the level of expression of an Xi-linked gene (a gene residing in the inactive X-chromosome) in a range of 10% to 50%, 10% to 100%, 10% to 200%, 50% to 500% or more compared with the level of expression of the gene in a control cell that has not been delivered an XCIF inhibitor.

Inhibitory Oligonucleotides

In some embodiments, the XCIF inhibitor is an inhibitory oligonucleotide. Inhibitory oligonucleotides may interfere with gene expression, transcription and/or translation. Generally, inhibitory oligonucleotides bind to a target polynucleotide via a region of complementarity. For example, binding of inhibitory oligonucleotide to a target polynucleotide can trigger RNAi pathway-mediated degradation of the target polynucleotide (in the case of dsRNA, siRNA, shRNA, etc.), or can block the translational machinery (e.g., antisense oligonucleotides). In some embodiments, inhibitory oligonucleotides have a region of complementarity that is complementary with at least 8 nucleotides of an mRNA encoded by an XCIF gene. Inhibitory oligonucleotides can be single-stranded or double-stranded. In some embodiments, inhibitory oligonucleotides are DNA or RNA. In some embodiments, the inhibitory oligonucleotide is selected from the group consisting of: antisense oligonucleotide, siRNA, shRNA and miRNA. In some embodiments, inhibitory oligonucleotides are modified nucleic acids.

The term "nucleotide analog" or "altered nucleotide" or "modified nucleotide" refers to a non-standard nucleotide, including non-naturally occurring ribonucleotides or deoxyribonucleotides. In some embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438. A locked nucleic acid (LNA), often referred to as inaccessible RNA, is a modified RNA nucleotide. The ribose moiety of an LNA nucleotide is modified with an extra bridge connecting the 2' oxygen and 4' carbon.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro. In some embodiments, the inhibitory oligonucleotide is a modified inhibitory oligonucleotide. In some embodiments, the modified inhibitory oligonucleotide comprises a locked nucleic acid (LNA), phosphorothioate backbone, and/or a 2'-OMe modification.

Methods of Treatment

The disclosure relates, in some aspects, to methods useful for the treatment of certain diseases, such as dominant X-linked diseases. For example, loss-of-function mutations in the X-linked methyl-CpG binding protein 2 (MECP2) gene lead to the neurodevelopmental disorder Rett syndrome (RTT).

Accordingly, in some aspects, the disclosure provides a method of treating a subject having a dominant X-linked disease, the method comprising administering to the subject an X chromosome inactivation factor (XCIF) inhibitor in an amount effective for inducing expression a target X-linked gene.

Dominant X-linked diseases typically result from a mutated allele of the X-linked gene. The disclosure relates, in part, to XCIF inhibitors that are effective for inducing expression of a wild-type allele of the X-linked gene. Examples of X-linked diseases and their associated X-linked genes include Rett syndrome (MECP2), X-linked hypophosphatemia (PHEX), incontinentia pigmenti type 2 (IKBKG), Aicardi syndrome (de novo mutation of an X-linked gene), CDK5L syndrome (CDKL5), focal dermal hypoplasia (PORCN), CHILD syndrome (NSDHL), Lujan-Fryns syndrome (MED12), orofaciodigital syndrome 1 (OFD1), hereditary nephritis or Alport syndrome (COL4A3, COL4A4, COL4A5), Giuffre-Tsukahara syndrome (Xp22.13-q21.33), Goltz syndrome (PORCN), Fragile X syndrome (FMR1), Bazex-Dupre-Christol syndrome (Xq24-q27), Charcot-Marie-Tooth disease (GJB1), chondrodysplasia punctata (EBP), erythropoietic protoporphyria (ALAS2), scapuloperoneal myopathy (FLH1), and craniofrontonasal dysplasia (EFNB1).

As used herein, a "subject" is interchangeable with a "subject in need thereof", both of which may refer to a subject having a dominant X-linked disease, or a subject having an increased risk of developing such a disorder relative to the population at large. A subject in need thereof may be a subject having an inactive X chromosome. A subject can be a human, non-human primate, rat, mouse, cat, dog, or other mammal.

In some aspects, the disclosure provides a method of inducing expression of an X-linked gene in a cell having an inactive X chromosome, the method comprising delivering to the cell an X chromosome inactivation factor (XCIF) inhibitor in an amount effective for inducing expression of the X-linked gene. In some embodiments, the cell is in vitro. In some embodiments, the cell is in a subject.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with a dominant X-linked disease. Thus, the terms denote that a beneficial result has been conferred on a subject with a disorder (e.g., a dominant X-linked disease), or with the potential to develop such a disorder. Furthermore, the term "treatment" is defined as the application or administration of an agent (e.g., therapeutic agent or a therapeutic composition) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound in a pharmaceutically acceptable form that prevents and/or reduces the symptoms of a particular disease (e.g., a dominant X-linked disease). For example a therapeutic composition may be a pharmaceutical composition that prevents and/or reduces the symptoms of a dominant X-linked disease. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

Pharmaceutical Compositions

In some aspects, the disclosure relates to pharmaceutical compositions comprising an XCIF inhibitor. In some embodiments, the composition comprises an XCIF inhibitor and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described below. The active ingredients may be admixed or compounded with any conventional, pharmaceutically acceptable carrier or excipient. The compositions may be sterile.

Typically, pharmaceutical compositions are formulated for delivering an effective amount of an agent (e.g., an XCIF inhibitor). In general, an "effective amount" of an active agent refers to an amount sufficient to elicit the desired biological response (e.g., reactivation of the inactive X chromosome or one or more genes residing thereon. An effective amount of an agent may vary depending on such factors as the desired biological endpoint, the pharmacokinetics of the compound, the disease being treated (e.g., a dominant X-linked disease), the mode of administration, and the patient.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18th Ed. (1990).

It will be understood by those skilled in the art that any mode of administration, vehicle or carrier conventionally employed and which is inert with respect to the active agent may be utilized for preparing and administering the pharmaceutical compositions of the present disclosure. Illustrative of such methods, vehicles and carriers are those described, for example, in Remington's Pharmaceutical Sciences, 4th ed. (1970), the disclosure of which is incorporated herein by reference. Those skilled in the art, having been exposed to the principles of the disclosure, will experience no difficulty in determining suitable and appropriate vehicles, excipients and carriers or in compounding the active ingredients therewith to form the pharmaceutical compositions of the disclosure.

An effective amount, also referred to as a therapeutically effective amount, of a compound (for example, an antisense nucleic acid (e.g., oligonucleotide) or small molecule capable of inhibiting an XCIF) is an amount sufficient to ameliorate at least one adverse effect associated with expression, or reduced expression, of the gene in a cell or in an individual in need of such modulation. The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and selected mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

In some cases, compounds of the disclosure are prepared in a colloidal dispersion system. Colloidal dispersion systems include lipid-based systems including oil-in-water emulsions, micelles, mixed micelles, and liposomes. In some embodiments, a colloidal system of the disclosure is a liposome. Liposomes are artificial membrane vessels which are useful as a delivery vector in vivo or in vitro. It has been shown that large unilamellar vesicles (LUVs), which range in size from 0.2-4.0 μm can encapsulate large macromolecules. RNA, DNA and intact virions can be encapsulated within the aqueous interior and be delivered to cells in a biologically active form. Fraley et al. (1981) Trends Biochem Sci 6:77.

Liposomes may be targeted to a particular tissue by coupling the liposome to a specific ligand such as a monoclonal antibody, sugar, glycolipid, or protein. Ligands which may be useful for targeting a liposome to, for example, an smooth muscle cell include, but are not limited to: intact or fragments of molecules which interact with smooth muscle cell specific receptors and molecules, such as antibodies, which interact with the cell surface markers of cancer cells. Such ligands may easily be identified by binding assays well known to those of skill in the art. In still other embodiments, the liposome may be targeted to a tissue by coupling it to an antibody known in the art.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOPECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) Trends Biotechnol 3:235-241.

Certain cationic lipids, including in particular N-[1-(2, 3 dioleoyloxy)-propyl]-N,N,N-trimethylammonium methylsulfate (DOTAP), may be advantageous when combined with the XCIF inhibitors of the disclosure.

In some aspects of the disclosure, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, e.g., to deliver an XCIF inhibitor in a form that is more efficiently taken up by the cell or, in combination with one or more of the above-described carriers.

Other exemplary compositions that can be used to facilitate uptake of an XCIF inhibitor include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus* Calmette-Guérin, *Shigella, Lactobacillus*); live viral vectors (e.g., Vaccinia, adenovirus, Herpes Simplex); microspheres; nucleic acid vaccines; polymers (e.g., carboxymethylcellulose, chitosan); polymer rings; proteosomes; sodium fluoride; transgenic plants; virosomes; and, virus-like particles.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In addition to the formulations described herein, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Modes of Administration

The pharmaceutical compositions of the present disclosure preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally.

The pharmaceutical compositions containing an XCIF inhibitor and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this disclosure, generally speaking, may be practiced using any mode of administration that is medically acceptable, meaning any mode that produces therapeutic effect without causing clinically unacceptable adverse effects. Various modes of administration are discussed herein. For use in therapy, an effective amount of the XCIF inhibitor and/or other therapeutic agent can be administered to a subject by any mode that delivers the agent to the desired surface, e.g., mucosal, systemic.

Administering the pharmaceutical composition of the present disclosure may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In some embodiments, an inhibitory oligonucleotide can be delivered to the cells via an expression vector engineered to express the inhibitor oligonucleotide. An expression vector is one into which a desired sequence may be inserted, e.g., by restriction and ligation, such that it is operably joined to regulatory sequences and may be expressed as an RNA transcript. An expression vector typically contains an insert that is a coding sequence for a protein or for a inhibitory oligonucleotide such as an shRNA, a miRNA, or an miRNA. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays or fluorescent proteins, etc.

As used herein, a coding sequence (e.g., protein coding sequence, miRNA sequence, shRNA sequence) and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence may encode an miRNA, shRNA or miRNA.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses, a modified retrovirus, a nonreplicating retrovirus, a replication defective Semliki Forest virus, canarypox virus and highly attenuated vaccinia virus derivative, non-replicative vaccinia virus, replicative vaccinia virus, Venzuelan equine encephalitis virus, Sindbis virus, lentiviral vectors and Ty virus-like particle. Another virus useful for certain applications is the adeno-associated virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991).

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FECTOFLY™ transfection reagents for insect cells by Polyplus Transfection, Polyethylenimine "Max" by Polysciences, Inc., Unique, Non-Viral Transfection Tool by Cosmo Bio Co., Ltd., LIPOFECTAMINE™ LTX Transfection Reagent by Invitrogen, SATISFECTION™ Transfection Reagent by Stratagene, LIPOFECTAMINE™ Transfection Reagent by Invitrogen, FUGENE® HD Transfection Reagent by Roche Applied Science, GMP compliant IN VIVO-JETPEI™ transfection reagent by Polyplus Transfection, and Insect GENEJUICE® Transfection Reagent by Novagen.

EXAMPLES

The following examples are intended to illustrate the disclosure. They are not meant to limit the disclosure in any way.

Aspects of the present disclosure relate to the reactivation of X chromosomes. As described herein, small molecule inhibitors of XCIFs can, like RNAi knockdown, reactivate the expression of the Xi-linked genes, which has implications for treatment of Rett syndrome and other dominant X-linked diseases. Thirteen X chromosome inactivation factors (XCIFs) have been identified (Table 1), and are involved in the transcriptional repression of X-linked genes.

TABLE 1

| Summary of X Chromosome Inactivation Factors | | | | |
| --- | --- | --- | --- | --- |
| Mouse gene symbol | Human gene symbol | Gene name | Chromosome Mouse (human) | Biological process |
| Acvr1 | ACVR1 | activin A receptor, type 1 | 2 (2) | Signal transduction |
| Aurka | AURKA | aurora kinase A | 2 (20) | Cell cycle regulation |

TABLE 1-continued

Summary of X Chromosome Inactivation Factors

| Mouse gene symbol | Human gene symbol | Gene name | Chromosome Mouse (human) | Biological process |
|---|---|---|---|---|
| Dnmt1 | DNMT1 | DNA methyltransferase (cytosine-5) 1 | 9 (19) | Chromatin modification |
| Fbxo8 | FBXO8 | F-box protein 8 | 8 (4) | Unknown/Ubiquitin-dependent protein catabolic process |
| Layn | LAYN | Layilin | 9 (11) | Unknown/Receptor for hyaluronic acid |
| Nf1 | NF1 | neurofibromatosis 1 | 11 (17) | Signal transduction |
| Pdpk1 | PDPK1 | 3-phosphoinositide dependent protein kinase-1 | 17 (16) | Signal transduction |
| Pygo1 | PYGO1 | pygopus 1 | 9 (15) | Transcriptional regulation |
| Rnf165 | RNF165 | ring finger protein 165 | 18 (18) | Unknown |
| Sox5 | SOX5 | SRY-box containing gene 5 | 6 (12) | Transcriptional regulation |
| Stc1 | STC1 | stanniocalcin 1 | 14 (8) | Cell metabolism |
| Zfp426 | ZNF426 | zinc finger protein 426 | 9 (19) | Transcriptional regulation |
| 1700001P01Rik | C17orf98 | RIKEN cDNA 1700001P01 gene | 11 (17) | Unknown |

Example 1: Identification of Factors Involved in Mammalian XCI

A previously derived female mouse embryonic fibroblast cell line (H4SV) in which genes encoding green fluorescent protein (GFP) and hypoxanthine guanine phosphoribosyltransferase (HPRT) are present only on the Xi was used. Knockdown of a factor involved in XCI is expected to reactivate expression of the Gfp and Hprt reporter genes (FIG. 1A).

Figure 7A:
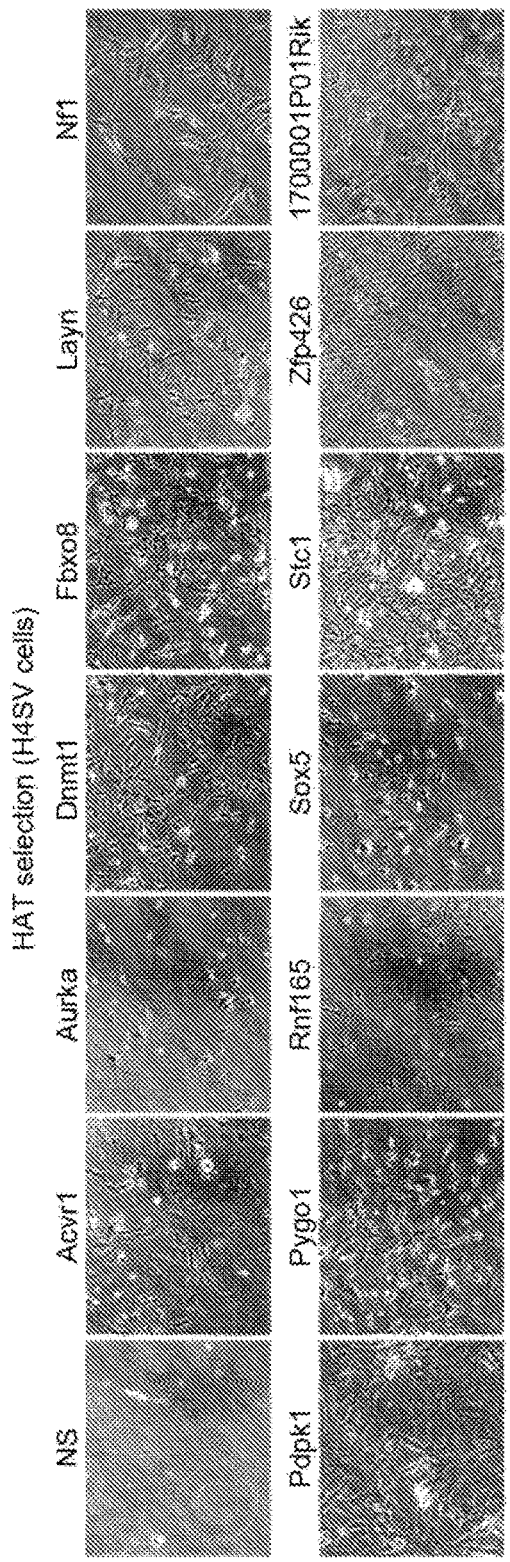
FIGS. 7A-7D show shRNAs targeting an XCIF reactivate the Xi-linked Hprt gene and decrease mRNA levels of the targeted gene.
Figure 7B:
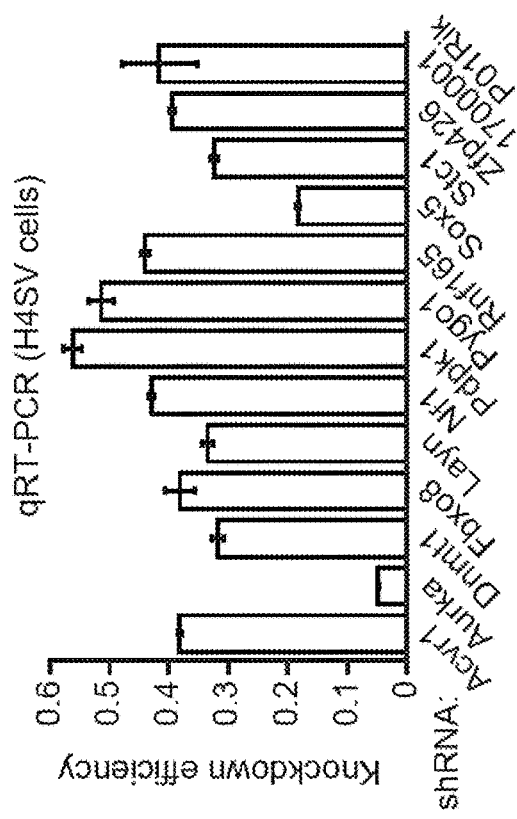
Figure 7C:
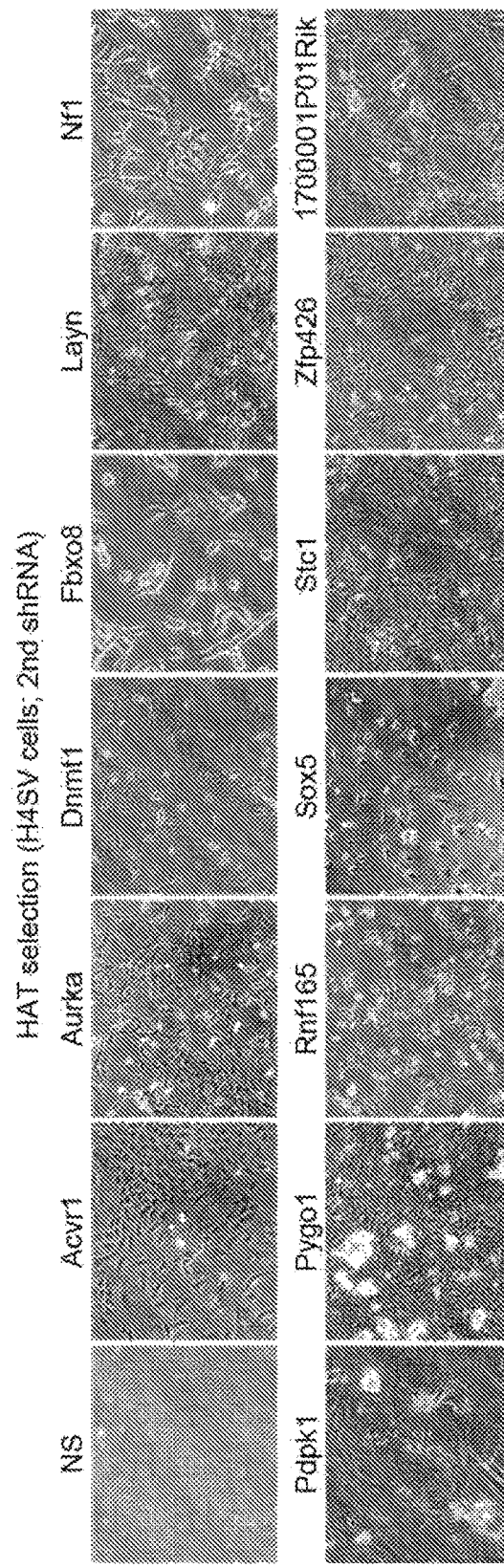
Figure 7D:
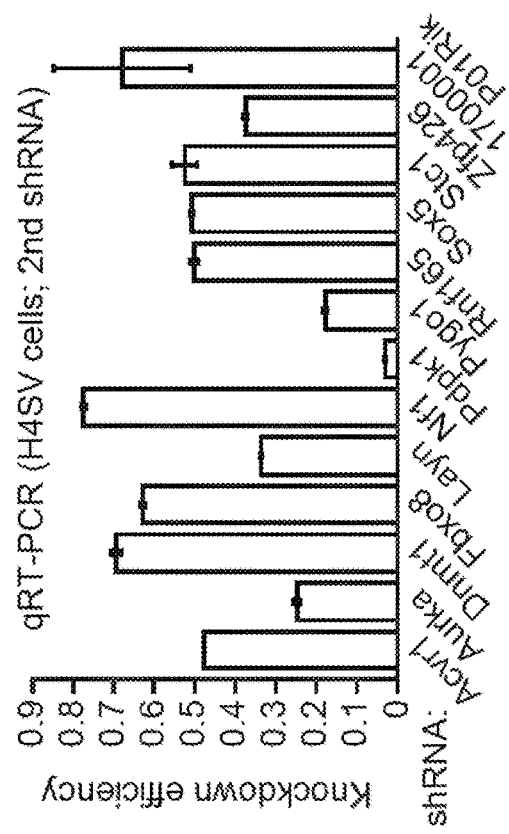

A genome-wide mouse shRNA library comprising 62,400 shRNAs was divided into 10 pools, which were packaged into retrovirus particles and used to transduce H4SV cells. GFP-positive cells were selected by fluorescence-activated cell sorting (FACS), expanded, and the shRNAs were identified by sequence analysis. To validate the candidates, single shRNAs directed against each candidate gene were transduced into H4SV cells and the number of GFP-positive cells measured by FACS analysis. The results of these experiments identified 13 candidate genes whose knockdown resulted in an increased percentage of GFP-positive cells relative to that obtained with a control, non-silencing (NS) shRNA (FIG. 1B). The cell viability assay of FIG. 7A shows that knockdown of each candidate enabled growth in HAT medium, indicating that the Xi-linked Hprt gene was reactivated. As expected, the mRNA levels of the 13 candidate genes were decreased in the corresponding KD H4SV cell line (FIG. 7B). To rule out off-target effects, for all 13 candidates it was shown that a second, unrelated shRNA also reactivated the Xi-linked Hprt gene (FIG. 7C) and decreased mRNA levels of the targeted gene in the corresponding KD H4SV cell line (FIG. 7D). The 13 X chromosome inactivation factors (XCIFs) are listed in Table 1 and include proteins that are known, or predicted, to be involved in diverse processes including cell signaling (PDPK1, AURKA, LAYN, ACVR1 and NF1), transcription (DNMT1, PYGO1, SOX5 and ZFP426) and ubiquitin-dependent regulation (RNF165 and FBXO8). Significantly, DNMT1 has been previously shown to be involved in XCI, validating the screening strategy.

Figure 1C:
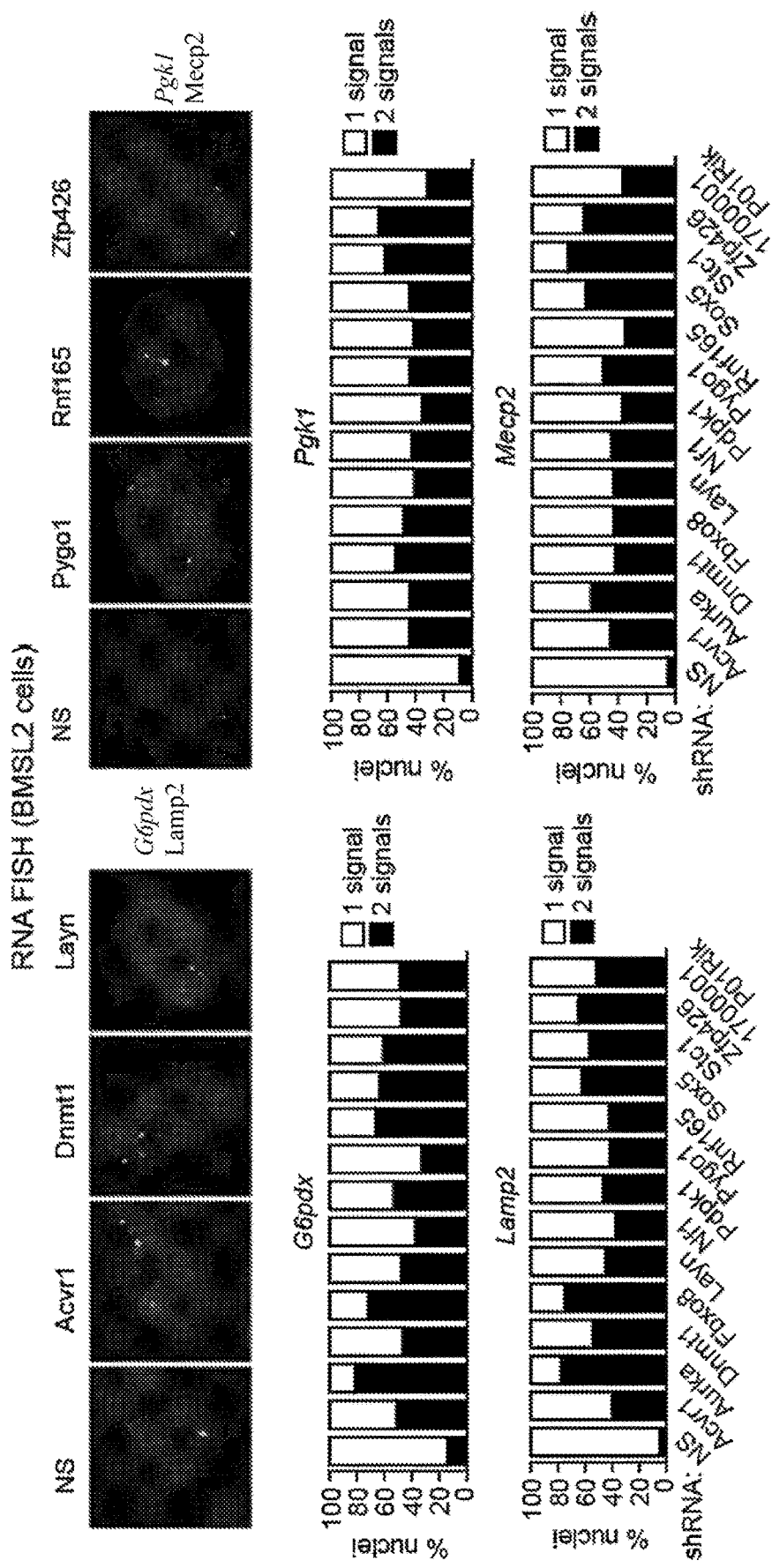
Figure 8A:
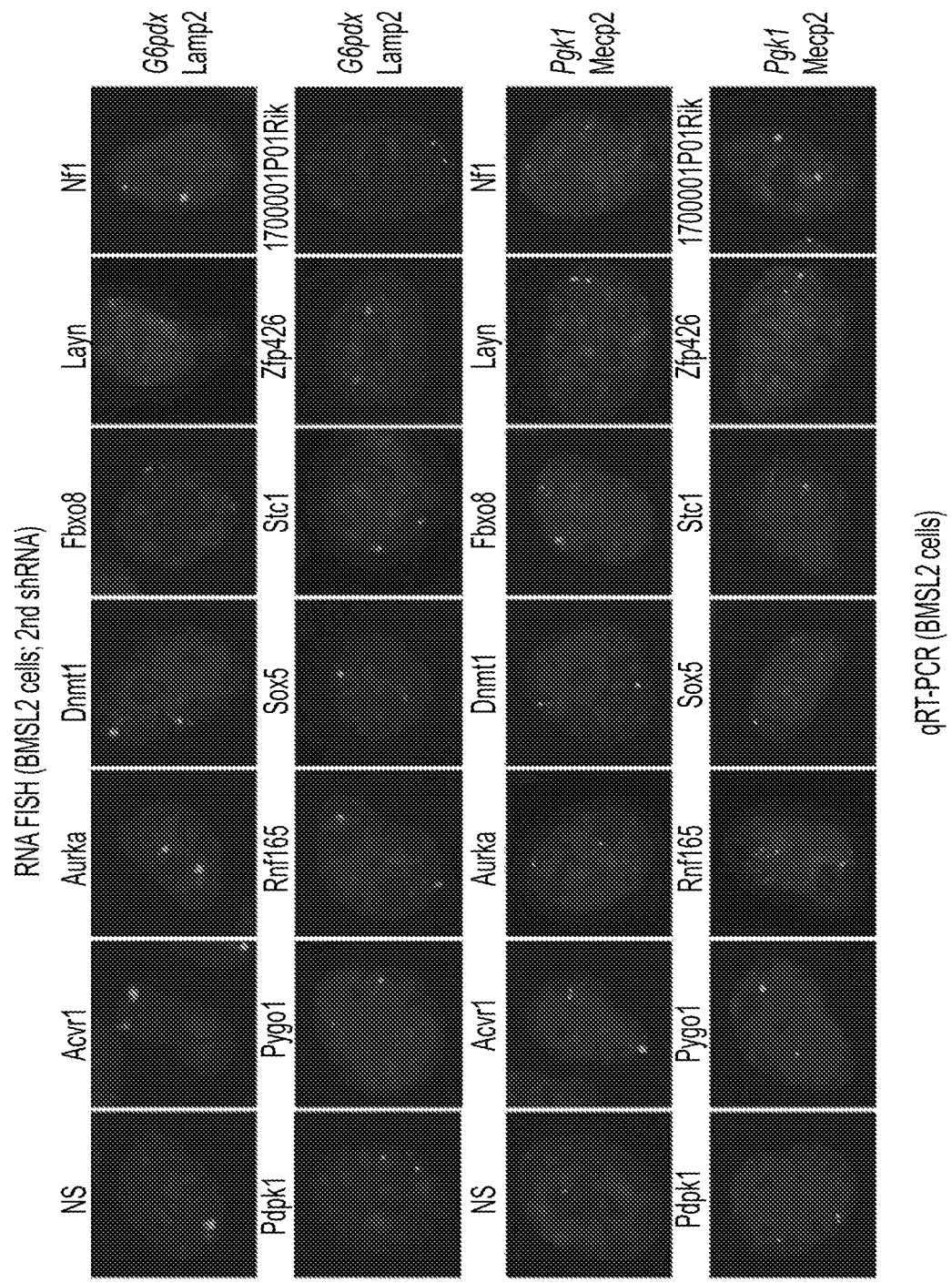
FIGS. 8A-8D show additional RNA FISH images and control experiments related to FIGS. 1A-1C.
Figure 8B:
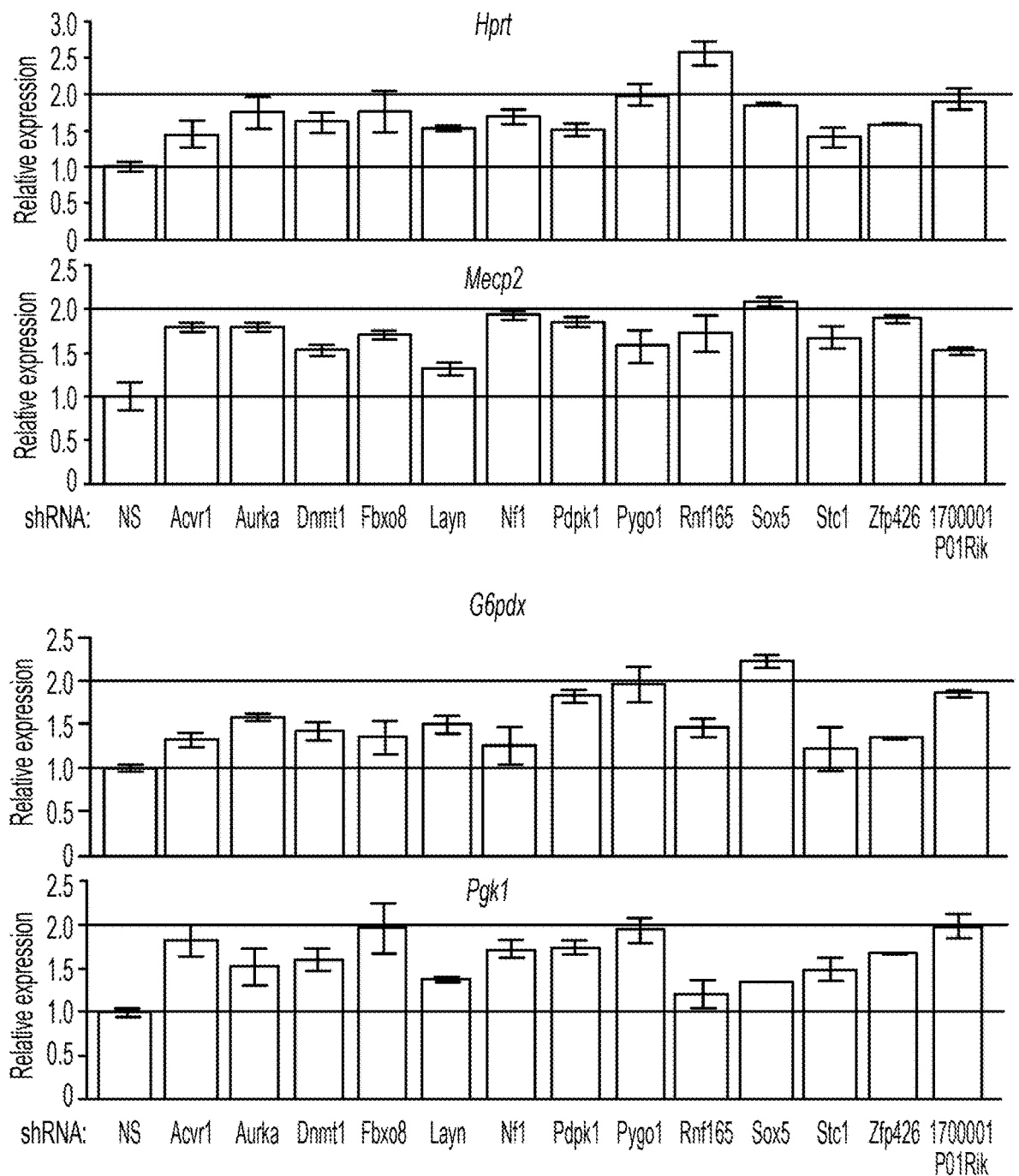
Figure 8C:
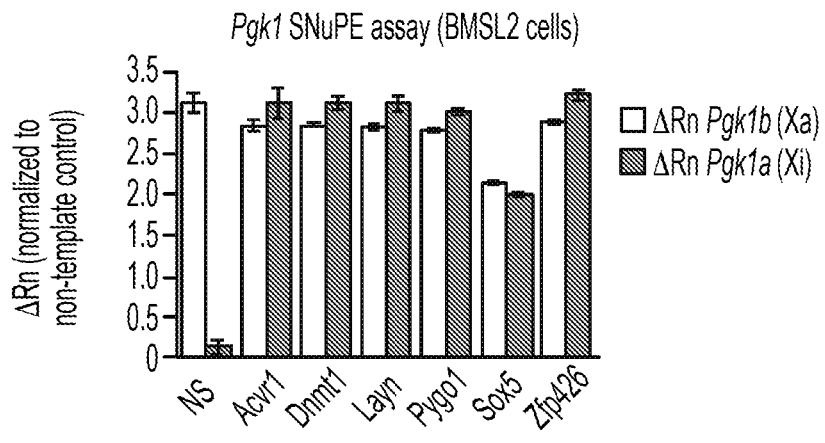
Figure 8D:
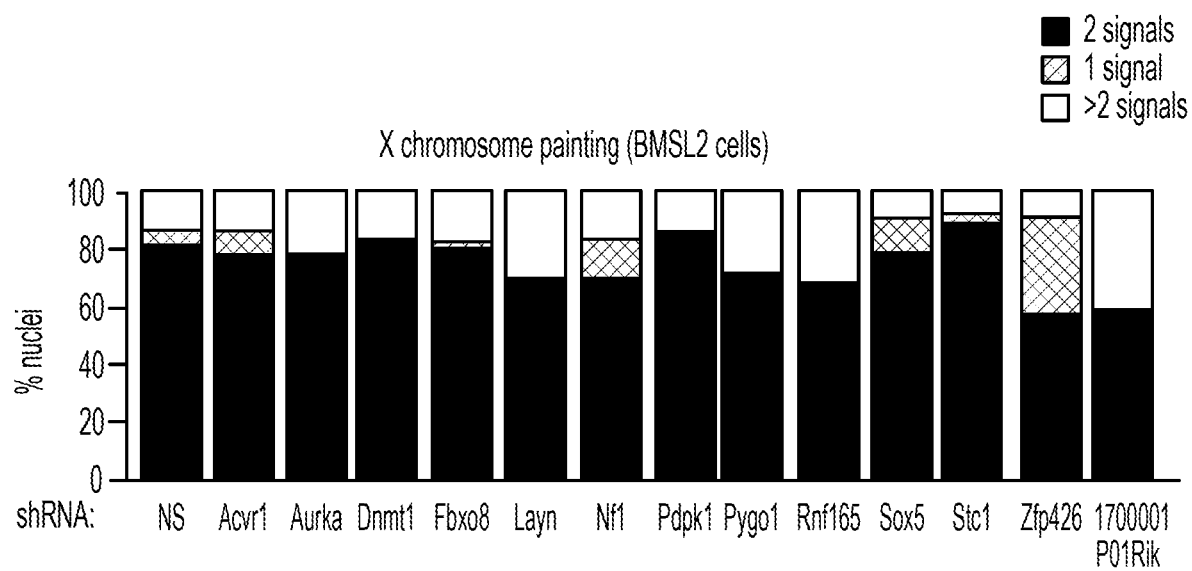

To confirm these results, the expression of four X-linked genes, G6pdx, Lamp2, Pgk1 and Mecp2 was analyzed, using two-color RNA fluorescence in situ hybridization (FISH) in BMSL2 cells, an unrelated female mouse fibroblast cell line. In BMSL2 cells expressing a control NS shRNA, RNA FISH revealed, as expected, a single nuclear signal for G6pdx, Lamp2, Pgk1 and Mecp2, indicative of monoallelic expression (FIG. 1C and FIG. 8A). Knockdown of each of the 13 XCIFs substantially increased the fraction of cells containing two nuclear G6pdx, Lamp2, Pgk1 and Mecp2 signals, indicative of biallelic expression. Reactivation of G6pdx, Pgk1, Mecp2 and Hprt in the 13 XCIF KD BMSL2 cell lines was also demonstrated by a ~1.5-2-fold increase in mRNA levels as monitored by qRT-PCR (FIG. 8B). Reactivation of the Xi-linked Pgk1 gene in representative XCIF KD BMSL2 cell lines was also demonstrated using a single nucleotide primer extension (SNuPE) assay (FIG. 8C), which could distinguish expression of the Xi- and Xa-linked Pgk1 alleles by virtue of a single nucleotide polymorphism. DNA FISH experiments using an X chromosome-specific paint probe indicated that the X chromosome content of the XCIF KD BMSL2 cell lines was similar to that of the control BMSL2 cell line expressing a NS shRNA (FIG. 8D).

Figure 2A:
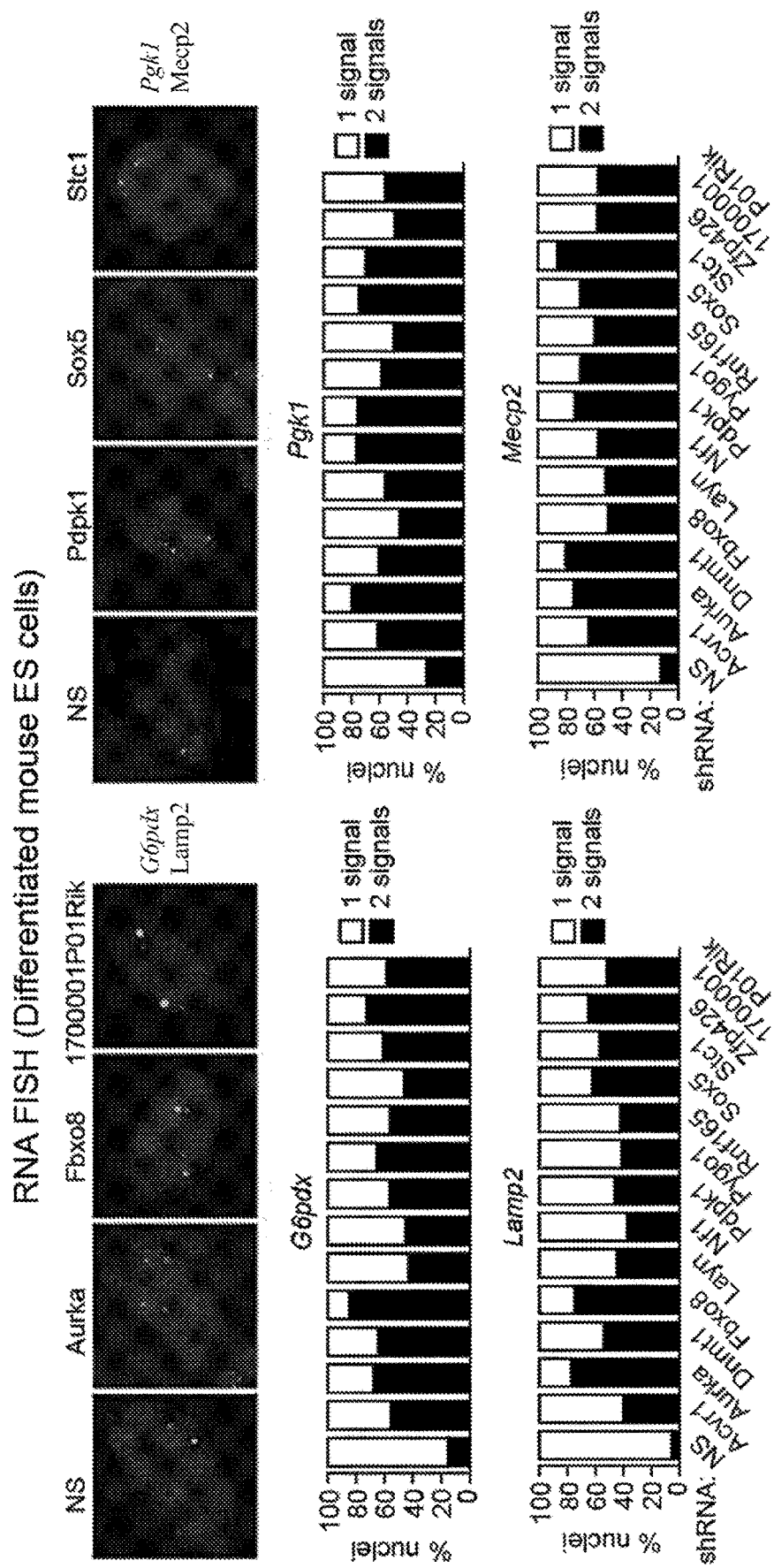
FIGS. 2A-2D show XCIFs are involved in initiation of XCI in mouse embryonic stem cells.
Figure 9A:
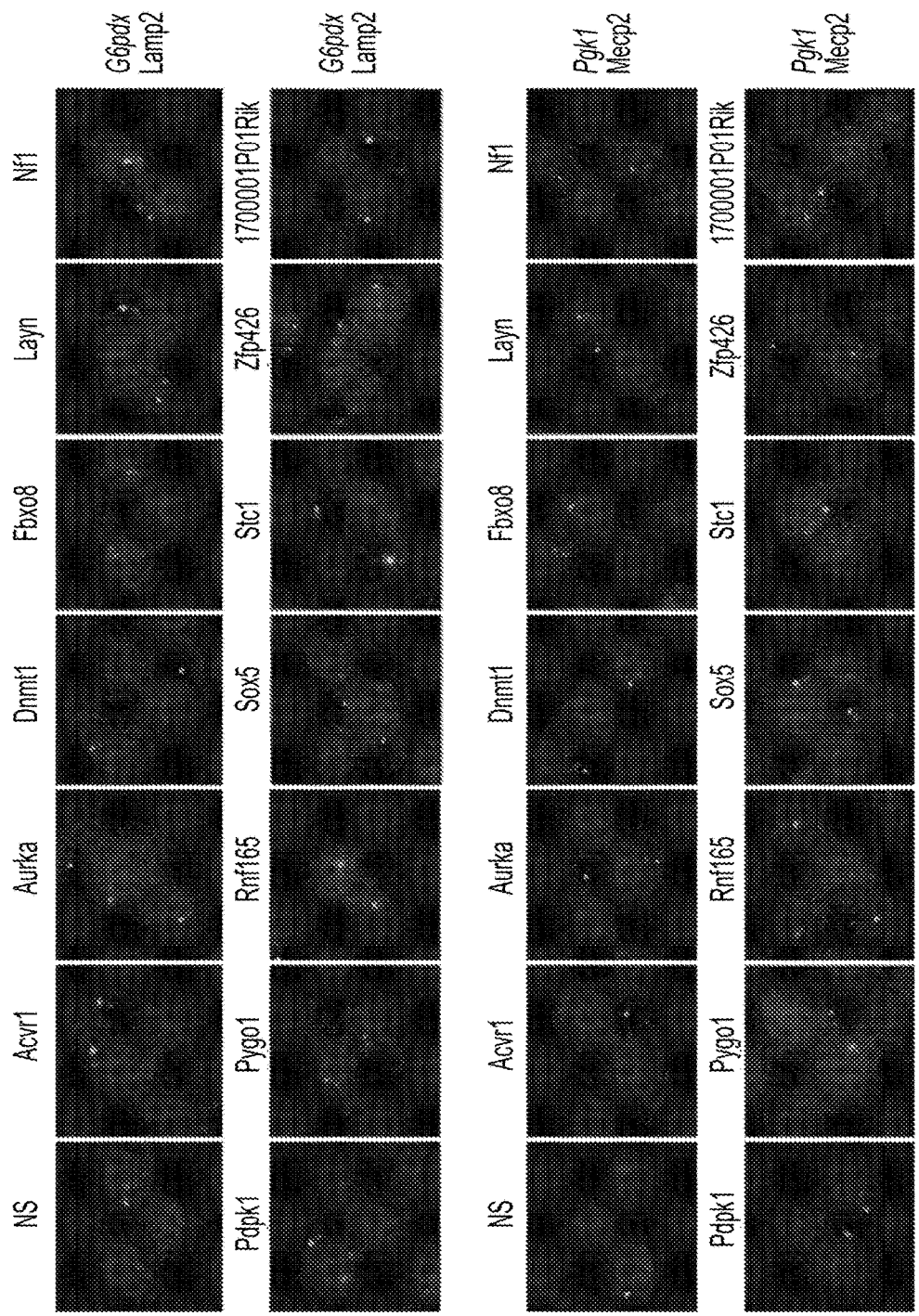
FIGS. 9A-9C show additional RNA FISH images and control experiments related to FIGS. 2A-2D.
Figure 9B:
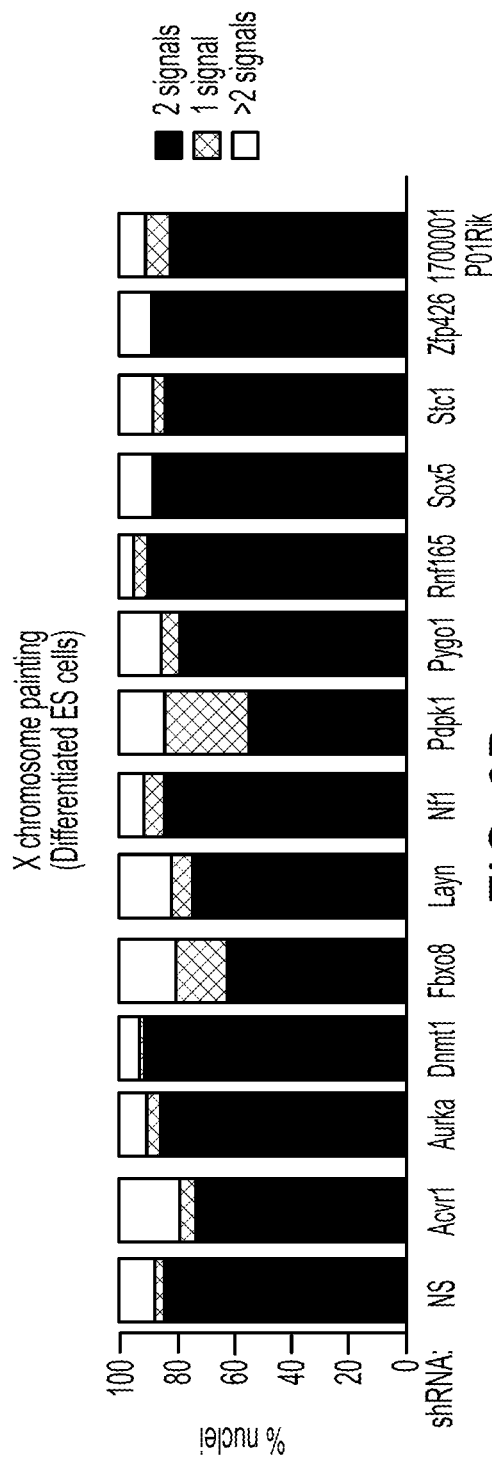

Example 2: The XCIFs are Involved in Initiation of XCI in Mouse Embryonic Stem Cells Undifferentiated female mouse PGK12.1 ES cells were transduced with a retrovirus expressing an XCIF shRNA. Cells were then treated with retinoic acid (RA), which induces predominantly, but not exclusively, neuronal differentiation. X-linked gene expression was monitored by two-color RNA FISH. FIG. 2A and FIG. 9A show that biallelic expression of the X-linked G6pdx, Lamp2, Pgk1 and Mecp2 genes was substantially increased following knockdown of each XCIF. As above, the X chromosome content of the XCIF KD ES cells was similar to that of the control ES cell line expressing a NS shRNA (FIG. 9B).

Figure 2B:
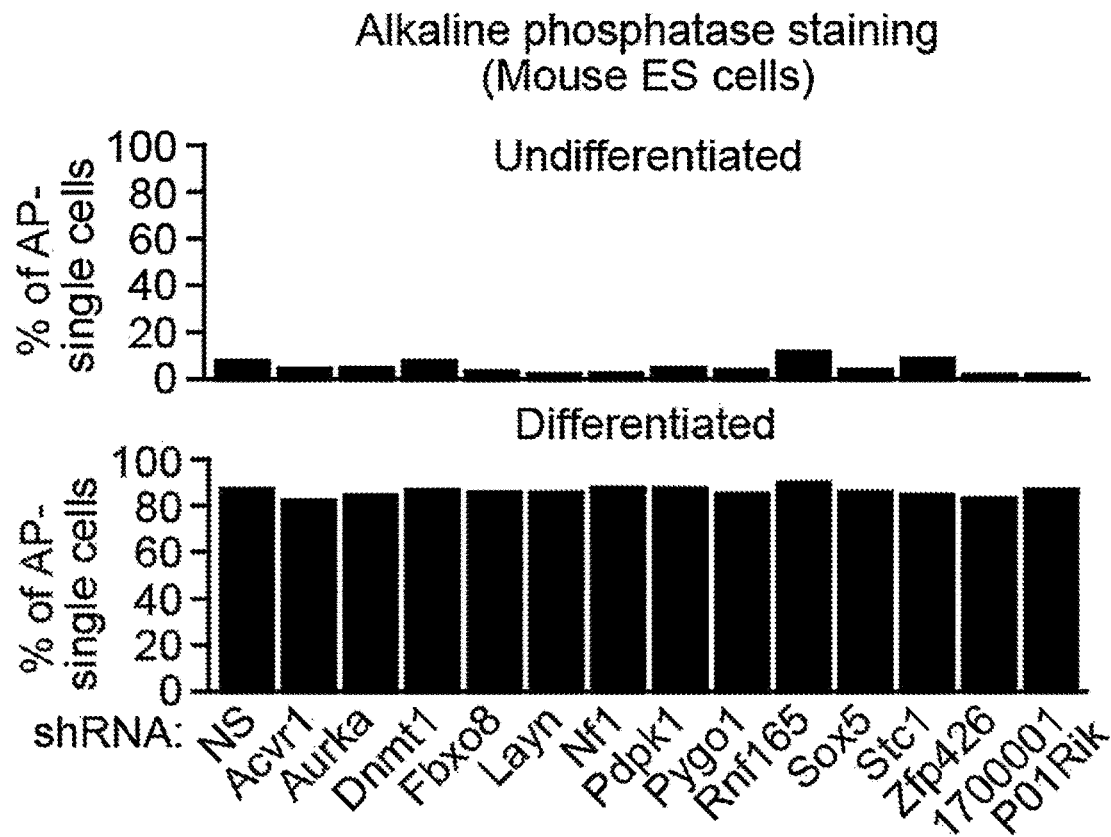
Figure 2C:
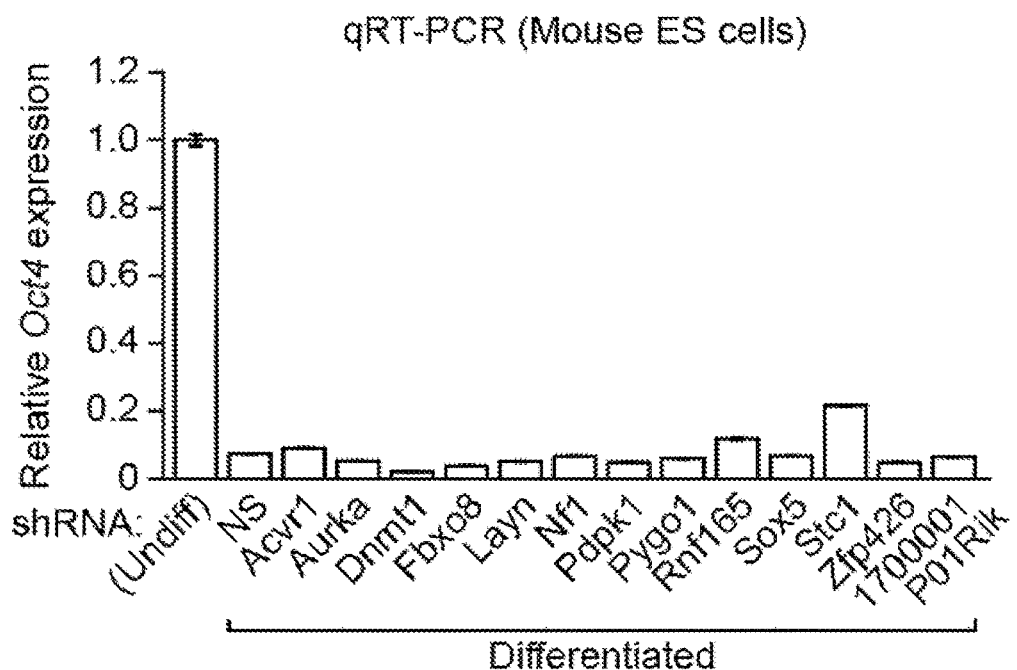
Figure 2D:
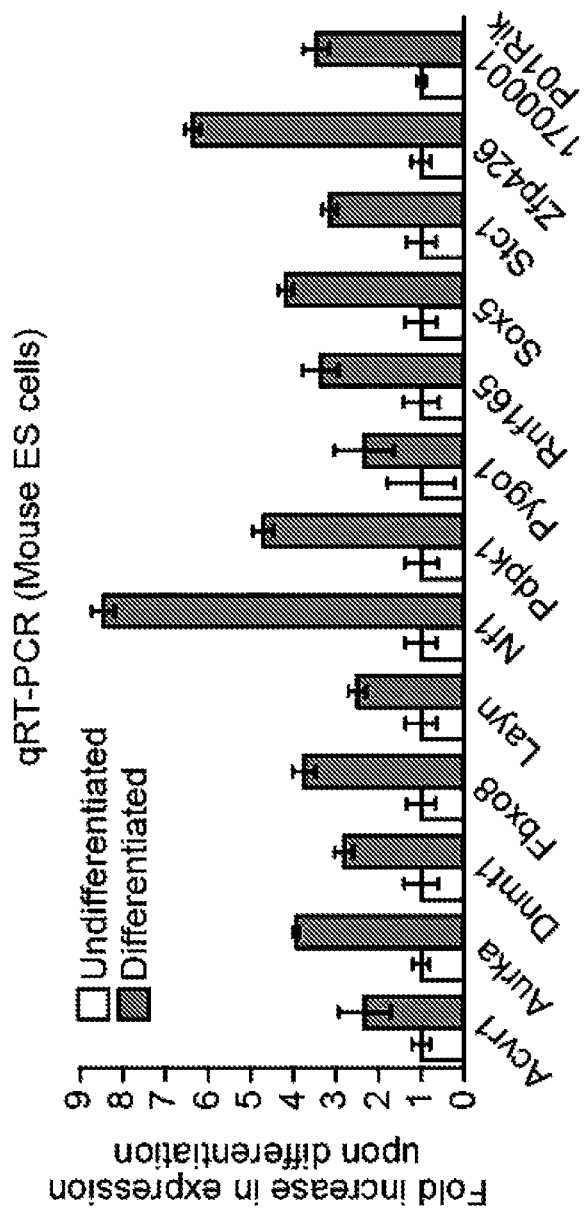
Figure 9C:
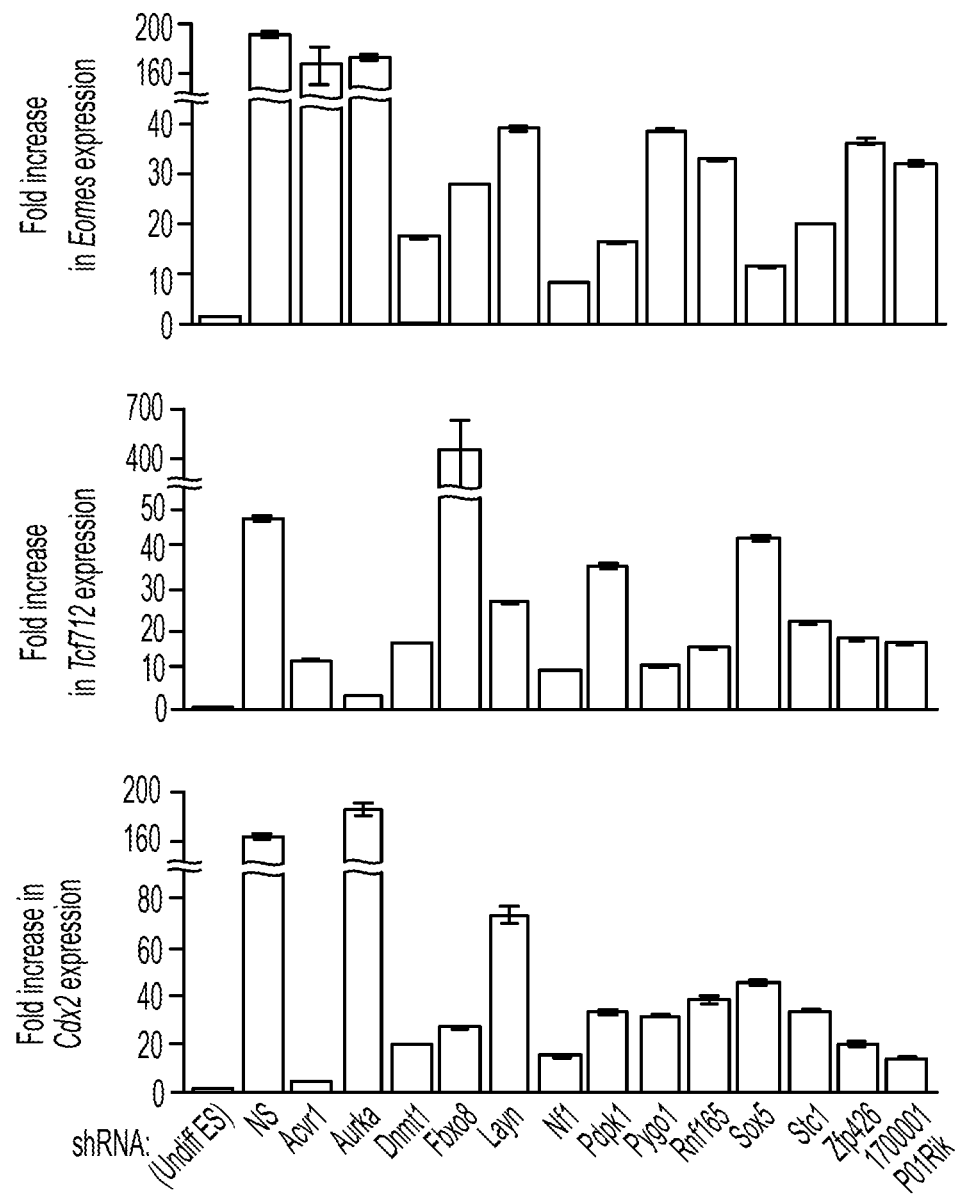

A possible explanation for the failure of one or more of the 13 XCIF KD ES cell lines to undergo XCI is that the XCIF is involved in differentiation. Following RA treatment, differentiation of the 13 XCIF KD ES cell lines was normal, as evidenced by monitoring two well-established markers of undifferentiated ES cells, alkaline phosphatase activity (FIG. 2B) and Oct4 expression (FIG. 2C). Likewise, several markers of differentiated cells that increase after RA treatment (Eomes [neuronal], Tcf712 [mesoderm] and Cdx2 [epithelial]) were unaffected by XCIF knockdown (FIG. 9C). Finally, the quantitative real-time RT-PCR (qRT-PCR) results of FIG. 2D show that expression of all 13 XCIFs was upregulated following differentiation, explaining, at least in part, the selective onset of XCI following differentiation.

Figure 3A:
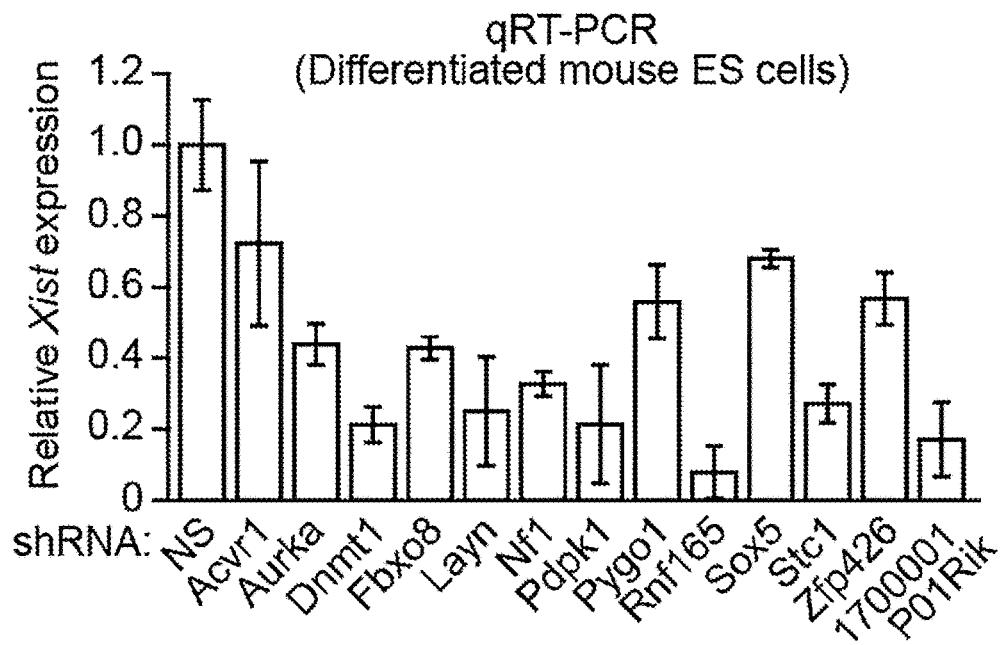
FIGS. 3A-3I show XCIFs function by promoting Xist expression and/or localization, and DNMT1 is a transcriptional activator of Xist on the Xi.
Figure 3B:
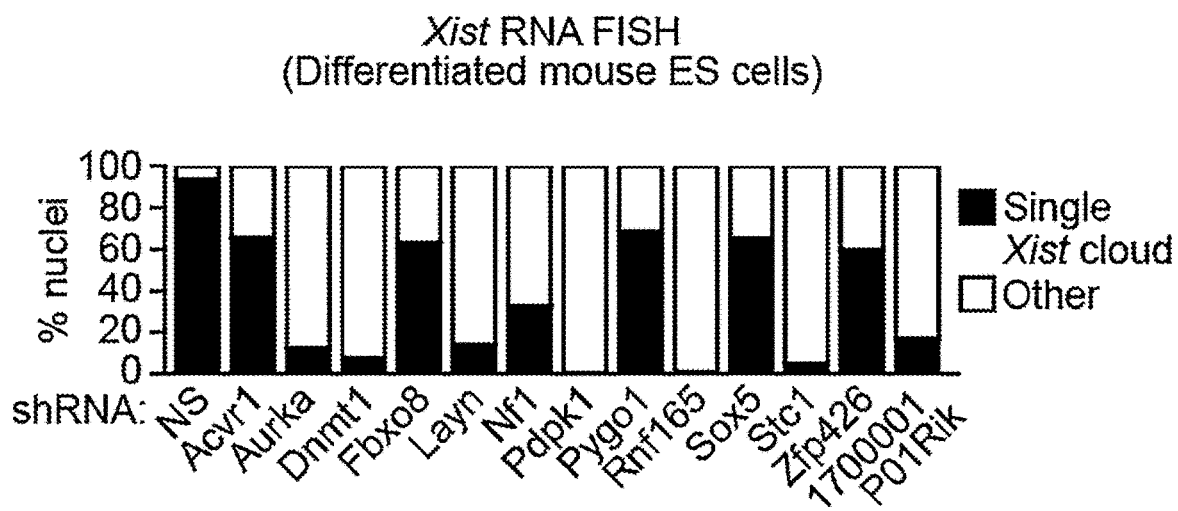
Figure 10A:
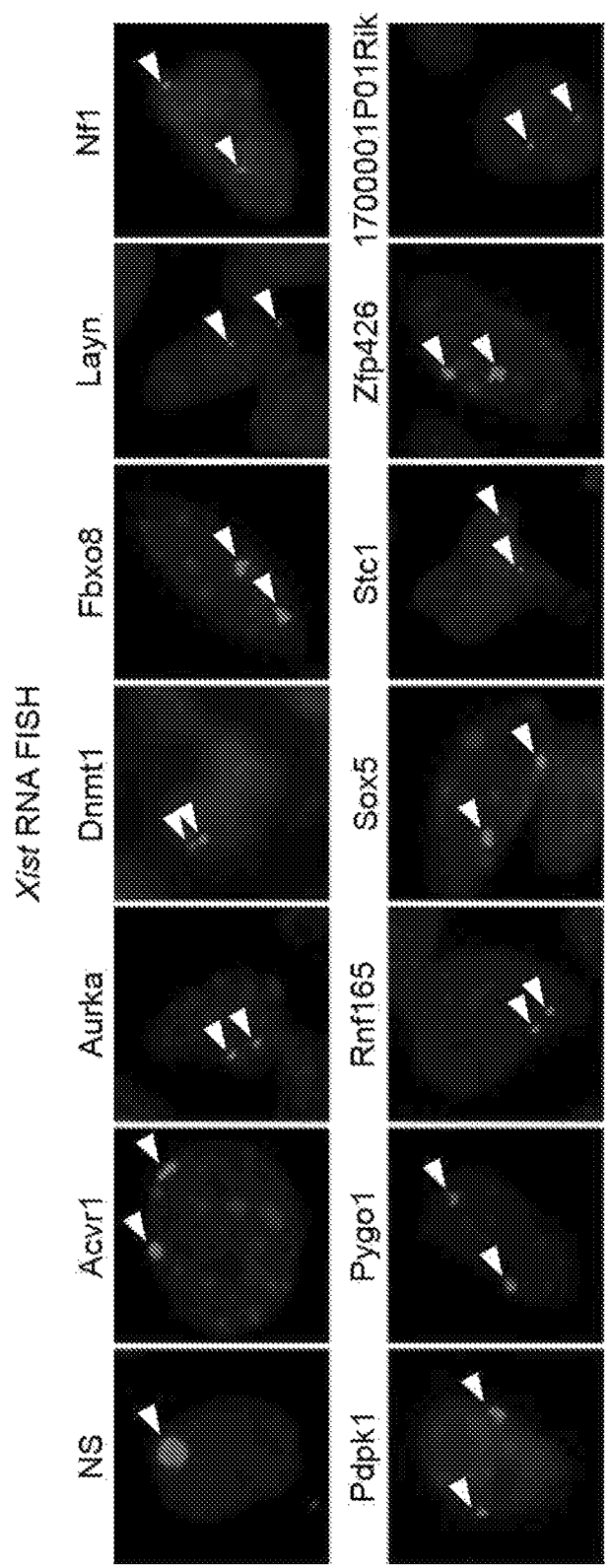
FIGS. 10A-10C show RNA FISH images and control experiments related to FIGS. 3A-3I.

Example 3: XCIFs Function by Promoting Xist Expression and/or Localization to the Xi Following knockdown of the 13 XCIFs in mouse ES cells, RA was added to induce differentiation and XCI, and Xist expression was analyzed by qRT-PCR. The results of FIG. 3A show that Xist levels were reduced to varying extents in all XCIF KD ES cell lines. In differentiated female ES cells, Xist is detected by RNA FISH as a large, diffuse nuclear signal referred to as a "cloud" that co-localizes with the Xi. FIG. 3B shows that knockdown of each of the XCIFs reduced to varying extents the percentage of cells with the Xist localization pattern characteristic of XCI (see also FIG. 10A). Taken together, these results indicate that XCIFs promote Xist expression and/or localization of Xist to the Xi.

Figure 3C:
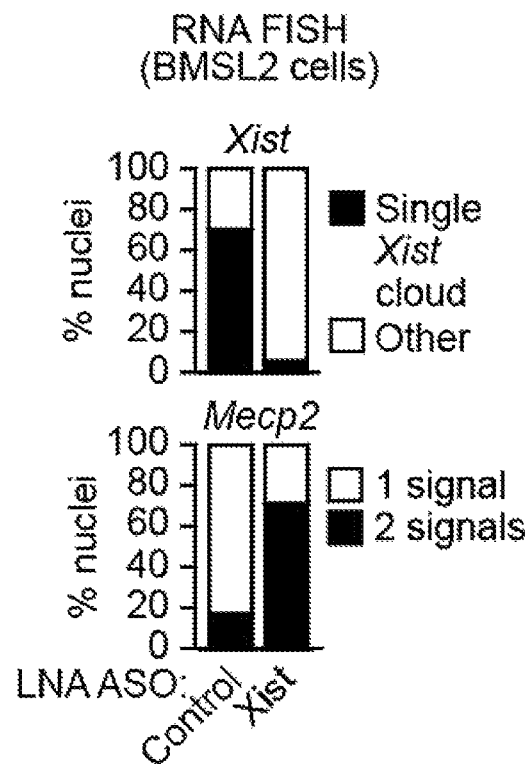

Several previous studies have suggested that Xist is required for the initiation but not maintenance of XCI. However, the results of FIGS. 3A and B implied that Xist was also necessary for maintenance of XCI. To provide independent evidence for this model, the Xist function in mouse BMSL2 fibroblasts was abrogated using an Xist antisense locked nucleic acid (LNA) oligonucleotide. The results of FIG. 3C show, consistent with previous results, that the Xist antisense LNA oligonucleotide perturbed the normal pattern of Xist expression/localization. Most importantly, the Xist antisense LNA oligonucleotide substantially increased biallelic expression of X-linked Mecp2. Thus, Xist is involved in both the initiation and maintenance of XCI.

Example 4: DNMT1 is a Transcriptional Activator of Xist on the Xi

Figure 3D:
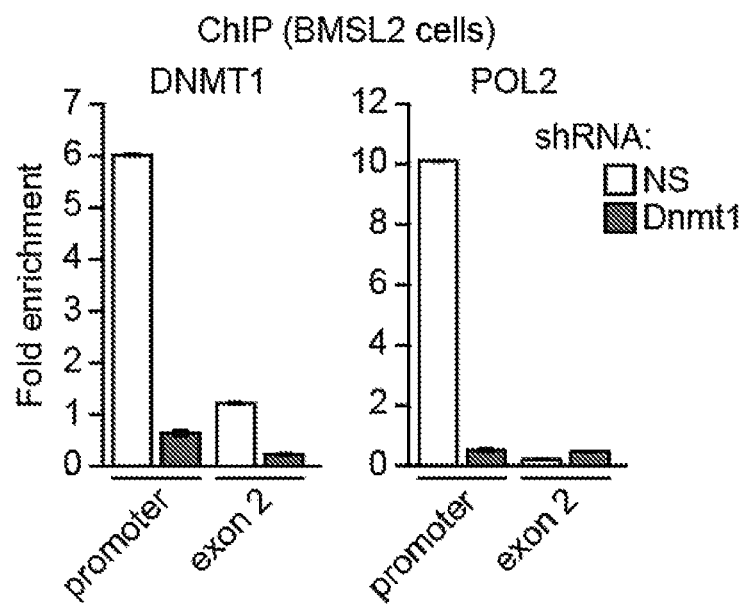
Figure 3E:
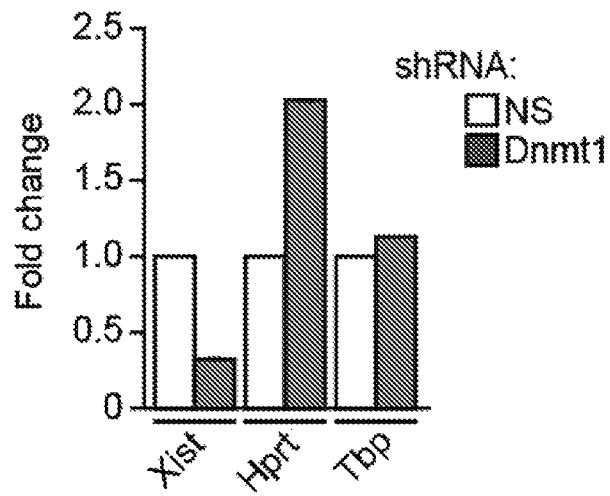
Figure 3F:
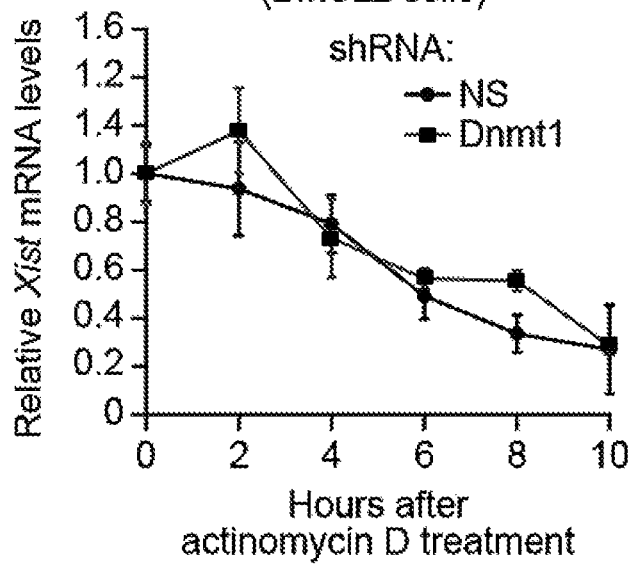
Figures 3G, 3H, 3I:
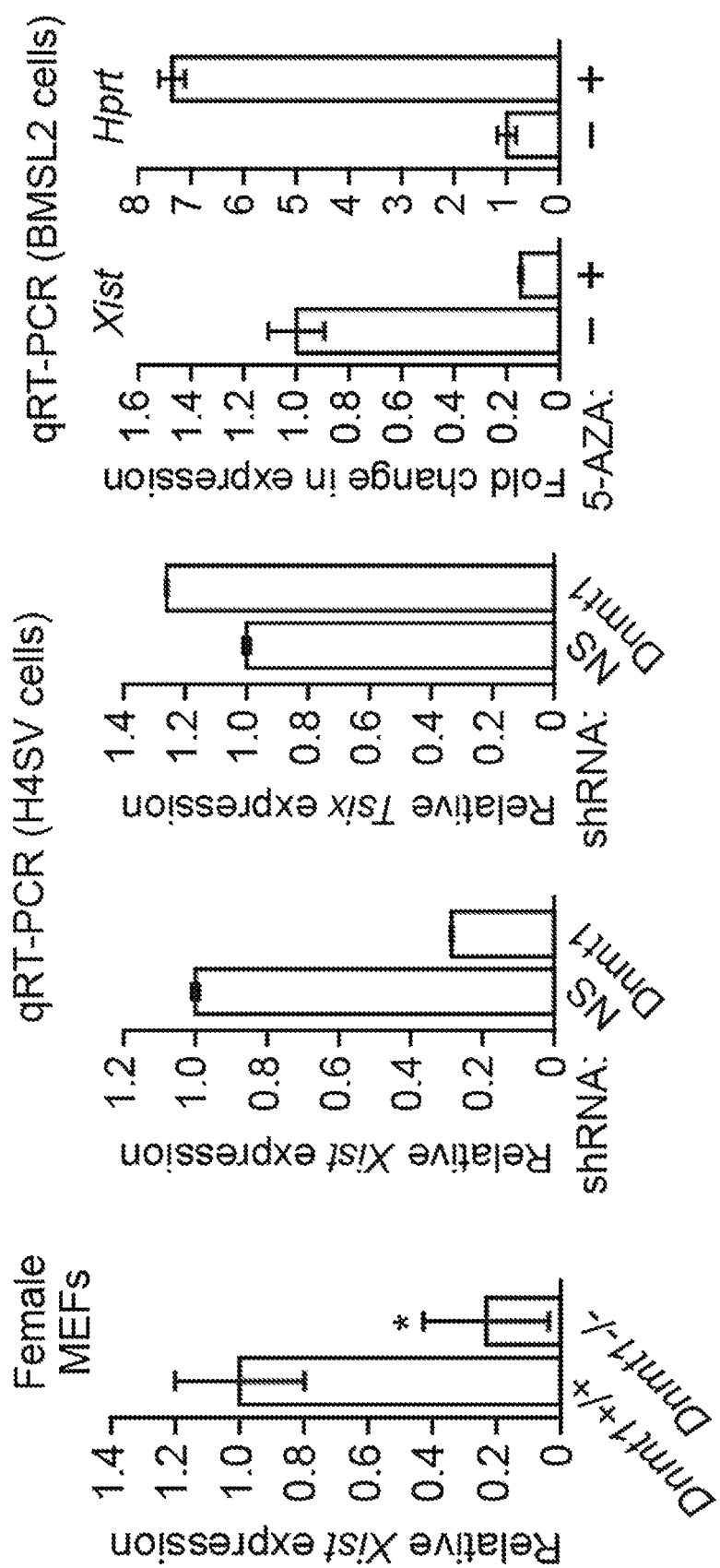

DNMT1, which typically functions as a transcriptional repressor, was found to be involved in Xist expression and/or localization to the Xi. To further investigate this finding, chromatin immunoprecipitation (ChIP) experiments were performed in BMSL2 cells in which the Xa harbors a deletion encompassing the Xist promoter and several genes including Hprt. FIG. 3D shows that DNMT1 and, as expected, RNA polymerase II (POL2) were bound near the Xist transcription start-site on the Xi. The fact that DNMT1 was involved in Xist transcription and bound to the Xist promoter suggested that DNMT1 might function as a direct transcriptional activator of Xist. Consistent with this idea, following knockdown of DNMT1 the level of POL2 bound to the Xist promoter substantially decreased (FIG. 3D). Moreover, in a nuclear run-on assay DNMT1 knockdown reduced Xist transcription but increased Xi-linked Hprt transcription, as expected (FIG. 3E). As a control, transcription of the TATA-box-binding protein (Tbp) gene, which is not X-linked and expressed constitutively, was unaffected by DNMT1 knockdown. In addition, knockdown of DNMT1 did not affect the half-life of Xist RNA (FIG. 3F) indicating the decreased levels of Xist RNA following DNMT1 depletion were predominantly transcriptional. Finally, the level of Xist transcripts was significantly lower in Dnmt1−/− compared to Dnmt1+/+ mouse embryonic fibroblasts (MEFs) (FIG. 3G). Collectively, these results indicate that DNMT1 is a transcriptional activator of Xist on the Xi.

Figure 10B:
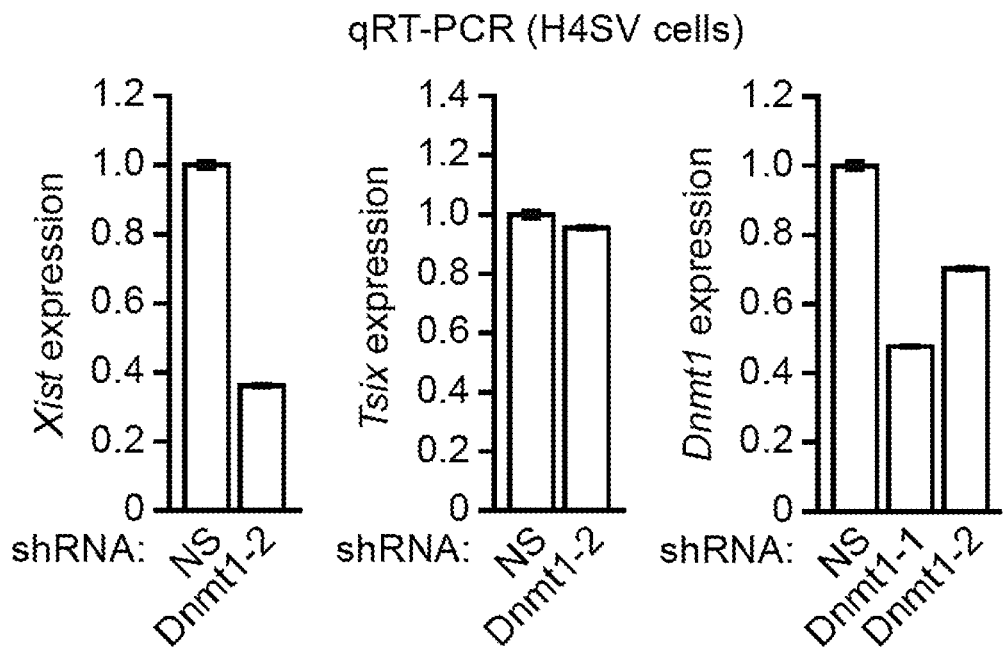
Figure 10C:
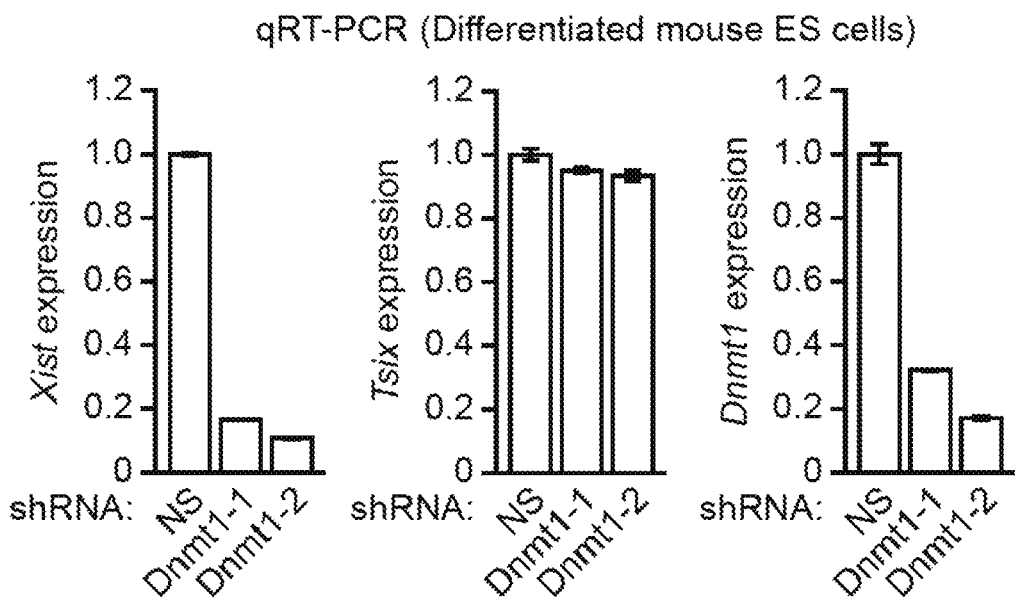

The possibility that DNMT1 indirectly activated Xist transcription by repressing expression of Tsix, which negatively regulates Xist was considered. However, knockdown of DNMT1 in fibroblasts (FIG. 3H and FIG. 10B) or murine ES (FIG. 10C) cells substantially decreased Xist expression but did not affect Tsix levels. DNMT1-mediated methylation at the Xist promoter could block the binding of a transcriptional repressor. Consistent with this possibility, following addition of 5-azacytidine, which inhibits DNMT1 enzymatic activity resulting in DNA demethylation, Xist levels were markedly reduced whereas expression of the Xi-linked Hprt gene increased, as expected (FIG. 3I). Collectively, these results suggest that DNMT1 promotes Xist transcription by antagonizing a repressor.

Figure 4C:
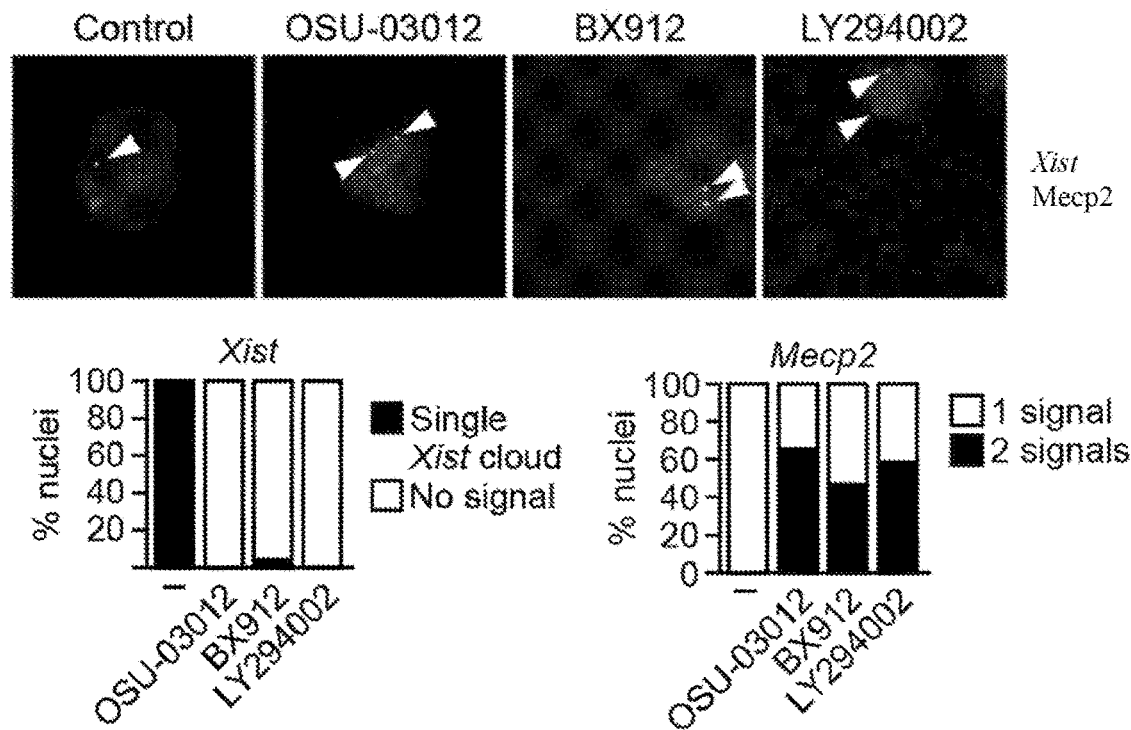

Example 5: Reactivation of the Xi-Linked Mecp2 Gene by Small Molecule XCIF Inhibitors One of the XCIFs is PDPK1, a serine-threonine kinase that regulates phosphatidylinositol-3-kinase (PI3K)/AKT signaling. FIG. 4A and FIG. 11A show that following treatment of differentiated female mouse ES cells with a chemical inhibitor of either PDPK1 (OSU-03012) or PI3K (LY294002), there was a dose-dependent loss of the Xist cloud and increased biallelic expression of Mecp2. Similar results were obtained in BMSL2 cells using GNE-317 (FIG. 4B and FIG. 11B), a PI3K inhibitor specifically designed to cross the blood-brain barrier. As expected, with all three inhibitors the majority of cells contained two Mecp2 RNA FISH signals and lacked a detectable Xist cloud. Notably, however, in some cells one of the two Mecp2 RNA FISH signals colocalized with a Xist cloud, which marked the Xi. Similar results were obtained with post-mitotic mouse cortical neurons using the PDPK1 inhibitors OSU-03012 and BX912 or the PI3K inhibitor LY294002 (FIG. 4C).

Figure 4D:
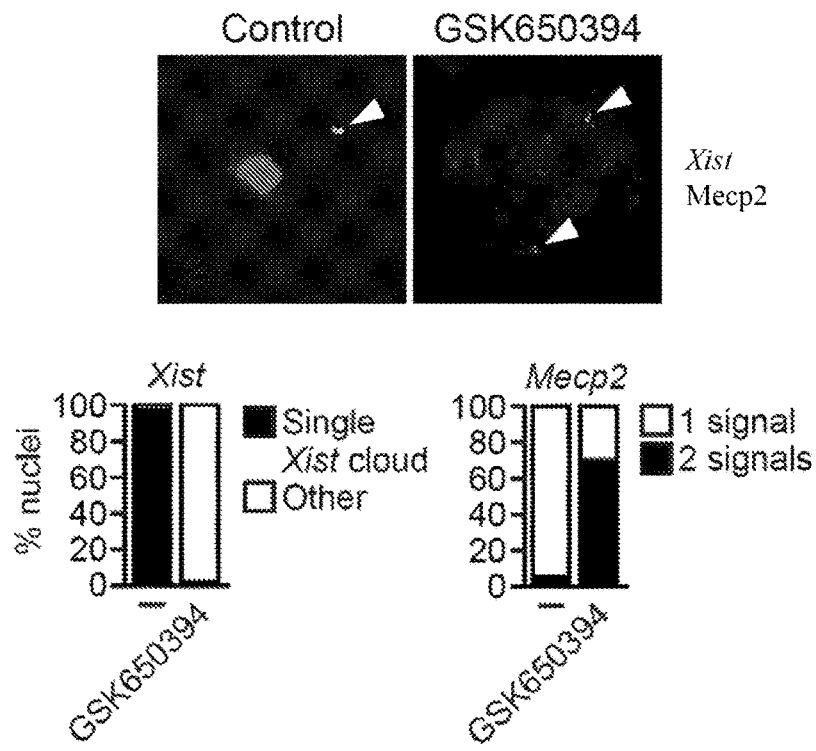
Figure 4E:
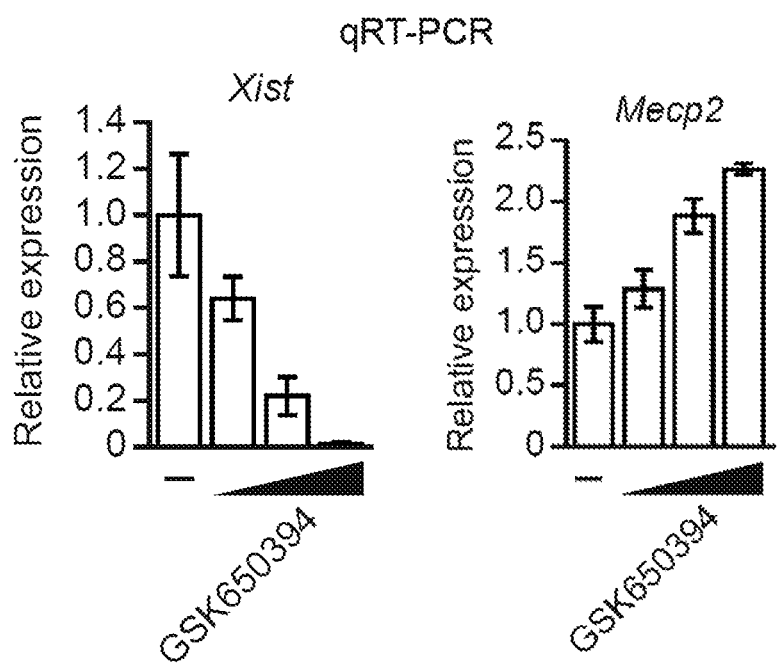
Figure 4F:
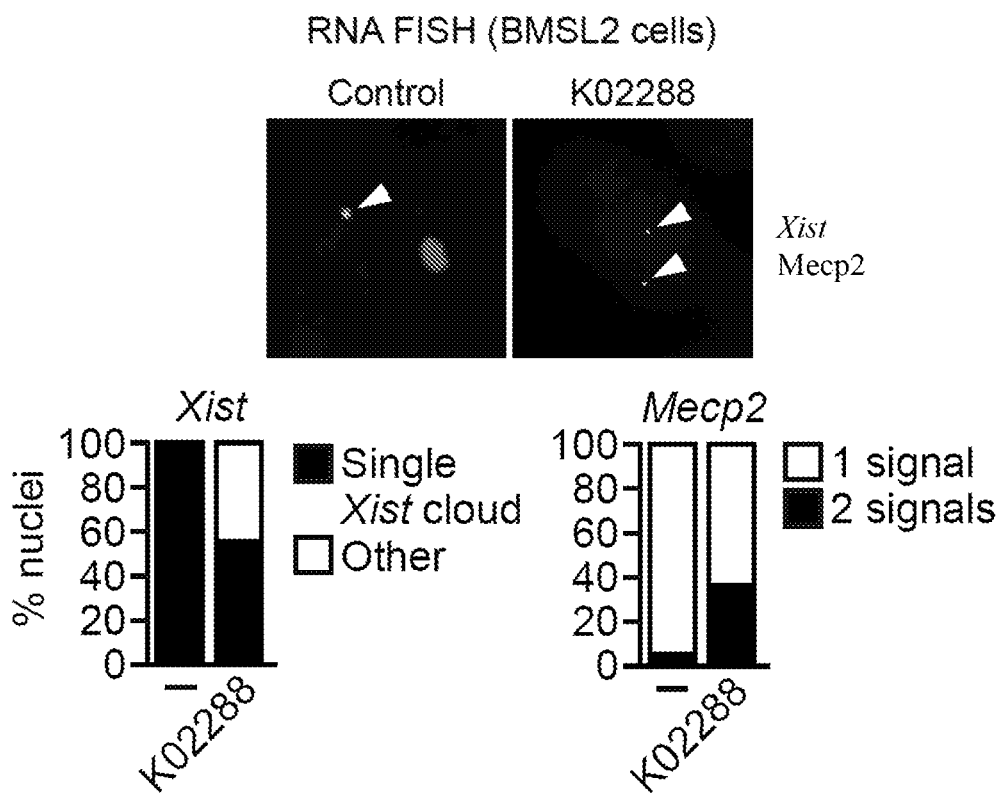
Figure 4G:
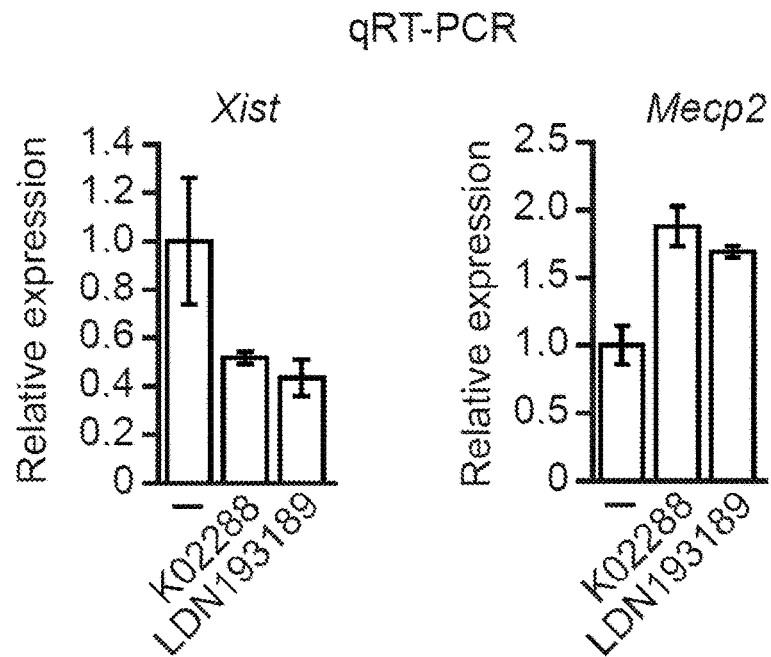

PDPK1 has a number of known substrates, which are themselves protein kinases, such as the family of serum- and glucocorticoid-inducible kinases (SGKs). FIG. 4D shows that treatment of BMLS2 cells with the SGK1/2 inhibitor GSK650394 resulted in loss of the Xist cloud and increased biallelic expression of Mecp2. Consistent with these results, qRT-PCR analysis shows that treatment of BMSL2 cells with GSK650394 resulted in a dose-dependent decrease in Xist expression and increase in Mecp2 expression (FIG. 4E). Similar results were obtained for two chemical inhibitors of another XCIF, ACVR1: K02288 and LDN193189 (FIGS. 4F and 4G).

Figure 4H:
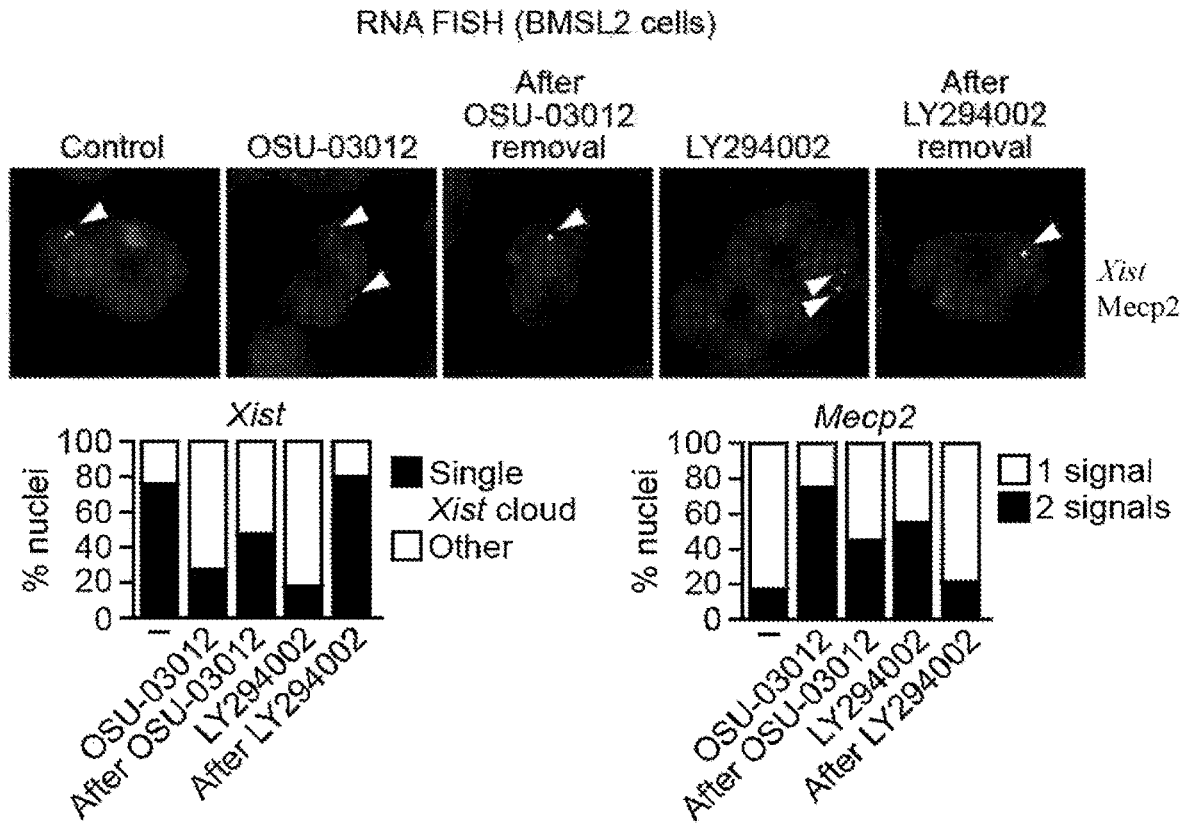
Figure 11C:
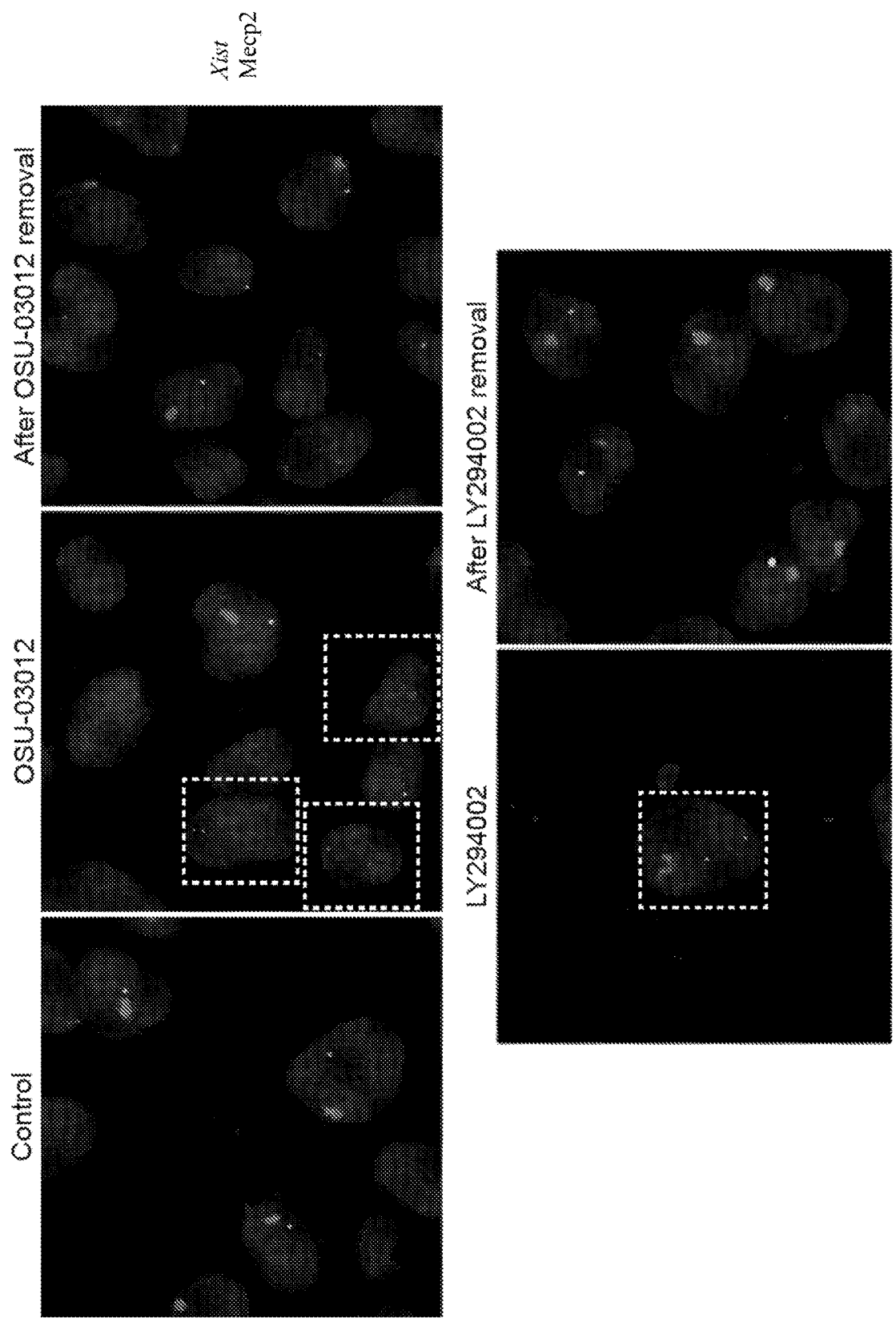

BMSL2 cells were treated with PDPK1 inhibitor OSU-03012 or PI3K inhibitor LY294002 resulting in biallelic expression of the Xi-linked Mecp2 gene (FIG. 4H and FIG. 11C). Following removal of the drug for at least six days, normal Xist expression and localization, and monoallelic expression of Mecp2, was largely restored, indicating that small molecule-mediated reactivation of Xi-linked genes is reversible.

Figure 4I:
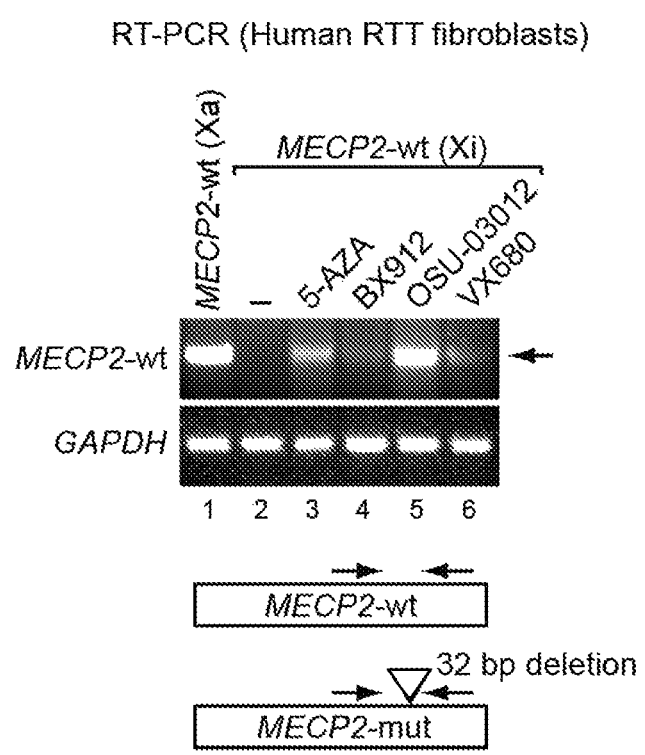

In a clonal fibroblast cell line from an RTT patient, the Xa-linked mutant MECP2 allele contains a 32 bp deletion, enabling selective detection of Xi-linked wild-type MECP2 mRNA in an RT-PCR assay using a primer within the deleted region. Another clonal fibroblast cell line derived from the same RTT patient in which the wild-type MECP2 allele is on the Xa provided a control for the correct RT-PCR product (FIG. 4I, lane 1). The results show, as expected, that the Xi-linked wild-type MECP2 allele was not expressed (lane 2) but could be reactivated by addition of the DNA methyltransferase inhibitor 5-azacytidine (lane 3). Significantly, addition of the PDPK1 inhibitors BX912 and OSU-03012 (lanes 4,5), or VX680 (lane 6), an inhibitor of AURKA, another XCIF (Table 1), reactivated the Xi-linked wild-type MECP2 allele. Thus, XCIF chemical inhibitors can reactivate the Xi-linked Mecp2/MECP2 gene in murine fibroblasts, ES cells and cortical neurons, as well as human RTT fibroblasts.

Example 6: Defective XCI in Female Stc1−/− Mice

Figure 5A:
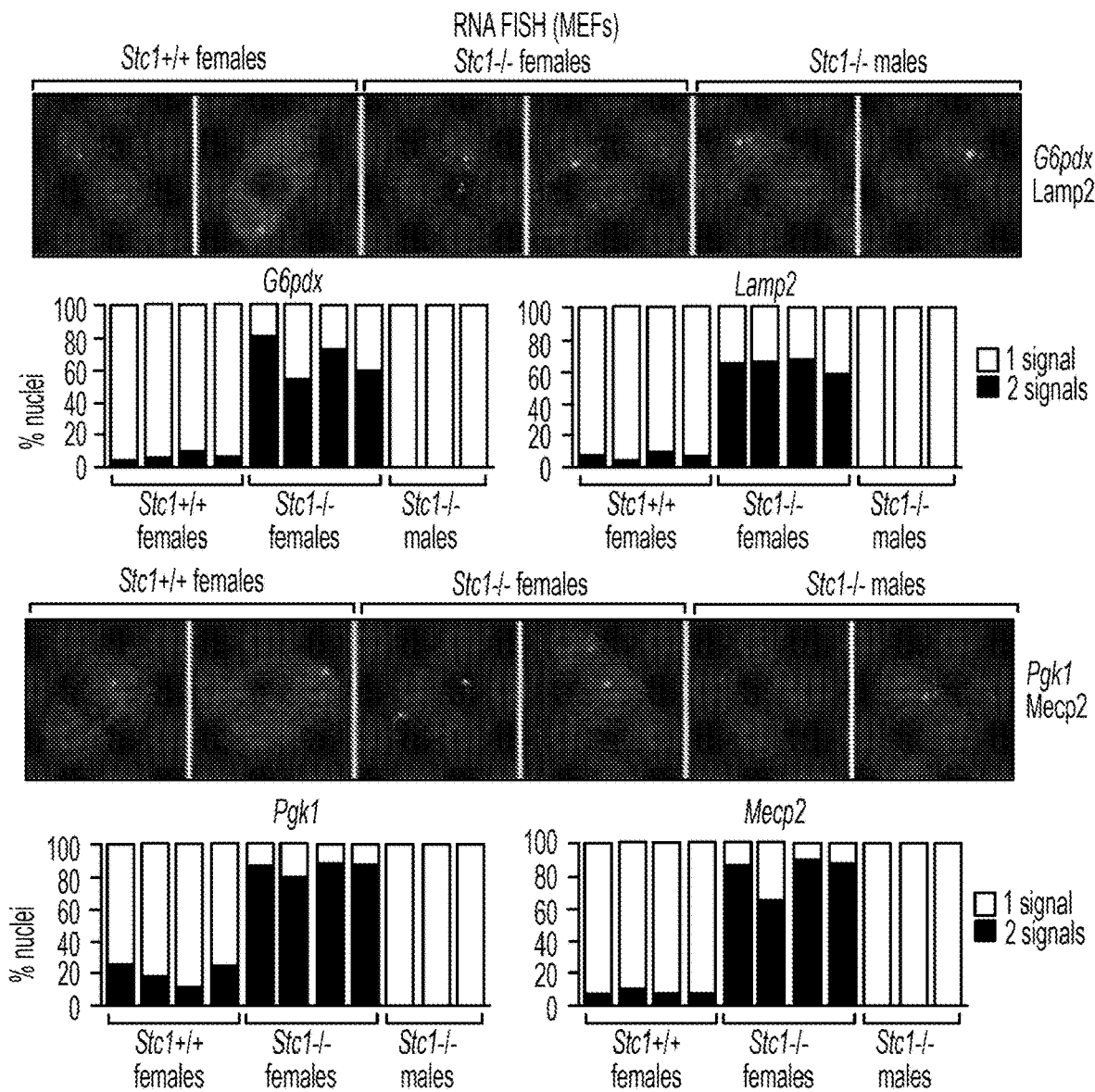
FIGS. 5A-5B show defective XCI in female Stc1−/− MEFs.
Figure 5B:
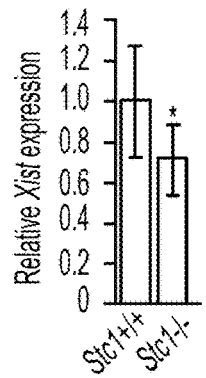
Figure 12A:
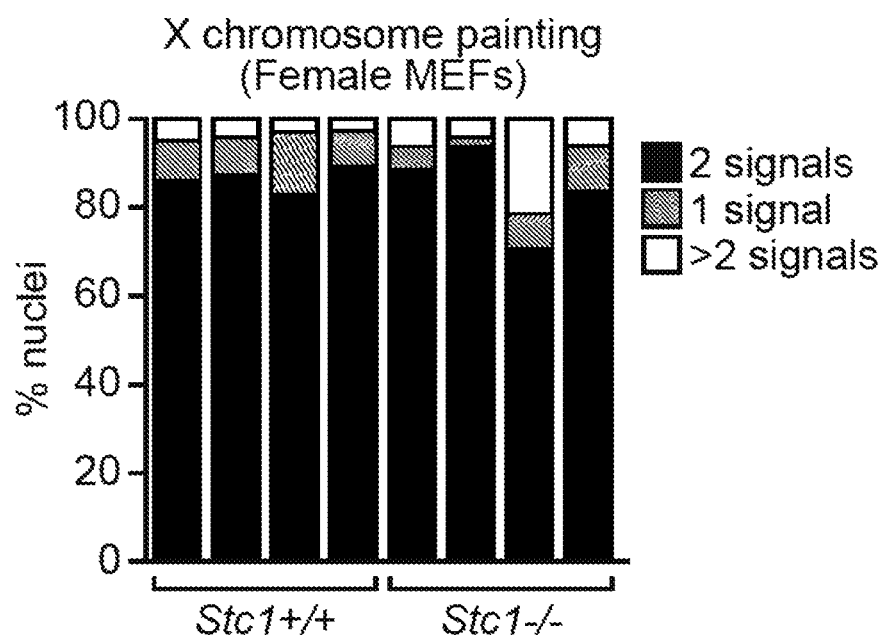
FIGS. 12A-12B show control experiment and RNA FISH images related to FIG. 5.

One of the XCIFs isolated in the screen, STC1, is a glycoprotein found in both the cytoplasm and nucleus. Stc1−/− mice have no obvious phenotype and litters have the expected Mendelian and male:female ratios. To determine whether STC1 is involved in XCI in the mouse, Stc1+/− mice were intercrossed and the MEFs from the resultant progeny were analyzed by two-color RNA FISH for expression of G6pdx, Lamp2, Pgk1 and Mecp2. As expected, female Stc1+/+ MEFs, and as a control male Stc1−/− MEFs, displayed monoallelic expression of G6pdx, Lamp2, Pgk1 and Mecp2 (FIG. 5A). By contrast, female Stc1−/− MEFs predominantly displayed biallelic expression of the four genes, indicative of an XCI defect. qRT-PCR analysis revealed reduced Xist levels in female Stc1−/− MEFs compared to female Stc1+/+ MEFs (FIG. 5B). Notably, the X chromosome content of female Stc1−/− and Stc1+/+ MEFs was comparable (FIG. 12A).

Figure 12B:
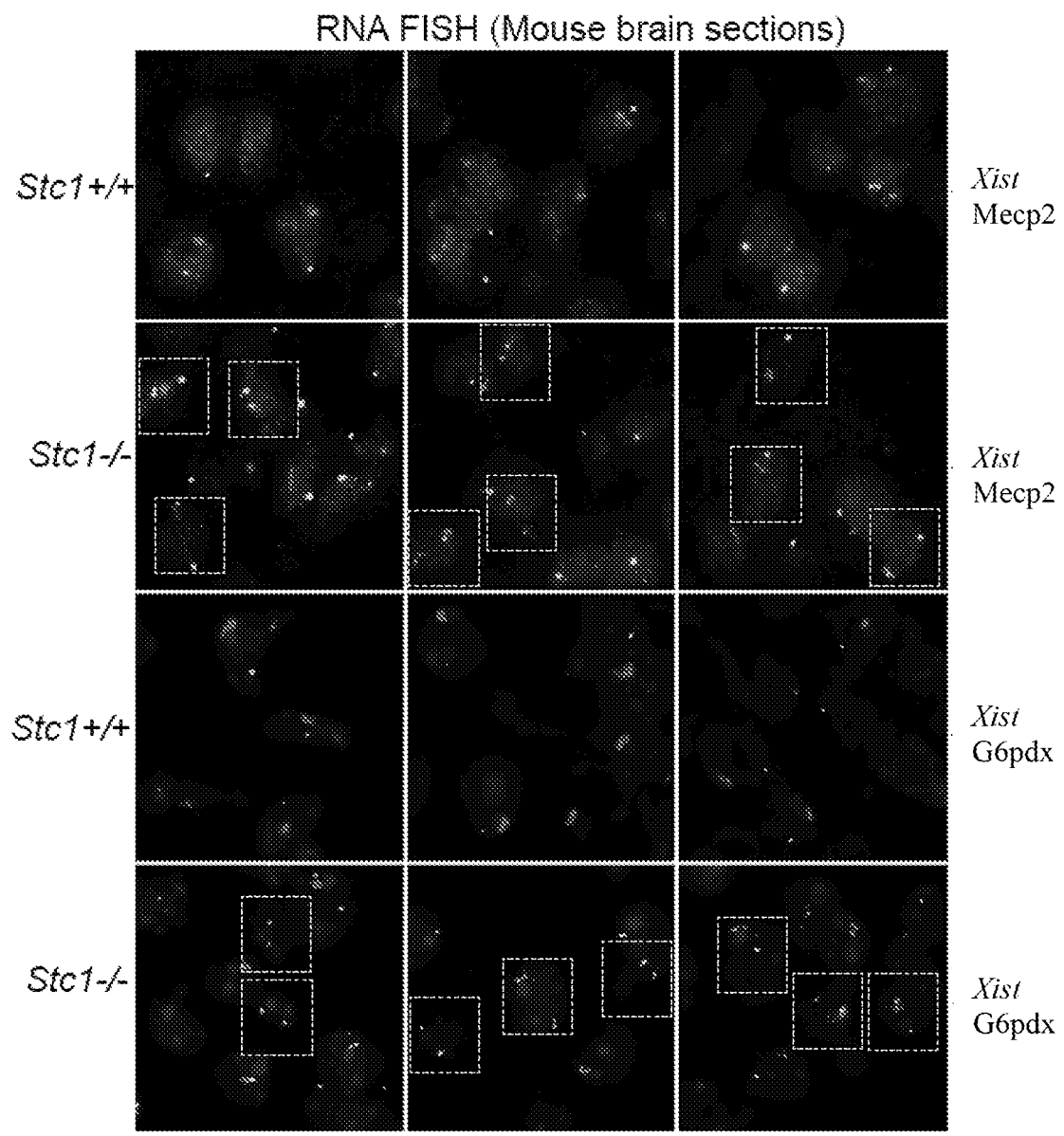

To further validate these findings, Xist and Mecp2, or Xist and G6pdx were analyzed in cortical neurons from brain sections of Stc1−/− and Stc1+/+ post-natal female mice. In female Stc1−/− mice, biallelic expression of Mecp2 and G6pdx was clearly evident in some cortical neurons (FIG. 12B). Again, in some cells the colocalization of Mecp2 and Xist, or G6pdx and Xist signals were observed, indicative of reactivation of the Xi-linked Mecp2 and G6pdx genes.

Figure 6A:
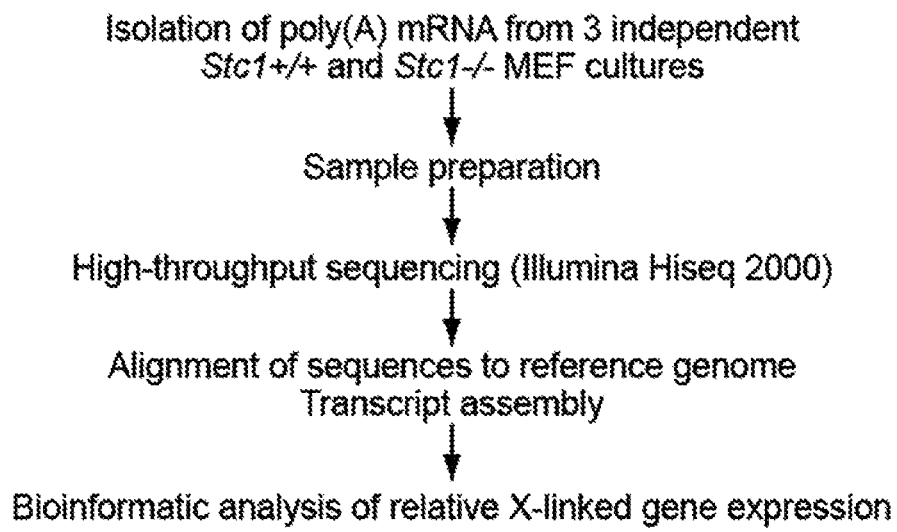
FIGS. 6A-6G show defective XCI in female Stc1−/− mice is not accompanied by increased X-linked gene expression.
Figure 6B:
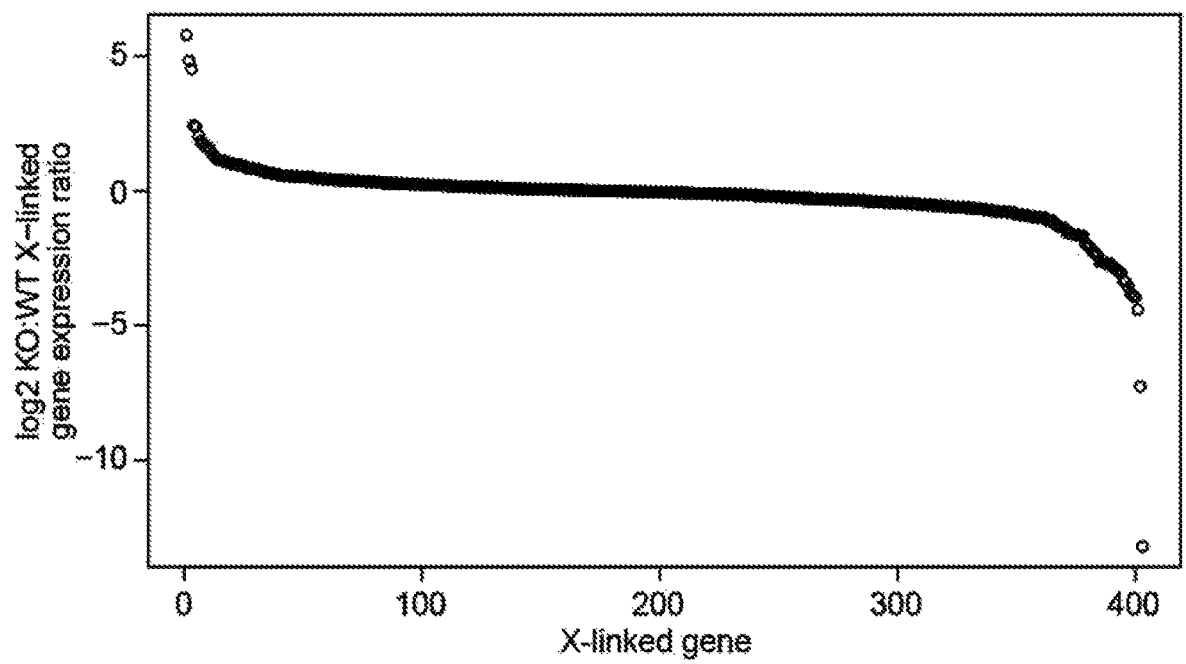
Figure 6C:
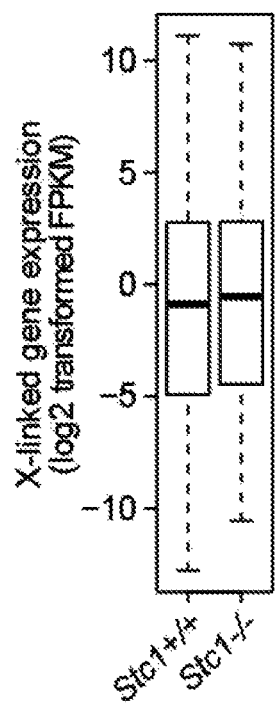
Figure 13A:
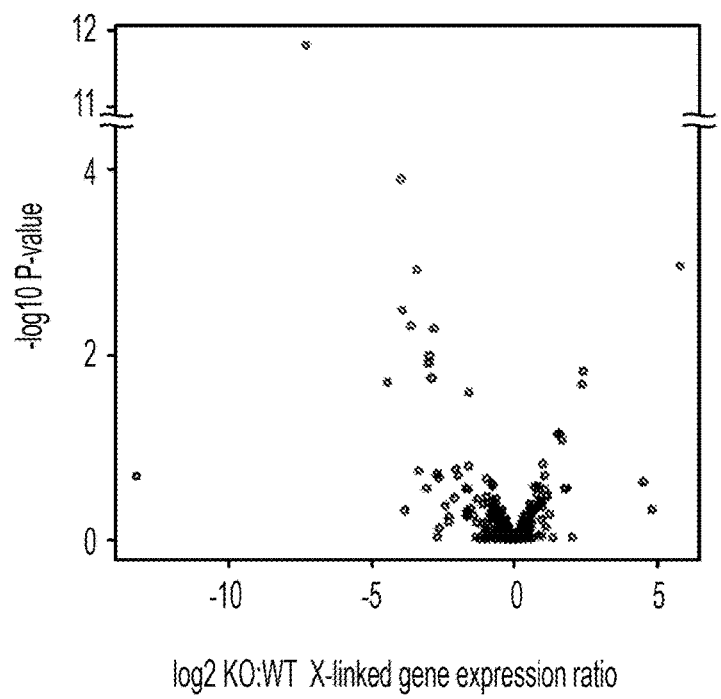
Figure 13B:
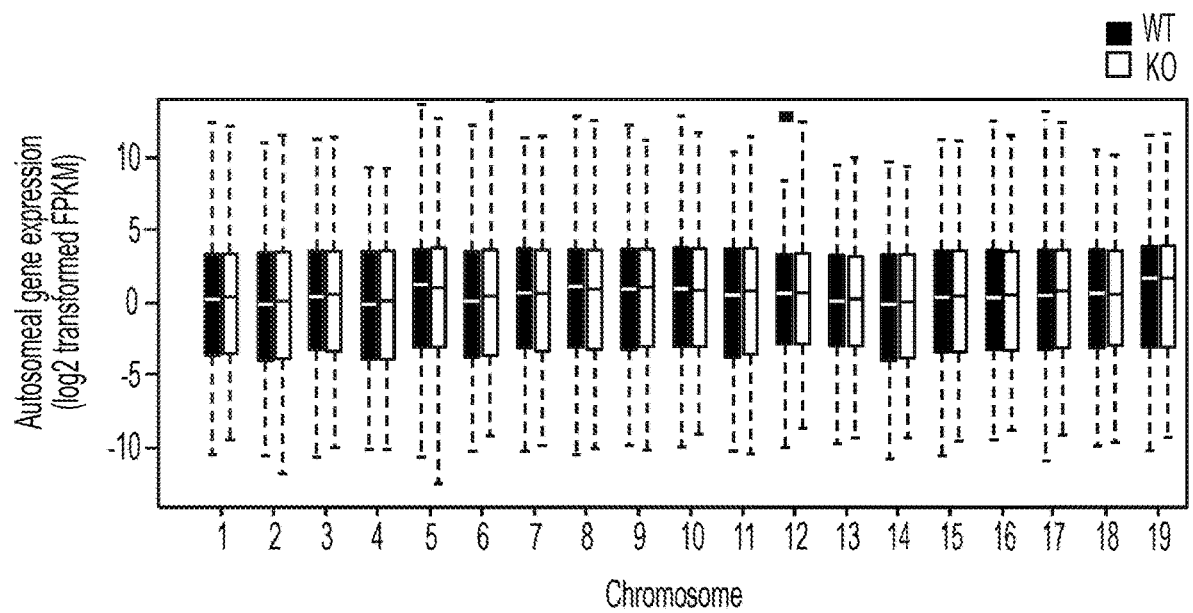
Figure 13C:
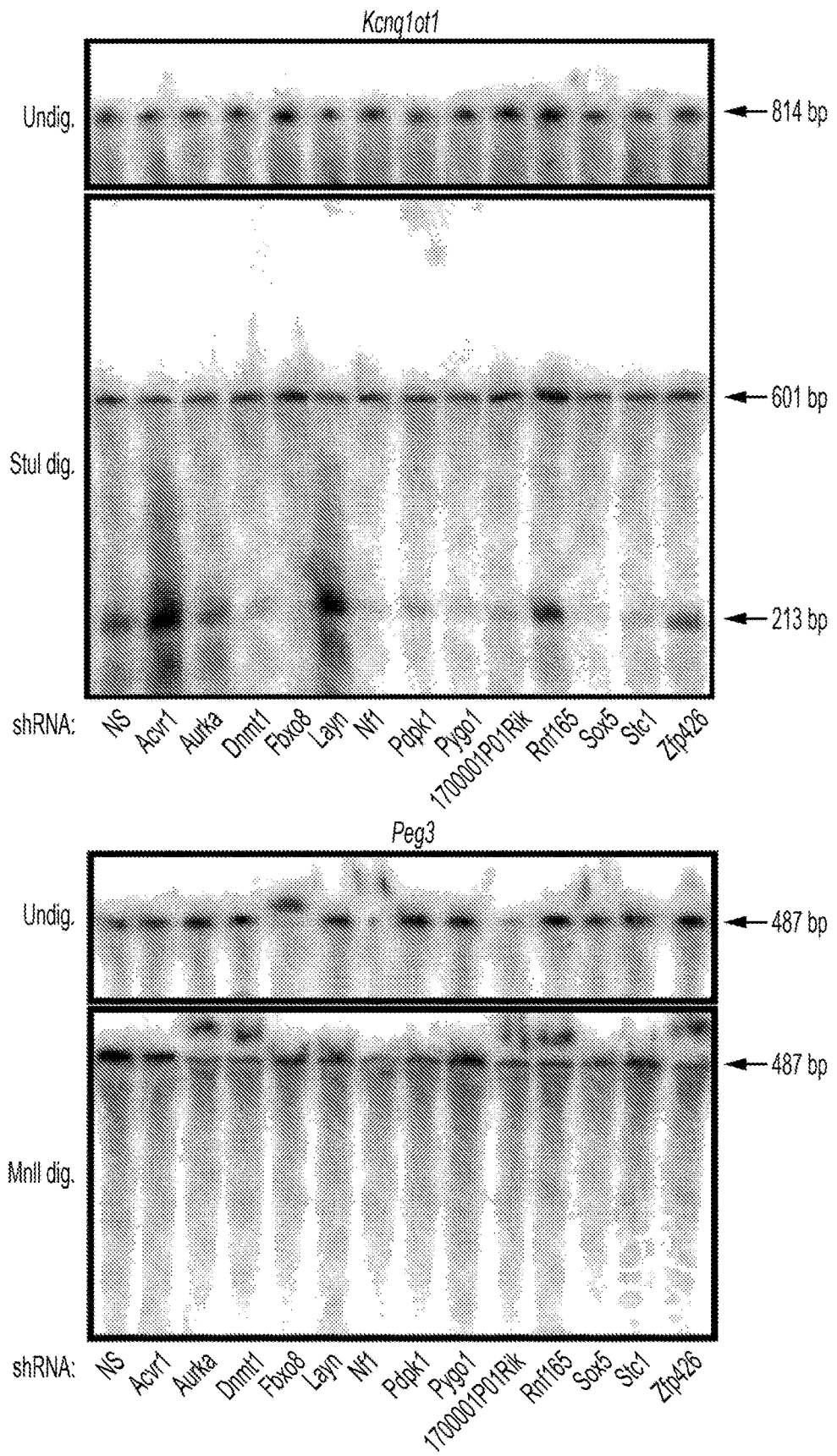
Figure 13C:
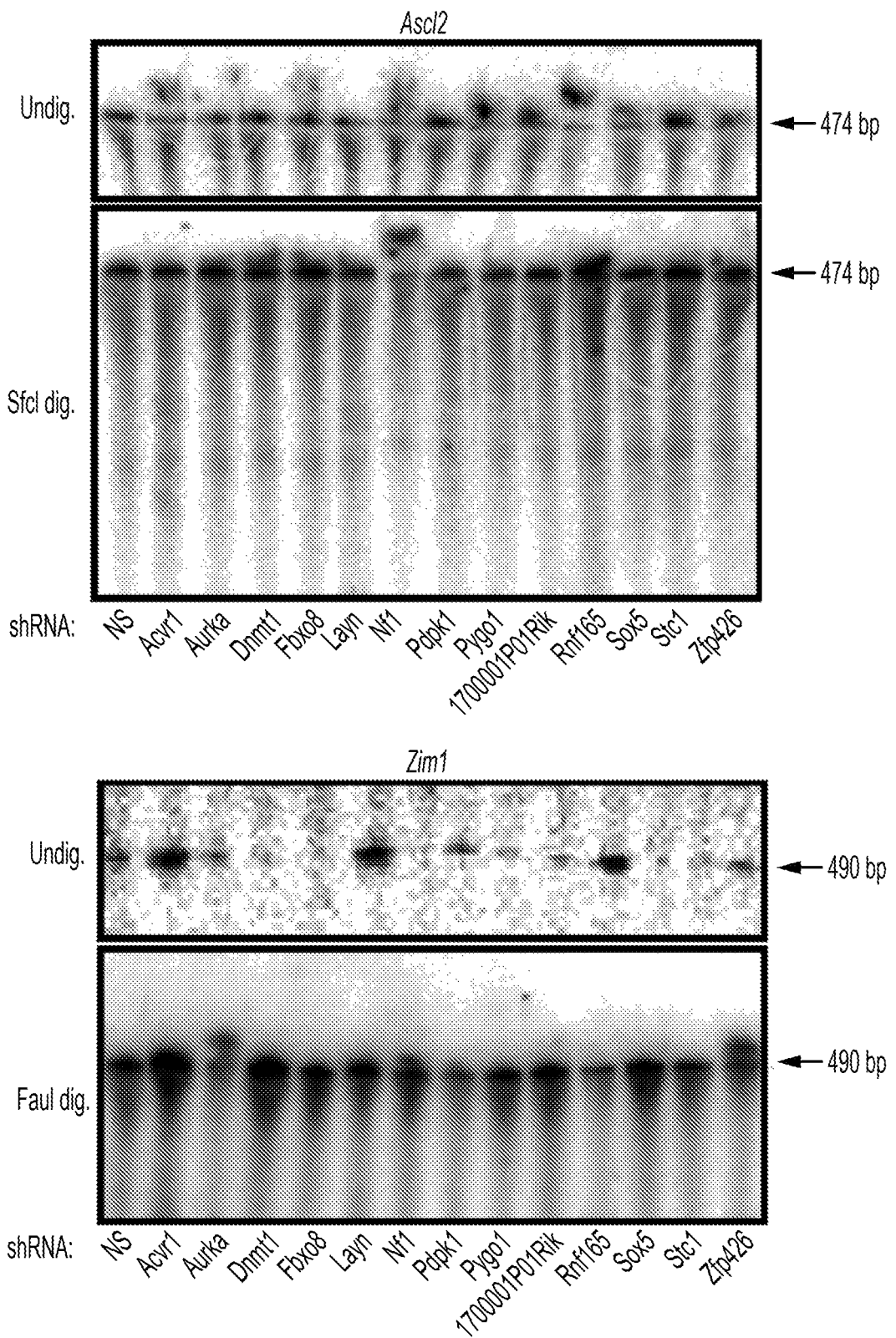

Example 7: Defective XCI in Female Stc1−/− Mice is not Accompanied by Increased X-Linked Gene Expression Transcriptome profiling (RNA-Seq) experiments were performed to determine whether the expression levels of X-encoded genes were elevated in female Stc1−/− MEFs. In these experiments, RNA was prepared from three independent cultures of female Stc1+/+ or Stc1−/− MEFs. RNA samples were processed and amplified followed by high-throughput sequencing (Illumina Hiseq 2000) (FIG. 6A). Sequences were aligned to the reference genome and bioinformatic analysis of relative X-linked gene expression was performed. The results of FIG. 6B shows that total expression levels of the vast majority (98%) of X-linked genes were indistinguishable in Stc1+/+ and Stc1−/− MEFs. The similarity of X-linked gene expression between Stc1+/+ and Stc1−/− MEFs was statistically significant (FIG. 6C and FIG. 13A). Moreover, the vast majority (99%) of autosomal genes were also expressed at statistically comparable levels in female Stc1+/+ and Stc1−/− MEFs (FIG. 13B).

Figure 6D:
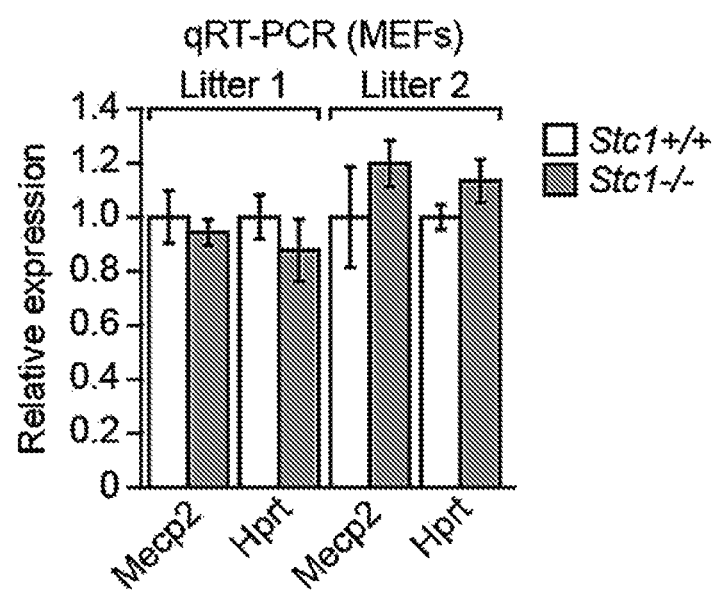
Figure 6E:
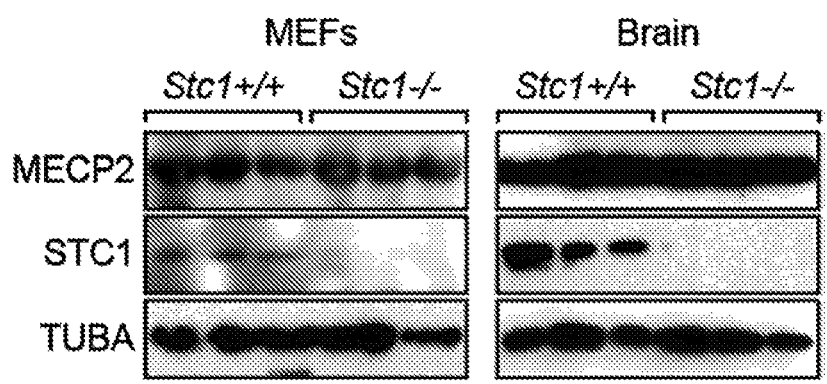

To support these RNA-seq-based results, the levels of X-linked genes Mecp2 and Hprt were analyzed by qRT-PCR. FIG. 6D shows that Mecp2 and Hprt mRNA levels were equivalent in female Stc1+/+ and Stc1−/− MEFs, despite deficient XCI. Furthermore, the immunoblot results of FIG. 6E show that the level of MECP2 protein in Stc1+/+ female MEFs (left) and brain lysates (right) was comparable to that in Stc1−/− females.

Figure 6F:
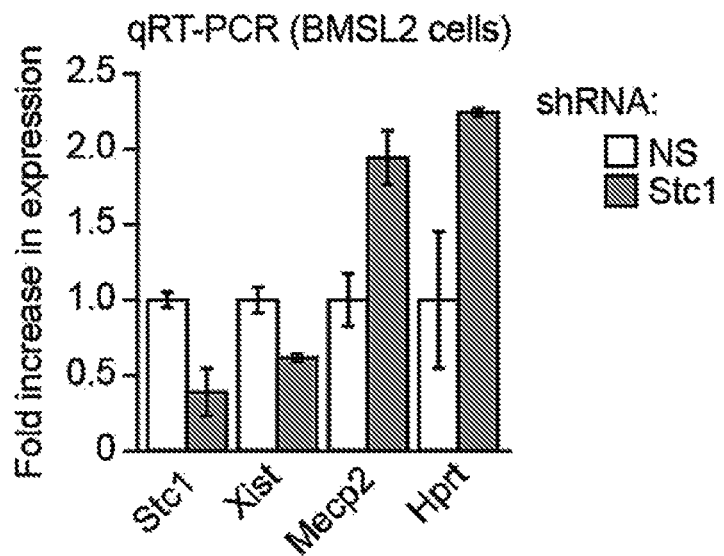
Figure 6G:
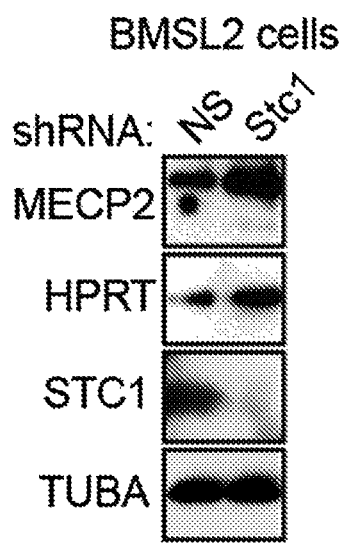

The experiments described above were performed in Stc1−/− mice in which there was a long-term, stable impairment of XCI. Long-term conditional depletion of Xist in mouse hematopoietic cells was shown to not be accompanied by a general increase in the expression of X-linked genes. To determine whether X-linked gene expression was increased immediately following abrogation of XCI, the expression of Mecp2 and Hprt was analyzed in mouse BMSL2 fibroblasts following shRNA-mediated knockdown of STC1. In STC1 KD BMSL2 cells there was an approximate two-fold increase in Mecp2 and Hprt expression, which was evident at both the mRNA (FIG. 6F and see FIG. 8B) and protein (FIG. 6G) level. Collectively, these results suggest the existence of a mechanism(s) that can compensate for a persistent XCI deficiency to regulate X-linked gene expression.

Example 8: Reactivation of the Xi-Linked Mecp2 Gene by Small Molecule Inhibition of Downstream Targets of PDPK1

Figure 14:
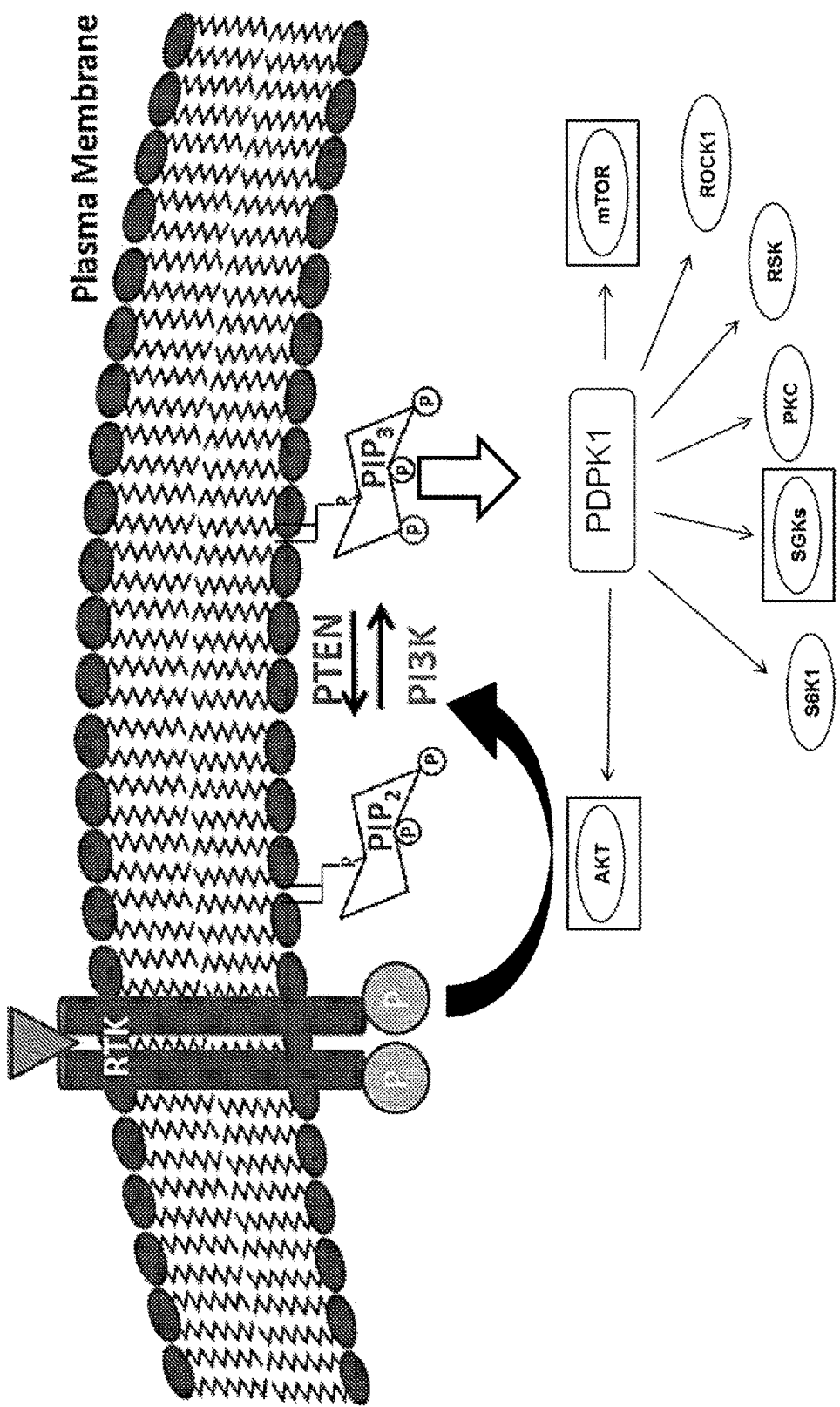
FIG. 14 shows a schematic diagram of downstream targets of 3-phosphoinositide dependent protein kinase-1 (PDPK1).
Figure 15:
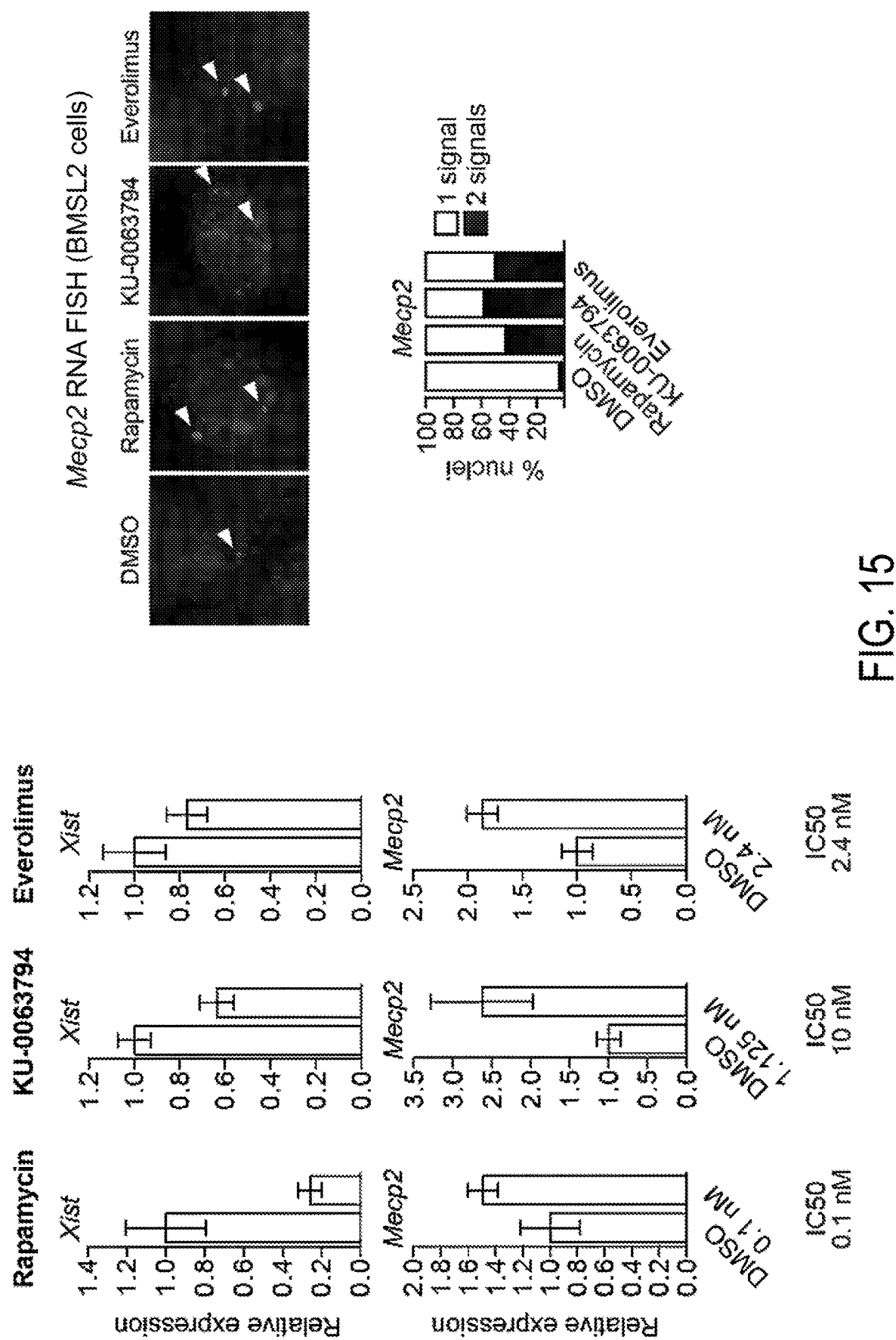
FIG. 15 shows treatment of mouse fibroblasts with an mTOR inhibitor reactivates the Xi-linked Mecp2 gene. Relative expression of Xist and Mecp2 in mouse fibroblasts was measured after treatment with rapamycin, KU-0063794, or everolimus (left). Mecp2 RNA was measured by fluorescence in situ hybridization (FISH) and percentage of nuclei stained was quantified (right).

One of the XCIFs is PDPK1, a serine-threonine kinase that regulates phosphatidylinositol-3-kinase (PI3K)/AKT signaling. PDPK1 has a number of known substrates, which are themselves protein kinases, such as mammalian target of rapamycin (mTOR), Aurora kinase A (AURKA), and Activin receptor type 1 (ACVR1), as shown in FIG. 14. This example describes treatment with inhibitors of downstream substrates of PDPK1 results in reactivation of Xi-linked genes (e.g., Mecp2).

mTOR is a serine-threonine protein kinase that is a downstream component in PI3K signaling pathways. Mouse fibroblasts were treated with three mTOR inhibitors (rapamycin, KU-0063794, or everolimus) and relative expression levels of Xist and Mecp2 were measured. Treatment with each mTOR inhibitor resulted in a decrease in the relative expression of Xist and an increase in relative expression of Mecp2, indicating reactivation of the Xi-linked Mecp2 gene (FIG. 15). The IC50 of rapamycin, KU-0063794, or everolimus, were measured at 0.1 nm, 10 nm, and 2.4 nm, respectively. Expression of Mecp2 was also analyzed by FISH in BMSL2 cells. Two Mcep2 signals were observed in cells treated with the mTOR inhibitor, indicating biallelic expression of Mcep2. Thus, treatment with each of the mTOR inhibitors reactivates Xi-linked Mcep2 (FIG. 15).

Figure 16:
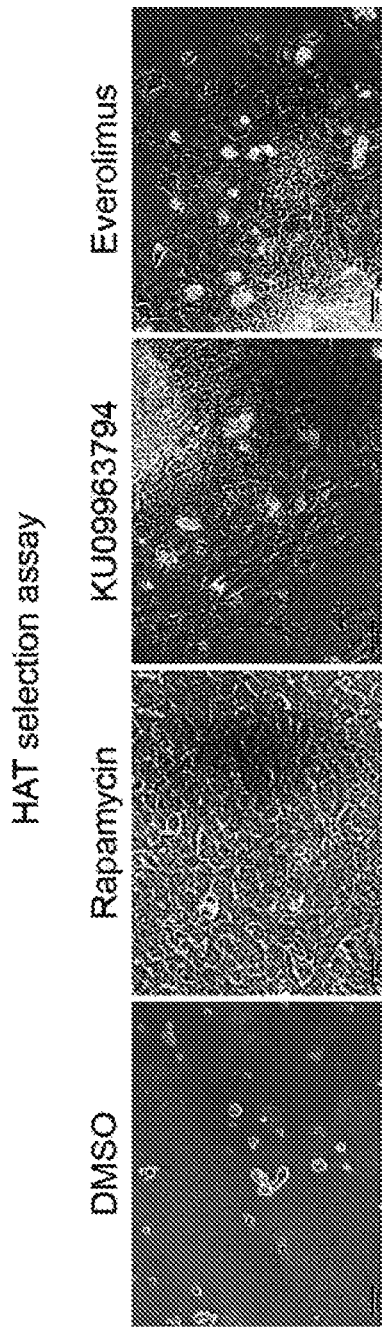
FIG. 16 shows treatment of mouse fibroblasts with an mTOR inhibitor (rapamycin, KU-0063794, everolimus) reactivates the Xi-linked Hprt gene, as measured by a hypoxanthine-aminopterin-thymidine (HAT) selection assay.

To confirm these results, a hypoxanthine-aminopterin-thymidine (HAT) selection assay was performed. The HAT assay is a dual selection assay that requires activation of the Xi-linked Hprt gene by an inhibitor with sufficiently low cytotoxicity to allow cellular proliferation and survival. Cells containing Xi-linked Hprt were treated with either DMSO (negative control), rapamycin, KU-0063794, or everolimus, and cellular growth was measured. Treatment with each mTOR inhibitor but not DMSO resulted in cellular growth, indicating that mTOR inhibitors reactivate Xi-linked Hprt gene (FIG. 16).

Aurora kinase A (AURKA) is a serine-threonine kinase that is associated with regulation of cell division in the G2-M phases and is a downstream substrate of PDPK1. The human Aurora kinase family comprises three members, Aurora kinase A (AURKA), B (AURKB), and C (AURKC). Here, the reactivation of Xi-linked genes using AURKA inhibitors (e.g., VX680, CD532, and MLN 8237) is described.

Figure 17:
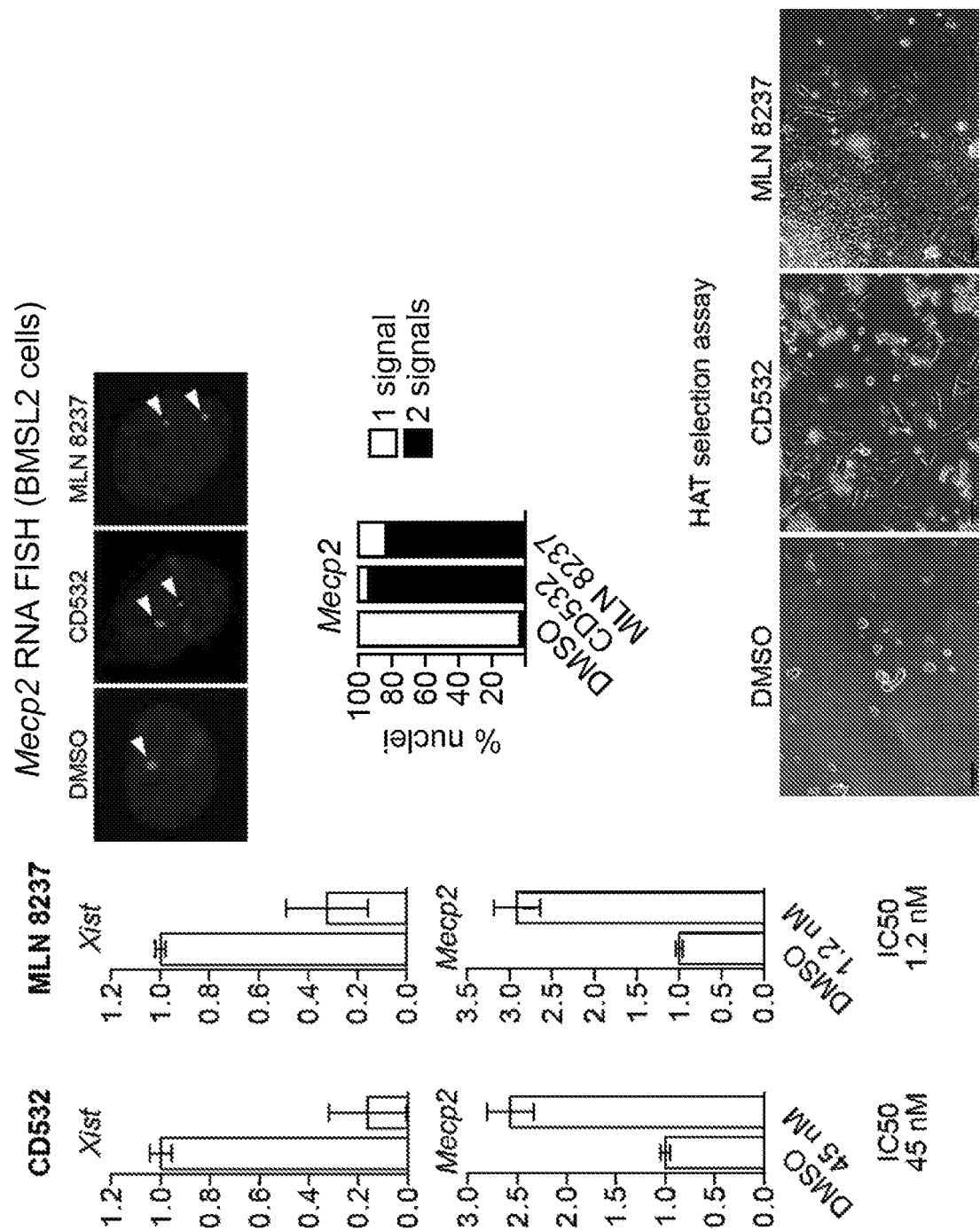
FIG. 17 shows inhibition of Aurora kinase A (AURKA) reactivates Xi-linked genes. Relative expression of Xist and Mecp2 in mouse fibroblasts was measured after treatment with CD532 and MLN8237. Mecp2 RNA was measured by fluorescence in situ hybridization (FISH) and percentage of nuclei stained was quantified (right). Results were confirmed using a HAT selection assay.

Mouse fibroblasts were treated with CD532 or MLN 8237 (which have greater selectivity for AURKA than VX680) and relative expression levels of Xist and Mecp2 were measured. Treatment with each AURKA inhibitor resulted in a decrease in the relative expression of Xist and an increase in relative expression of Mecp2, indicating reactivation of the Xi-linked Mecp2 gene (FIG. 17). The IC50 of CD532 and MLN 8237 were 45 nm and 1.2 nm, respectively. Expression of Mecp2 was also analyzed by FISH in BMSL2 cells. Two Mcep2 signals were observed in cells treated with the AURKA inhibitors, indicating biallelic expression of Mcep2. Results were confirmed using HAT selection assay. Thus, treatment with each of the AURKA inhibitors reactivates Xi-linked Mecp2 (FIG. 17).

Activin receptor type 1 (ACVR1, also known as ALK2) is a receptor serine-threonine kinase that mediates signaling by bone morphogenic proteins. ACVR1 is a downstream substrate of PDPK1. Here, reactivation of Xi-linked genes using ACVR1 inhibitors (e.g., K02288, dorsomorphin, and LDN193189) is described.

Figure 18:
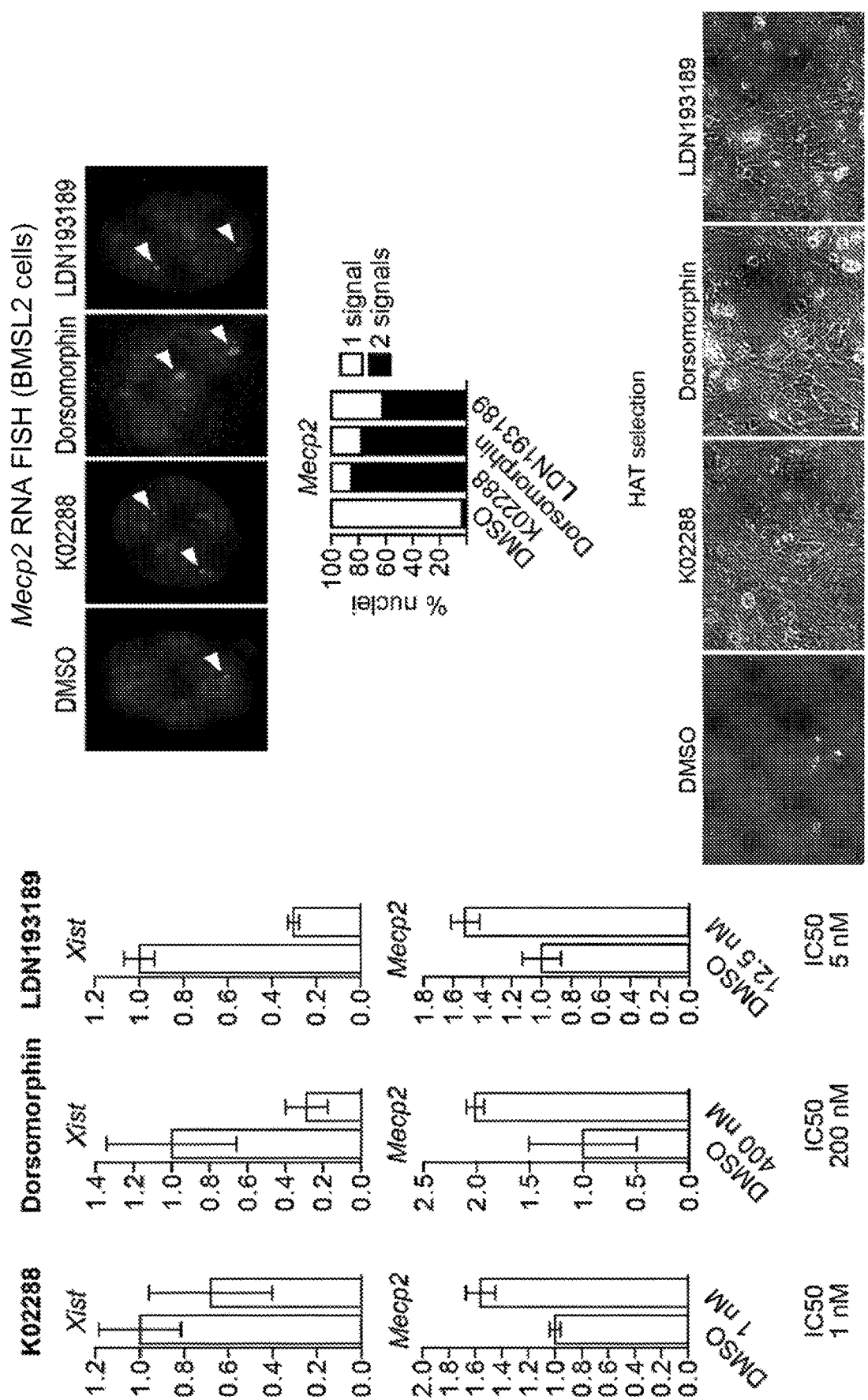
FIG. 18 shows treatment of mouse fibroblasts with Activin Receptor Type 1 (ACVR1) inhibitor reactivates Xi-linked genes. Relative expression of Xist and Mecp2 in mouse fibroblasts was measured after treatment with K02288, dorsomorphin, or LDN193189. Mecp2 RNA was measured by fluorescence in situ hybridization (FISH) and percentage of nuclei stained was quantified (right). Results were confirmed using a HAT selection assay.

Mouse fibroblasts were treated with K02288, dorsomorphin, or LDN193189 and relative expression levels of Xist and Mecp2 were measured. Treatment with each ACVR1 inhibitor resulted in a decrease in the relative expression of Xist and an increase in relative expression of Mecp2, indicating reactivation of the Xi-linked Mecp2 gene (FIG. 18). The IC50 of K02288, dorsomorphin, and LDN193189 were 1 nm, 200 nm, and 5 nm, respectively. Expression of Mecp2 was also analyzed by FISH in BMSL2 cells. Two Mcep2 signals were observed in cells treated with the ACVR1 inhibitors, indicating biallelic expression of Mcep2. Results were confirmed using HAT selection assay. Thus, treatment with each of the ACVR1 inhibitors reactivates Xi-linked Mecp2 (FIG. 18).

Example 9: CRISPR/Cas9-Based Screen to Identify New XCIFs

A CRISPR/Cas9-based screen has been conducted to identify new XCIFs. First, BMSL2 cells, female mouse fibroblasts stably expressing Cas9 and selected for blasticidin resistance, were infected with a mouse GeCKO v2 CRISPR library (including 100,000 guide RNAs) and then selecting for puromycin resistance. Next, the clones were subjected to HAT selection for one week. Reactivation of X chromosomes is caused by CRISPR-mediated inactivation of an XCIF. Growth in HAT medium results from expression of functional HPRT from a reactivated X chromosome. Guide RNAs were identified and validated from positive clones.

Example 10: Materials and Methods

Cell Culture

H4SV cells, BMSL2 (HOBMSL2) cells and human RTT fibroblasts were cultured as recommended by the supplier. PGK12.1 cells were cultured as previously described and differentiated by replating, on gelatinized plastic dishes, in the presence of 100 nM alpha-retinoic acid (Sigma) and absence of leukemia inhibitory factor for at least one week.
Isolation of MEFs, Brain Tissue and Cortical Neurons MEFs were isolated from E8.5 (Dnmt1 mice; Jackson Laboratories) or E14.5 (Stc1mice, provided by D. Sheikh-Hamad) embryos, and were PCR genotyped using gene-specific and SRY primers (Table 2). Stc1+/+ and Stc1-/- P1 pup heads were embedded in O.C.T. compound (Tissue-Tek) and frozen in liquid nitrogen. Brain tissue cryo-sections (5 μm thick) were mounted, fixed and hybridized with FISH probes as described. Neurons were isolated from the cerebral cortexes of E19.5 C57BL/6 embryos and cultured as described.

Large-Scale shRNA Screen and Validation

The mouse shRNA$^{mir}$ library (release 2.16; Open Biosystems/Thermo Scientific) was obtained. H4SV cells (1.1× $10^6$) were transduced at a multiplicity of infection of 0.2 with the retroviral pools, generated as previously described, and selected for resistance to puromycin for 7 days. Cells were FACS sorted and GFP-positive cells were selected. Candidate shRNAs were identified as described previously. To validate the candidates, 3×$10^5$ H4SV or BMSL2 cells were transduced with single shRNAs and puromycin selected for 4 days. For HAT selection, 3×$10^5$ cells were plated in 6-well plates and selected in medium containing 1× HAT (GIBCO) for 1 week, followed by live cell imaging using a Zeiss Axiovert 200 microscope.

RNA FISH

RNA FISH experiments were performed (see Table 2 for cDNA template sources for probes). Cells were visualized on a Leica DM IRE2 confocal microscope. For quantification, 100-500 cells total from at least 10 different fields were counted and scored; only cells with a detectable RNA FISH signal were included in the analysis, with the exception of the experiment in FIG. 3A Images were adjusted consistently for contrast and brightness using AxioVision Software (Zeiss). All RNA-FISH experiments were performed at least twice, and representative images and quantification are shown from one experiment.

Alkaline Phosphatase Assay

ES cells were treated in the presence or absence of retinoic acid (see above) and analyzed using an Alkaline Phosphatase Staining Kit (Stemgent).

Quantitative Real-Time RT-PCR (qRT-PCR)

Total RNA was isolated and reverse transcribed using Superscript II Reverse Transcriptase (Invitrogen). qRT-PCR was performed as described previously using primers listed in Table 2. For the experiments shown in FIGS. 3F and 3H and FIGS. 10B and C, strand specific cDNA synthesis of Xist and/or Tsix RNAs was performed as described previously, and expression of Xist and Tsix were normalized to that of Gapdh.

Locked Nucleic Acid (LNA) Nucleofection

Cy3-labeled Xist and control (scrambled) LNAs were added to $10^4$ BMSL2 cells at a final concentration of 1 μM in OptiMem using Lipofectamine (Invitrogen) every 6-8 hr for 48 hr.

ChIP Assay

ChIP assays were performed as described previously using extracts prepared 7 days post-retroviral transduction and puromycin selection, and antibodies against DNMT1 or POL2 (Abcam). Primer sequences used for amplifying ChIP products are listed in Table 2.

Nuclear Run-on Assay

Assays were performed in the presence of [$P^{32}$]UTP, and radioactive RNA was isolated using TRIzol reagent. Samples were hybridized to a nylon membrane immobilized with cDNA probes to Xist (prepared from a plasmid containing Xist exons 1 and 6; (51)), Hprt (prepared from a plasmid containing the Hprt coding region PCR-amplified using forward 5'-TCCGCCTCCTCCTCTGCT-3' (SEQ ID NO: 114) and reverse 5'-GGGAATTTATTGATTTGCAT-3' (SEQ ID NO: 115) (primers) and Tbp (prepared from a cloned Tbp cDNA; Open Biosystems). After washing the membranes, filters were exposed to a PhosphorImager screen and the signal was quantified on a Fujifilm FLA-7000 imaging system using Image Gauge V4.22 Software.

Xist RNA Stability Assay

After treatment with DNase (Ambion), strand-specific Xist RNA levels, and as a control Actin, were quantified by qRT-PCR (see Table 2 for primer sequences).

Chemical Inhibitor Treatment

Differentiated mouse ES or BMSL2 cells were treated with dimethyl sulfoxide (DMSO), LY294002 (Cayman Chemicals; 4 or 10 µM), OSU-03012 (Selleck Chemicals; 2.5 or 4 µM), GNE-317 (Genentech Inc., 1.25, 2.5 or 5 µM), GSK650394 (Tocris Bioscience, 5 µM), K02288 (Cayman Chemical, 0.5 µM), or LDN192189 (Cayman Chemical, 0.5 µM) for 3 days prior to RNA FISH analysis. For XCI reversibility experiments, BMSL2 cells were treated with 8 µM LY294002 or 2.5 µM OSU-03012 for 3 days, washed twice with PBS, and then the media was replaced with fresh media every day for at least 5 days prior to RNA FISH analysis.

Mouse cortical neurons, isolated as described above, were treated with DMSO, 5 µM BX912 (Axon Medchem), 0.4 µM LY294002 or 2.5 µM OSU-03012 for 4 days prior to RNA FISH analysis.

RTT fibroblasts were treated with either DMSO, 5-azacytidine (Calbiochem; 10 µM for 3 days), BX912 (10 µM for 3 days), OSU-03012 (10 µM for 2 days followed by 5 µM for 1 day) or VX680 (ChemieTek; 10 µM for 2 days followed by 3 µM for 1 day). The wild-type MECP2 levels were analyzed as using primers listed in Table 2.

RNA Sequencing and Data Analysis

Total RNA was isolated from MEFs from Stc1+/+ and Stc1−/− embryos (n=3 for each genotype) using the RNeasy Plus Mini Kit (Qiagen) and treated with RNase-free DNase I (Qiagen). mRNA libraries were generated as described in the TruSeq RNA sample preparation guide (Illumina).

Libraries were sequenced as 50-bp paired ends using an Illumina HiSeq 2000. Raw reads (ranging from 47-92 million reads per sample) were trimmed by removing adaptor sequences and demultiplexed with barcodes. Reads with ambiguous nucleotides and Phred quality scores <46 were removed before assembly. Paired-end sequencing reads were aligned using TopHat (v2.0.6) against mouse genome assembly NCBI38/mm10 (downloaded from pre-built indexes at bowtie-bio.sourceforge.net/) by default parameters, with the exception of expecting an inner distance between mate pairs of 75 bp instead of the default value of 50 bp. The reads aligned by TopHat were processed by Cufflinks (v2.0.1) to assemble transcripts and to measure their relative abundances in FPKM units (fragments per kilobase of exon per million fragments mapped). Assembled transcripts from control and knockout samples were compared with the transcriptome downloaded from Ensembl.org and tested for differential expression using the Cuffcompare and Cuffdiff utilities in the Cufflinks package. Cuffdiff was run with classic-FPKM normalization and a false discovery rate (FDR) threshold of 0.05. Genes with a >2-fold change in expression between Stc1+/+ and Stc1−/− samples and P<0.05 (calculated using Cufflinks) were considered significant.

The gene expression results measured by Cufflinks were annotated based on a GTF file downloaded from Ensembl.org using Bioconductor package ChIPpeakAnno (55). All figures were plotted using R/Bioconductor (v2.15.2) software. The RNA-Seq data have been deposited in NCBI's Gene Expression Omnibus (56) and are accessible to reviewers through GEO Series accession number GSE47395 (ncbi.nlm.nih.gov/geo/query/acc.cgi?token=jtslncmggoemsro&acc=GSE47395).

Immunoblotting

Cell extracts were prepared and immunoblots proved using antibodies against HPRT (Abcam), MECP2 (Abcam), STC1 (Santa Cruz Biotechnology) and α-tubulin.

Single Nucleotide Primer Extension (SNuPE) Assay

A SNuPE assay for Pgk1 was carried out using a Taqman SNP genotyping assay (Applied Biosystems) according to the manufacturer's specifications. The following primers and reporters were used for the assay: 5'-CCGGCCAAAAT-TGATGCTTTCC-3' (SEQ ID NO: 116), 5'-CAGTC-CCAAAAGCATCATTGACAT-3' (SEQ ID NO: 117), 5'-CACTGTCCAAACTAGG-3' (SEQ ID NO: 118) and 5'-CACTGTCCACACTAGG-3' (SEQ ID NO: 119). The data are plotted as the function of ΔRn for each sample, which represents the reporter fluorescence for each allele (VIC/FAM) normalized to the passive reference dye.

Imprinted Gene Analysis

Mouse embryonic fibroblasts from strain C57BL6 (CAST 7), provided by M. Bartolomei, were cultured in DMEM supplemented with 10% fetal calf serum and 10% NEAA. Analysis of imprinted genes was performed using mouse embryonic fibroblasts isolated from the C57BL/6 (CAST7) strain, which contains chromosome 7 from the *Mus castaneus* (Cast) strain in a C57BL/6 background. Briefly, total RNA was extracted and cDNA synthesis was carried out as described above. For PCR amplification, the cDNA was added to Ready-To-Go PCR Beads (GE Life Sciences) together with 0.3 µM gene-specific primers (Table 2). Expression of the imprinted gene was analyzed by allele-specific restriction enzyme digestion (StcI for Ascl2, StuI for Kcnq1ot1, MnlI for Peg3, and FauI for Zim1) and digested PCR products were resolved by polyacrylamide gel electrophoresis.

TABLE 2

List of primers used for qRT-PCR and RT-PCR analysis, cDNA synthesis, ChIP assays, and mouse genotyping; oligo ID numbers for shRNAs; and cDNAs used to prepare RNA FISH probes.

| Primers | | |
|---|---|---|
| qRT-PCR | Forward primer (5'→3') | Reverse primer(s) (5'→3') |
| Actin | TTGCCGACAGGATGCAGAA (SEQ ID NO: 1) | GCCGATCCACACGGAGTACT (SEQ ID NO: 43) |
| Acyr1 (mouse) | GGCCAGCAGTGTTTTTCTTC (SEQ ID NO: 2) | TTCCCCTGCTCATAAACCTG (SEQ ID NO: 44) |

TABLE 2-continued

List of primers used for qRT-PCR and RT-PCR analysis, cDNA synthesis, ChIP assays, and mouse genotyping; oligo ID numbers for shRNAs; and cDNAs used to prepare RNA FISH probes.

| | | |
|---|---|---|
| ACVR1 (human) | TCAGGAAGTGGCTCTGGTCT (SEQ ID NO: 3) | CGTTTCCCTGAACCATGACT (SEQ ID NO: 45) |
| Aurka (mouse) | TAGGATACTGCTTGTTACTT (SEQ ID NO: 4) | CCTCCAACTGGAGCTGTA (SEQ ID NO: 46) |
| AURKA (human) | TGGAATATGCACCACTTGGA SEQ ID NO: 5 | ACTGACCACCCAAAATCTGC (SEQ ID NO: 47) |
| Bmi1 | AAATCAGGGGGTTGAAAAATCT (SEQ ID NO: 6) | GCTAACCACCAATCTTCCTTTG (SEQ ID NO: 48) |
| Cdx2 | GCCAAGTGAAAACCAGGACAAAAGAC (SEQ ID NO: 7) | GCTGCTGTTGCTGCTGCTGCTTC (SEQ ID NO: 49) |
| Dnmt1 (mouse) | GGAAGGCTACCTGGCTAAAGTCAAG (SEQ ID NO: 8) | ACTGAAAGGGTGTCACTGTCCGAC (SEQ ID NO: 50) |
| DNMT1 (human) | GTGGGGGACTGTGTCTCTGT (SEQ ID NO: 9) | TGAAAGCTGCATGTCCTCAC (SEQ ID NO: 51) |
| Eomes | CCTGGTGGTGTTTTGTTGTG (SEQ ID NO: 10) | TTTAATAGCACCGGGCACTC (SEQ ID NO: 52) |
| Ezh2 | CTAATTGGTACTTACTACGATAACTTT (SEQ ID NO: 11) | ACTCTAAACTCATACACCTGTCTACAT (SEQ ID NO: 53) |
| Fbxo8 (mouse) | GCTGAGCCATTTTCTTCTCG (SEQ ID NO: 12) | ATGATGGTTTCTGGCCACTC (SEQ ID NO: 54) |
| FBXO8 (human) | CAAGGGTTGTGGAGAGTGGT (SEQ ID NO: 13) | ATGTCAATGCCTCCTTGGAC (SEQ ID NO: 55) |
| Gapdh | ATGGCCTTCCGTGTTCCTAC (SEQ ID NO: 14) | ATAGGGCCTCTCTTGCTCAG (SEQ ID NO: 56) |
| G6pdx | TCAAAGCACACGCCCTCTT (SEQ ID NO: 15) | TAGCGCACAGCCAGTTTCC (SEQ ID NO: 57) |
| Hprt | AAGCTTGCTGGTGAAAAGGA (SEQ ID NO: 16) | TTGCGCTCATCTTAGGCTTT (SEQ ID NO: 58) |
| Layn (mouse) | GCAAGGAGAGTGGATGGGTA (SEQ ID NO: 17) | ACTTGTGATGCTGTGCTTGC (SEQ ID NO: 59) |
| LAYN (human) | CTACAGGCCGTGCTGCTG (SEQ ID NO: 18) | CTGACTAGCTGGCCTCCATC (SEQ ID NO: 60) |
| Mecp2 | CATGGTAGCTGGGATGTTAGG (SEQ ID NO: 19) | GCAATCAATTCTACTTTAGAGCG (SEQ ID NO: 61) |
| Nf1 (mouse) | GTAGCCACAGGTCCCTTGTC (SEQ ID NO: 20) | CTGAGAACAAGTACACAGAGAGTGA (SEQ ID NO: 62) |
| NF1 (human) | AATTCTGCCTCTGGGGTTTT (SEQ ID NO: 21) | GCTGTTTCCTTCAGGAGTCG (SEQ ID NO: 63) |
| Oct4 | CTCACCCTGGGCGTTCTCT (SEQ ID NO: 22) | AGGCCTCGAAGCGACAGA (SEQ ID NO: 64) |
| Pdpk1 (mouse) | GGTCCAGTGGATAAGCGAAA (SEQ ID NO: 23) | TTTCTGCACCACTTGTGAGC (SEQ ID NO: 65) |
| PDPK1 (human) | GACTCTTCCGTGCGTTCTTC (SEQ ID NO: 24) | GAGGAGAAAGGTGACCCACA (SEQ ID NO: 66) |
| Pgk1 | ATGTCGCTTTCCAACAAGCTG (SEQ ID NO: 25) | GCTCCATTGTCCAAGCAGAAT (SEQ ID NO: 67) |
| Pygo1 (mouse) | TAATGTCAGCGGAACAGGAC (SEQ ID NO: 26) | TTATCTGGGCTTCCGAGTTG (SEQ ID NO: 68) |
| PYGO1 (human) | ATCCTGGCTTTGGAGGCTAT (SEQ ID NO: 27) | GTGGCCCAAAGTTAAAAGCA (SEQ ID NO: 69) |

TABLE 2-continued

List of primers used for qRT-PCR and RT-PCR analysis, cDNA synthesis, ChIP assays, and mouse genotyping; oligo ID numbers for shRNAs; and cDNAs used to prepare RNA FISH probes.

| | | |
|---|---|---|
| Rnf165 (mouse) | ATGCCTCCAGCTACAGCCTA (SEQ ID NO: 28) | GCCCAATGCTAACTGAGAGC (SEQ ID NO: 70) |
| RNF165 (human) | AGGGAGAGCTGGAAAAGGAG (SEQ ID NO: 29) | AGCCCTCCCTGGTTTAGTGT (SEQ ID NO: 71) |
| Sox5 (mouse) | GTGGAAGAGGAGGAGAGTGAGA (SEQ ID NO: 30) | AAATTCCTCAGAGTGAGGCTTG (SEQ ID NO: 72) |
| SOX5 (human) | AGGGACTCCCGAGAGCTTAG (SEQ ID NO: 31) | TTGTTCTTGTTGCTGCTTGG (SEQ ID NO: 73) |
| Stc1 (mouse) | AAGTCATACAGCAGCCCAATCA (SEQ ID NO: 32) | CCAGAAGGCTTCGGACAAGTC (SEQ ID NO: 74) |
| STC1 (human) | TGATCAGTGCTTCTGCAACC (SEQ ID NO: 33) | TCACAGGTGGAGTTTTCCAG (SEQ ID NO: 75) |
| Tcf7l2 | AAAACAGCTCCTCCGATTCC (SEQ ID NO: 34) | TAAAGAGCCCTCCATCTTGC (SEQ ID NO: 76) |
| Tsix | CAATCTCGCAAGATCCGGTGA (TSIX2F) (SEQ ID NO: 35) | TCAAGATGCGTGGATATCTCGG (P422R) (SEQ ID NO: 77) |
| Xist (non-strand specific) | CCCTGCTAGTTTCCCAATGA (SEQ ID NO: 36) | GGAATTGAGAAAGGGCACAA (SEQ ID NO: 78) |
| Xist (strand specific) | GATGCCAACGACACGTCTGA (XI5T2281F) (SEQ ID NO: 37) | AAGGACTCCAAAGTAACAATTCA (XI5T2424R) (SEQ ID NO: 79) |
| XIST (human) | ACGCTGCATGTGTCCTTAGTAGTC (SEQ ID NO: 38) | ATTTGGAGCCTCTTATAGCTGTTTG (SEQ ID NO: 80) |
| Zfp426 (mouse) | ATGACCTTTCGCTCATGGAC (SEQ ID NO: 39) | GGCAAGCTTTGCTTTAGTGC (SEQ ID NO: 81) |
| ZNF426 (human) | CTGAGGTGGGTGGATCACTT (SEQ ID NO: 40) | CTCTGCTTCCTGGGTTCAAG (SEQ ID NO: 82) |
| 1700001P01Rik (mouse) | GCTGATGTCAACTGTTTCC (SEQ ID NO: 41) | CGCAGAATCTTCCACCCT (SEQ ID NO: 83) |
| C10orf98 (human) | TCGGGCAAGGACAAAGATAC (SEQ ID NO: 42) | CGATGGCTATGAAGGGAAAA (SEQ ID NO: 84) |
| RT-PCR | Forward primer (5'→3') | Reverse primer(s) (5'→3') |
| Mecp2 (1st round) | CCGATCTGTGCAGGAGACCG (SEQ ID NO: 85) | TGGGGTCCTCGGAGCTCTCG GGCT (SEQ ID NO: 91) |
| Mecp2 (2nd round) | GACCCGGGAGACGGTCAGCA (SEQ ID NO: 86) | AGCTCTCGGGCTCAGGTGGA GGT (SEQ ID NO: 92) |
| Ascl2 | TGAGCATCCCACCCCCCTA (SEQ ID NO: 87) | CCAAACATCAGCGTCAGTATAG (SEQ ID NO: 93) |
| Kncq1ot1 | ATTGGGAACTTGGGGTGGAGGC (SEQ ID NO: 88) | GGCACACGGTATGAGAAAAGATTG (SEQ ID NO: 94) |
| Peg3 | ATGCCCACTCCGTCAGCG (SEQ ID NO: 89) | GCTCATCCTTGTGAACTTTG (SEQ ID NO: 95) |
| Zim1 | CTTCAAGCAGAGCACAAAGC (SEQ ID NO: 90) | GTGGCACACGAAAGGTTTCTC (SEQ ID NO: 96) |
| cDNA synthesis | | |
| Xist | AGAGCATTACAATTCAAGGCTC | (XI5T2688R) (SEQ ID NO: 97) |
| Tsix | GATGCCAACGACACGTCTGA | (TSIX2R) (SEQ ID NO: 98) |
| Gapdh | TGTGAGGGAGATGCTCAGTG | (GAPDR) (SEQ ID NO: 99) |

TABLE 2-continued

List of primers used for qRT-PCR and RT-PCR analysis, cDNA synthesis, ChIP assays, and mouse genotyping; oligo ID numbers for shRNAs; and cDNAs used to prepare RNA FISH probes.

| ChIP | Forward primer (5'→3') | Reverse primer(s) (5'→3') |
| --- | --- | --- |
| Xist (promoter) | TAAAGGTCCAATAAGATGTCAGAA (SEQ ID NO: 100) | GGAGAGAAACCACGGAAGAA (SEQ ID NO: 102) |
| Xist (exon 2) | GTGCTCCTGCCTCAAGAAGAA (SEQ ID NO: 101) | GCACTCTTCACTCCTCTAAATCCAG (SEQ ID NO: 103) |

| Mouse genotyping | Forward primer (5'→3') | Reverse primer(s) (5'→3') |
| --- | --- | --- |
| Dnmt1+/+ | CTTGGGCCTGGATCTTGGGGATC (SEQ ID NO: 104) | GGG CCAGTTGTGTGACTTGG (SEQ ID NO: 109) |
| Dnmt1-/- | GGGAACTTCCTGACTAGGGG (SEQ ID NO: 105) | GGGCCAGTTGTGTGACTTGG (SEQ ID NO: 110) |
| Stc1+/+ | AGCGCACGAGGCGGAACAAA (SEQ ID NO: 106) | AGAGAGCCGCTGTGAGGCGT (SEQ ID NO: 111) |
| Stc1-/- | AAAAGCCAGAGGTGCAAGAA (SEQ ID NO: 107) | TATGATCGGAATTCCTCGAC (SEQ ID NO: 112) |
| SRY | TTGTCTAGAGAGCATGGAGGGCCATGTCAA (SEQ ID NO: 108) | CCACTCCTCTGTGACACTTTAGCCCTCCGA (SEQ ID NO: 113) |

| shRNAs | |
| --- | --- |
| Gene | Oligo ID |
| Acvr1 | V2MM_75565<br>V2MM_76215 |
| Aurka | V2MM_188005<br>V2MM_71909 |
| Bmi1 | V2MM_10594<br>V2MM_2034 |
| Dnmt1 | V2MM_46797<br>V2LMM_43170 |
| Ezh2 | V2MM_35988<br>V2MM_30422 |
| Fbxo8 | V2MM_36526<br>V3LMM_494067 |
| Layn | V2MM_130482<br>V2MM_214085 |
| Nf1 | V2MM_194180<br>V2HS_76027 |
| Pdpk1 | V2MM_75859<br>V2MM_72465 |
| Pygo1 | V2MM_110610<br>V2MM_110609 |
| Rnf165 | V2MM_172866<br>TRCN0000135474 |
| Sox5 | V2MM_6385<br>V2HS_94936 |
| Stc1 | V2MM 22454<br>V2MM_26886<br>TRCN0000109921 |
| Zfp426 | V2MM 31994<br>TRCN0000085016 |
| 1700001P01Rik | V2MM_100177<br>V2MM_205788 |

TABLE 2-continued

List of primers used for qRT-PCR and RT-PCR analysis, cDNA synthesis, ChIP assays, and mouse genotyping; oligo ID numbers for shRNAs; and cDNAs used to prepare RNA FISH probes.

| cDNAs | |
| --- | --- |
| Gene | Clone number* |
| G6pdx | BAC clone RP23-13D21 |
| Lamp2 | BAC clone RP24-173A8 |
| Mecp2 | fosmid clone WI1-894A5 or WI1-1269o10 |
| Pgk1 | BAC RP23-404E5 |
| Xist | — |

*obtained from the BACPAC Resources Center

Other Embodiments

The description of the specific embodiments of the disclosure is presented for the purposes of illustration. It is not intended to be exhaustive or to limit the scope of the disclosure to the specific forms described herein. Although the disclosure includes reference to several embodiments, it will be understood by one of ordinary skill in the art that various modifications can be made without departing from the spirit and the scope of the disclosure.

All patents, patent applications, and publications referenced herein are hereby incorporated by reference. Other embodiments are in the claims.

What is claimed is:

1. A method of inducing expression of MECP2 in a mammalian cell having an inactive X chromosome, the method comprising delivering to the cell an X chromosome inactivation factor (XCIF) inhibitor in an amount effective for inducing expression of MECP2, wherein the XCIF inhibitor is (i) GSK650394 or EMD638683, (ii) an antisense oligomer comprising at least 8 nucleotides complementary to an mRNA encoded by SGK1, or (iii) an siRNA comprising a sequence that is complementary to an mRNA encoded by SGK1, wherein the cell is of a subject having Rett Syndrome.

2. The method of claim 1 further comprising determining that the cell has a mutant allele of MECP2.

3. The method of claim 1 further comprising determining that delivery of the XCIF inhibitor to the cell results in (i) induced expression of MECP2; or,
(ii) determining that an X-chromosome is reactivated; or
(iii) determining that there is decreased expression or activity of XIST.

4. The method of claim 1, wherein the cell is in a subject.

5. The method of claim 1, wherein the XCIF inhibitor is an siRNA that inhibits SGK1.

6. The method of claim 5, wherein the XCIF inhibitor is an antisense oligomer that inhibits SGK1.

7. The method of claim 1, wherein the antisense oligomer or the siRNA comprises one or more modified nucleotides and/or one or more modified internucleoside linkages.

8. The method of claim 1, wherein the XCIF inhibitor is GSK650394.

9. The method of claim 1, wherein the cell is a fibroblast, an embryonic stem cell, or a neuron.

10. The method of claim 1, wherein the cell is in vitro.

11. The method of claim 1, wherein the XCIF inhibitor is EMD638683.

* * * * *